United States Patent
Levesque et al.

(10) Patent No.: US 9,486,497 B2
(45) Date of Patent: *Nov. 8, 2016

(54) TREATMENT OF IMMUNOCOMPROMISED CONDITIONS

(75) Inventors: Jean-Pierre Levesque, Queensland (AU); Ingrid Winkler, Queensland (AU)

(73) Assignee: THE UNIVERSITY OF QUEENSLAND, Queensland (AU)

( * ) Notice: Subject to any disclaimer, the term of this patent is extended or adjusted under 35 U.S.C. 154(b) by 683 days.

This patent is subject to a terminal disclaimer.

(21) Appl. No.: 12/746,894

(22) PCT Filed: Nov. 7, 2008

(86) PCT No.: PCT/AU2008/001652
§ 371 (c)(1),
(2), (4) Date: Sep. 14, 2010

(87) PCT Pub. No.: WO2009/073911
PCT Pub. Date: Jun. 18, 2009

(65) Prior Publication Data
US 2011/0002881 A1    Jan. 6, 2011

Related U.S. Application Data

(60) Provisional application No. 61/012,756, filed on Dec. 10, 2007.

(51) Int. Cl.
*A61K 45/06*    (2006.01)
*A61K 31/00*    (2006.01)
(Continued)

(52) U.S. Cl.
CPC ........... *A61K 38/1793* (2013.01); *A61K 31/00* (2013.01); *A61K 31/675* (2013.01);
(Continued)

(58) Field of Classification Search
CPC ...... A61K 38/20; A61K 38/02; A61K 31/70; A61K 38/18; A61K 33/29; A61K 39/395; A61K 38/21; A61K 35/28
See application file for complete search history.

(56) References Cited

U.S. PATENT DOCUMENTS 5,789,573 A    8/1998 Baker et al.
5,830,871 A   11/1998 Wong et al.
(Continued)

FOREIGN PATENT DOCUMENTS

WO   WO-94/25043 A1    11/1994
WO   WO-95/31210 A1    11/1995
(Continued)

OTHER PUBLICATIONS

Kyriakides et al., (Surgery. Aug. 2000;128(2):327-31).*
(Continued)

*Primary Examiner* — Cherie M Stanfield
(74) *Attorney, Agent, or Firm* — Finnegan, Henderson, Farabow, Garrett & Dunner LLP

(57) ABSTRACT

This invention discloses the use of an E-selectin antagonist in methods and compositions for treating or preventing immunocompromised conditions resulting from medical treatment. The present invention is particular useful for prophylaxis and/or treatment of hematopoietic disorders including neutropenia, agranulocytosis, anemia and thrombocytopenia in individuals receiving or proposed to receive treatments that target rapidly dividing cells or that disrupt the cell cycle or cell division.

51 Claims, 5 Drawing Sheets

(51) Int. Cl.

| | | |
|---|---|---|
| A61K 38/17 | (2006.01) | |
| A61K 31/7004 | (2006.01) | |
| A61K 31/7016 | (2006.01) | |
| A61K 31/702 | (2006.01) | |
| A61K 31/7032 | (2006.01) | |
| A61K 31/7056 | (2006.01) | |
| A61K 38/19 | (2006.01) | |
| A61K 31/675 | (2006.01) | |
| A61K 31/70 | (2006.01) | |
| A61K 47/48 | (2006.01) | |
| C07K 14/705 | (2006.01) | |
| C07K 7/00 | (2006.01) | |
| C07K 7/06 | (2006.01) | |
| C07K 7/08 | (2006.01) | |
| C07K 16/28 | (2006.01) | |
| C07K 14/54 | (2006.01) | |
| C07K 14/475 | (2006.01) | |
| A61K 38/04 | (2006.01) | |
| A61K 38/08 | (2006.01) | |
| A61K 38/10 | (2006.01) | |
| A61K 38/18 | (2006.01) | |
| A61K 39/395 | (2006.01) | |
| A61K 39/00 | (2006.01) | |

(52) U.S. Cl.
CPC ............ *A61K 31/70* (2013.01); *A61K 31/702* (2013.01); *A61K 31/7004* (2013.01); *A61K 31/7016* (2013.01); *A61K 31/7032* (2013.01); *A61K 31/7056* (2013.01); *A61K 38/1732* (2013.01); *A61K 38/193* (2013.01); *A61K 45/06* (2013.01); *A61K 47/48376* (2013.01); *A61K 38/04* (2013.01); *A61K 38/08* (2013.01); *A61K 38/10* (2013.01); *A61K 38/178* (2013.01); *A61K 38/18* (2013.01); *A61K 39/3955* (2013.01); *A61K 2039/505* (2013.01); *C07K 7/00* (2013.01); *C07K 7/06* (2013.01); *C07K 7/08* (2013.01); *C07K 14/475* (2013.01); *C07K 14/54* (2013.01); *C07K 14/70564* (2013.01); *C07K 16/2854* (2013.01)

(56) References Cited

U.S. PATENT DOCUMENTS

| | | | | |
|---|---|---|---|---|
| 5,856,300 | A | * | 1/1999 | Rittershaus et al. ........ 424/184.1 |
| 6,121,233 | A | | 9/2000 | Magnani et al. |
| 6,387,884 | B1 | | 5/2002 | Magnani et al. |
| 6,391,857 | B1 | | 5/2002 | Magnani et al. |
| 6,407,214 | B1 | | 6/2002 | Owens |
| 7,060,685 | B2 | | 6/2006 | Magnani et al. |
| 7,361,644 | B2 | | 4/2008 | Magnani et al. |
| 2002/0086356 | A1 | | 7/2002 | Tuschl et al. |
| 2002/0165178 | A1 | | 11/2002 | Schetter et al. |
| 2003/0073632 | A1 | | 4/2003 | Ciaccia et al. |
| 2004/0067220 | A1 | * | 4/2004 | Sykes .......................... 424/93.7 |
| 2005/0181987 | A1 | | 8/2005 | Blaszczyk-Thurin et al. |
| 2005/0214283 | A1 | * | 9/2005 | Sackstein ................... 424/144.1 |
| 2006/0194745 | A1 | | 8/2006 | Magnani et al. |
| 2007/0021378 | A1 | * | 1/2007 | Varki et al. ...................... 514/56 |
| 2009/0053198 | A1 | | 2/2009 | Sackstein |
| 2011/0020270 | A1 | * | 1/2011 | Levesque et al. ............ 424/85.2 |

FOREIGN PATENT DOCUMENTS

| | | | |
|---|---|---|---|
| WO | WO 9640942 A1 * | 12/1996 | |
| WO | WO-98/46771 A2 | 10/1998 | |
| WO | WO-99/65712 A2 | 12/1999 | |
| WO | WO-00/50032 A1 | 8/2000 | |
| WO | WO-03/032925 A2 | 4/2003 | |
| WO | WO-03/097658 A2 | 11/2003 | |
| WO | WO-2004/004636 A2 | 1/2004 | |
| WO | WO 2004/094619 A2 | 11/2004 | |
| WO | WO-2005/051920 A2 | 6/2005 | |
| WO | WO-2005/054264 A2 | 6/2005 | |
| WO | WO 2006/062946 A2 | 6/2006 | |
| WO | WO 2006/089106 A2 | 8/2006 | |
| WO | WO-2006/127906 A1 | 11/2006 | |
| WO | WO-2007/028050 A1 | 3/2007 | |
| WO | WO 2007028050 A1 * | 3/2007 | |
| WO | WO-2008/060378 A2 | 5/2008 | |
| WO | WO-2008/100453 A1 | 8/2008 | |

OTHER PUBLICATIONS

Definition of allogenic. Medline Plus-Merriam-Webster Medical Dictionary (last accessed Jun. 3, 2013).*
Definition of syngeneic. Medline Plus-Merriam-Webster Medical Dictionary (last accessed Jun. 3, 2013).*
Definition of xenogeneic. Medline Plus-Merriam-Webster Medical Dictionary (last accessed Jun. 3, 2013).*
Todderund et al., (J Pharmacol Exp Ther. Sep. 1997;282(3):1298-304).*
Mulligan et al., (J Clin Invest. Oct. 1991;88(4):1396-406).*
"International Application Serial No. PCT/AU2008/001652, International Preliminary Report on Patentability issued Jun. 15, 2010", 6 pgs.
"International Application Serial No. PCT/AU2008/001652, Written Opinion mailed Jan. 13, 2009", 5 pgs.
Ali, M., et al., "Polymers beearing sLe$^x$-mimetics are superior inhibitors of E-selectin-dependent leukocyte rolling in vivo", *The FASEB Journal*, 18(1), (2004), 152-154.
Alousi, A., et al., "Reduced-Intensity Conditioning Allogeneic Hematopoietic Stem Cell Transplantation", *Clinical Advances in Hematology & Oncology*, 5(7), (2007), 560-570.
Bennett, C. F., et al., "Inhibition of Endothelial Cell Adhesion Molecule Expression with Antisense Oligonucleotides", *Journal of Immunoloy*, 152(7), (1994), 3530-3540.
Bogden, A. E., et al., "Amelioration of Chemotherapy-Induced Toxicity by Cotreatment with AcSDKP, a Tetrapeptide Inhibitor of Hematopoietic Stem Cell Proliferation", *Annals New York Academy of Sciences.*, 628, (1991), 126-139.
Bradford, G. B., et al., "Quiescence, cycling, and turnover in the primitive hematopoietic stem cell compartment", *Experimental Hematology*, 25, (1997), 445-453.
Burkhardt, K., et al., "The Significance of Adhesion Molecules in Nephrology", *Artificial Organs*, 20(5), (1996), 433-436.
Devereux, J., et al., "A comprehensive set of sequence analysis programs for the VAX", *Nucleic Acids Research*, 12(1), (1984), 387-395.
Katayama, Y., et al., "CD 44 is a physiological E-selectin ligand on neutrophils", *J. Exp. Med.*, 201(8), (2005), 1183-1189.
Khatib, A.-M., et al., "Inhibition of Hepatic Endothelial E-Selectin Expression by C-raf Antisense Oligonucleotides Blocks Colorectal Carcinoma Liver Metastasis", *Cancer Research*, 62(19), (2002), 5393-5398.
Kiel, M. J., et al., "SLAM Family Receptors Distinguish Hematopoietic Stem and Progenitor Cells and Reveal Endothelial Niches for Stem Cells", *Cell*, 121(7), (2006), 1109-1121.
Maly, P., et al., "The $\alpha(1,3)$Fucosyltransferase Fuc-TVII Controls Leukocyte Trafficking through an Essential Role in L-, E-, and P-selection Ligand Biosynthesis", *Cell*, 86(4), (1996), 643-653.
Mauch, P., et al., "Hematopoietic Stem Cell Compartment: Acute and Late Effects of Radiation Therapy and Chemotherapy", *Int. J. Radiation Oncology Biol. Phys.*, 31(5), (1995), 1319-1339.
McKenzie, J. L., et al., "Low rhodamine 123 retention identifies long-term human hematopoietic stem cells with the Lin$^-$CD34$^+$CD38$^-$population", *Blood*, 109, (2007), 543-545.
Plasterk, R. H. A., et al., "The silence of the genes", *Current Opinion in Genetics and Development*, 10, (2000), 562-567.
Roberge, J. Y., et al., "A Strategy for a Convergent Synthesis of N-Linked Glycopeptides on a Solid Support", *Science*, 269(5221), (1995), 202-204.

(56) References Cited

OTHER PUBLICATIONS

Sanz, M.-J., et al., "Roflumilast inhibits leukocyte-endothelial cell interactions, expression of adhesion molecules and microvascular permeability", *British Journal of Pharmacology*, 152(4), (2007), 481-492.

Winkler, I. G., et al., "Adhesion to E-selectin promotes growth inhibition and apoptosis of human and murine hematopietic progenitor cell independent of PSGL-1", *Blood*, 104(5), (2004), 1685-1692.

"International Application Serial No. PCT/AU2008/001652, International Search Report mailed Jan. 13, 2009", 4 pgs.

Hamamoto, N., et al., "Inhibition of Dextram Sulphat Sodium (DSS)—induced Colitis in Mice by Intracolonically Administered Antibodies Against Adhesion Molecules (Endothelial Leucocyte Adhesion Molecule-1 (ELAM-1) or Intercellular Adhesion Molecule-1 (ICAM-1))", *Clinical Experimental Immunology*, 117, (1999), 462-468.

Fruehauf, S., et al., "Protection of hematopoietic stem cells from chemotherapy-induced toxicity by multidrug-resistance 1 gene transfer", Recent Results in Cancer Research, 144, (Abstract Only), (1998), 1 pg.

USPTO Restriction Office Action mailed Aug. 17, 2012 in U.S. Appl. No. 12/747,324, filed Oct. 10, 2010 (11 pages).

USPTO Office Action mailed Feb. 4, 2013 in U.S. Appl. No. 12/747,324, filed Oct. 10, 2010 (13 pages).

USPTO Office Action mailed Jul. 10, 2014 in U.S. Appl. No. 12/747,324, filed Oct. 10, 2010 (10 pages).

USPTO Final Office Action mailed Mar. 5, 2015 in U.S. Appl. No. 12/747,324, filed Oct. 10, 2010 (10 pages).

USPTO Office Action mailed Oct. 16, 2013 in U.S. Appl. No. 12/747,324, filed Oct. 10, 2010 (17 pages).

USPTO Advisory Office Action mailed Jun. 18, 2014 in U.S. Appl. No. 12/746,894, filed Sep. 14, 2010 (4 pages).

International Application Serial No. PCT/AU2008/00181 0, International Preliminary Report on Patentability issued Jun. 15, 2010, 6 pgs.

International Application Serial No. PCT/AU2008/001810, Written Opinion mailed Feb. 18, 2009, 5 pgs.

Bedard, Patricia W., et al., "Selectin Inhibitors: A Patent Review," Expert Opin. Ther. Patents, 20:781-792, (2006).

Cottler-Fox, M.H. et al., "Stem Cell Mobilization," Amer. Sci. Hematology, 419-437, (2003).

Dagia, N.M., et al., "G-CSF Induses E-Selectin Ligand Expression on Human Myeloid Cells," Nat. Med., 10:1185-1190, (2006).

Frenette, PaulS. et al., "Sulfated Glycans Induce Rapid Hematopoietic Progenitor Cell Mobilization: Evidence For Selectin-Dependent and Independent Mechanisms," Blood, 96:2460-2468, (2000).

Katayama, Y. et al., "PSGL-1 Participates in E-Selectin-Mediated Progenitor Homing to Bone Marrow: Evidence For Cooperation Between E-Selectin Ligands and a4 Integrin," Blood, 102:2060-2067, (2003).

Komrokji, Rami S., et al., "The Colony-Stimulating Factors: Use to Prevent and treat Neutropenia and its Complications," Expert Opin. Biol. Ther., 4:1897-1910, (2004).

Kneuer, Carsten et al., "Selectins-Potential Pharmacological Targets," Drug Disc. Today, 31/22:1034-1040.

Kyriakides et al., (Surgery, Aug. 2000; 128(2):327-31).

Moore, M., "Waking Up HSCs: A new Role For E-Selectin," Nat. Med., 18:16131614, (2012).

Rood, P.M.L. et al., "E-Selectin and Very Late Activation Antigen-r Mediate Adhesion of Hematopoietic Progenitor Cells to Bone Marrow Endothelium," Ann Hematol, 79:477-484, (2000).

Sudhoff, T. et al., "Cutting Edge Communication: Circulating Endothelial Adhesion Molecules (sE-Selectin, sVCAM-1 and SICAM-1) During rHuG-CSF-Stimulated Stem Cell Mobilization," Jour. Hematother. & Stem Cell Res., 11:147-151.

Winkler, Ingrid et al., "Absence of E-Selectin at the Vascular niche Delays hematopoietic Stem Cell Turn-Over," Blood, 11 O:Abstract, 609, (2007).

Winkler, Ingrid G. et al., "Vascular Niche E-Selctin Regulates hematopoietic Stem Cell Dormancy, Self Renewal and Chemoresistance," Nature Med., 18:1651-1669, (2012).

Demain et al. Natural products for cancer themotherapy. Microbial Biotechnol4(6): 687-699, 2011.

Dykewicz, Clare, "Summary of the Guidelines for Preventing Opportunistic Infections among Hematopoietic Stem Cell Transplant Recipients," Clin. Infect. Dis. (2001) 33(2):139-144, available at /cid.oxfordjournals.org/ content/33/2/139.short (6 pages).

Pamphilon et al., "Stem Cell Donation—What advice can be given to the donor?," Published in final edited form as Br. J. Haematol., Oct. 2009, 147(1):71-76, available at www.ncbi.nlm.nih.gov/pmc/articles/ PMC3409390/pdf/nihms-374766.pdf (10 pages).

Togel, Florian et al., "Administered mesenchymal stem cells protect against ischemic acute renal failure through differntiaion-independent mechanisms,"0 Am. J. Physiol. Renal. Physiol. (Feb. 2005) 289:F31-F42, available at jprenal.physiology.org/content/ajprenal/289/1/F31.full.pdf (12 pages).

\* cited by examiner

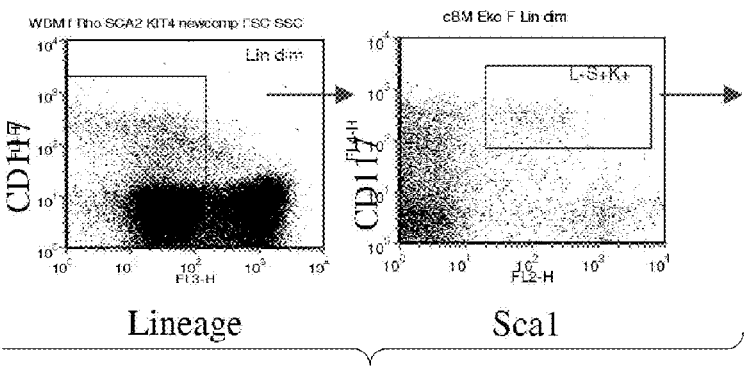
*Fig. 2A*
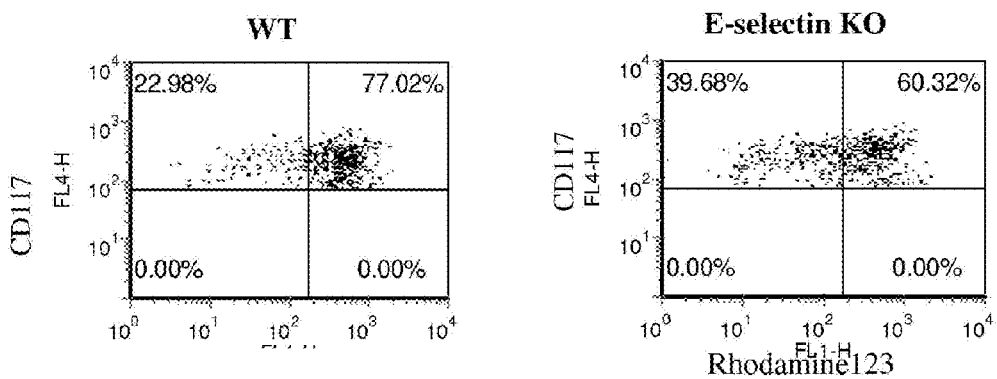
*Fig. 2B*  *Fig. 2C*
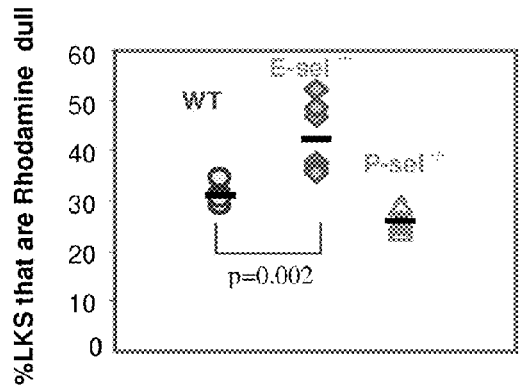
*Fig. 2D*

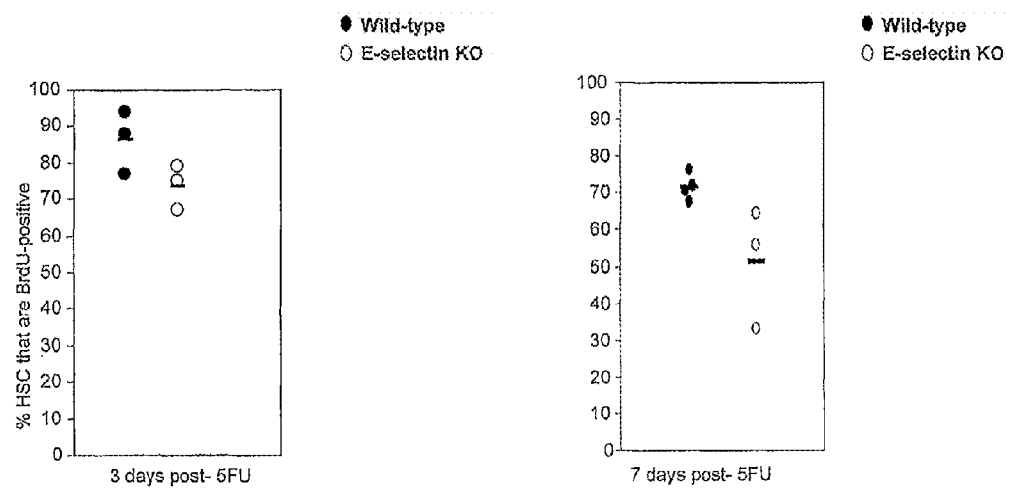
*Fig. 3A*    *Fig. 3B*
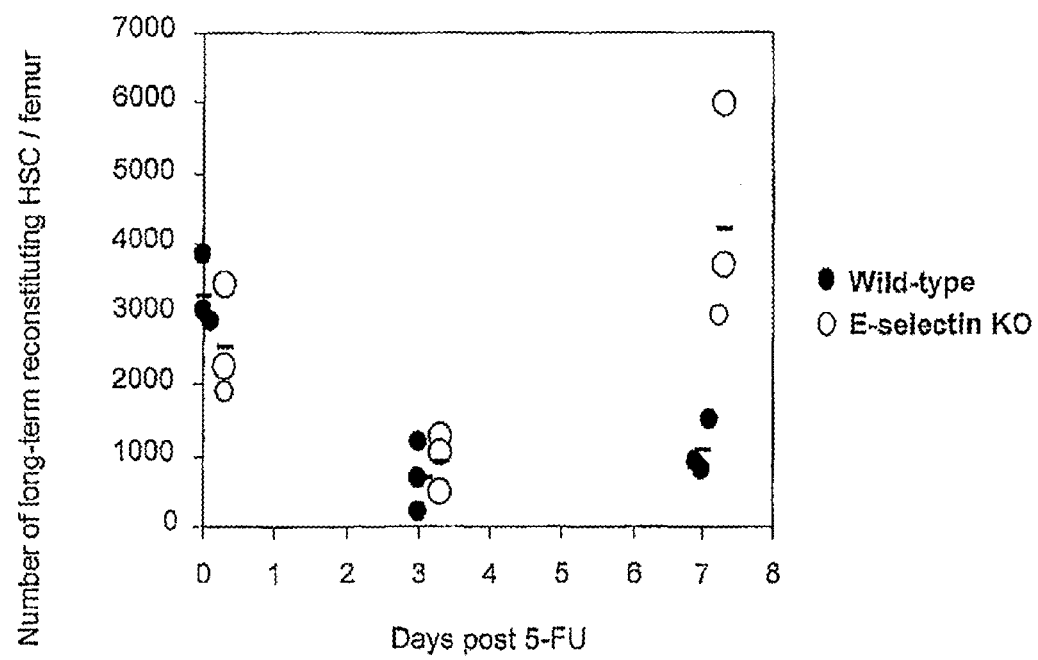
*Fig. 4*

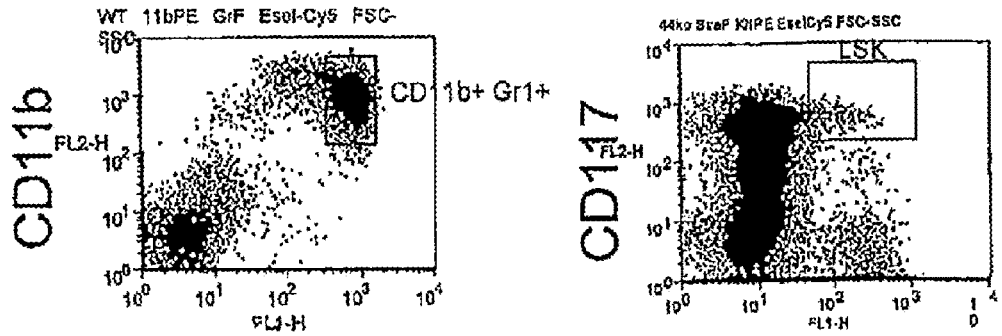
*Fig. 6A*  *Fig. 6B*
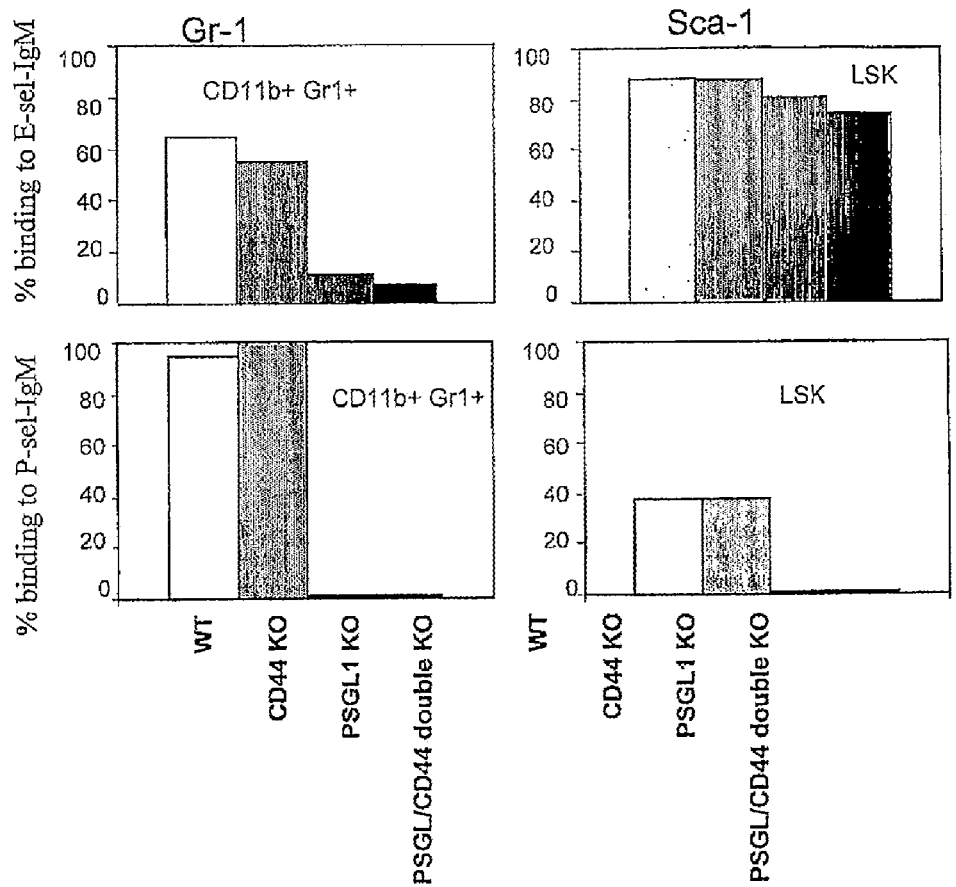
*Fig. 6C*

TREATMENT OF IMMUNOCOMPROMISED CONDITIONS

RELATED APPLICATIONS

This application is a U.S. National Stage Filing under 35 U.S.C. 371 from International Patent Application Serial No. PCT/AU2008/001652, filed Nov. 7, 2008, and published on Jun. 18, 2009 as WO 2009/073911 A1, which claims the priority benefit under 35 U.S.C. 119 to U.S. Provisional Application Ser. No. 61/012,756, filed Dec. 10, 2007, the contents of which applications and publication are incorporated herein by reference in their entirety.

FIELD OF THE INVENTION

This invention relates generally to the use of an E-selectin antagonist in methods and compositions for treating or preventing immunocompromised conditions resulting from medical treatment. The present invention is particular relevant for prophylaxis and/or treatment of hematopoeitic disorders including neutropenia, agranulocytosis, anemia and thrombocytopenia in individuals receiving or proposed to receive treatments that target rapidly dividing cells or that disrupt the cell cycle or cell division.

Bibliographic details of certain publications numerically referred to in this specification are collected at the end of the description.

BACKGROUND OF THE INVENTION

Hematopoiesis is an essential, lifelong process whereby highly specialized blood cells are generated from hematopoietic stem cells, including cells responsible for carbon dioxide and oxygen transport (erythrocytes), blood clotting (platelets), humoral immunity (B lymphocytes), cellular immunity (T lymphocytes), as well as cells which respond to foreign organisms and their products (granulocytes, monocytes, and macrophages).

Mature functional end cells and their immediate precursors have a limited life-span and a limited proliferative capacity and hence are not self-maintaining. Thus, these cells are continuously replaced from a pool of more primitive proliferating progenitor cells. The proliferation and self-renewal of these cells depend on stem cell factor (SCF). Glycoprotein growth factors regulate the proliferation and maturation of the cells that enter the blood from the marrow, and cause cells in one or more committed cell lines to proliferate and mature. Three more factors which stimulate the production of committed stem cells are called colony-stimulating factors (CSFs) and include granulocyte-macrophage CSF (GM-CSF), granulocyte CSF (G-CSF) and macrophage CSF (M-CSF).

Under normal conditions, senescent mature cells are continuously removed and replaced with newly generated cells. Under stress conditions, there may be an increased rate at which blood cells are destroyed or lost, or there may be a compromised capacity to replenish cells undergoing normal senescent attrition, resulting in depletion of erythrocytes (anemia), platelets (thrombocytopenia), leukocytes (leukopenia) including neutrophil granulocytes (neutropenia), and/or agranulocytosis (complete absence of white cells).

Radiation and chemotherapeutic treatment frequently produce severe reversible neutropenia or agranulocytosis, thrombocytopenia, and anemia. This effect comes about as the result of the toxicity of these treatment regimens on dividing hematopoietic stem cells and the consequent depletion of hematopoietic precursors and of the cells responsible for producing the required CSFs and hematopoietic potentiators. The depletion of hematopoietic precursors in the bone marrow associated with chemotherapy and irradiation sometimes results in life-threatening hemorrhagic and infectious complications. Severe suppression of hematopoiesis is a major factor in limiting chemotherapy use and dose escalation. Replacement of depleted blood cell types by transfusion is not always practical or desirable as it often affords only temporary improvement, is expensive, and is associated with risks of infection, fluid overload, and immune-mediated adverse reactions. Thus there has been intense interest in developing methods of using hematopoietic CSFs and potentiators to treat neutropenia, agranulocytosis, thrombocytopenia, and anemia.

In recent years three recombinant human hematopoietic growth factors became available for clinical use: EPO for the treatment of anemia, and granulocyte colony-stimulating factor (G-CSF) and GM-CSF for neutropenia. While these factors have proven to be generally safe and effective, they are expensive. Nevertheless, other hematopoietic growth factors and cytokines, including TPO and IL-3, IL-6, and IL-11, are under development and/or study as potential hematopoietic agents. In spite of the availability of these growth factors, there remains a need to provide additional methods of altering the hematopoietic state of an individual.

SUMMARY OF THE INVENTION

The present invention is predicated in part on the discovery that E-selectin, a $Ca^{2+}$-dependent adhesion molecule expressed by bone marrow endothelial sinuses as well as on inflamed endothelial cells, regulates hematopoietic stem cell turn-over in the bone marrow. In particular, the present inventors have determined that the absence of E-selectin at the endothelial niche significantly delays hematopoietic stem cell turnover and that blocking E-selectin mediated adhesive interactions will protect hematopoietic stem cells from medical treatments that target rapidly dividing cells, such as radiation and chemotherapeutic treatments. These discoveries have been reduced to practice in methods and compositions for treating or preventing immunocompromised conditions, which result from medical treatment, such as neutropenia, agranulocytosis, thrombocytopenia, and anemia.

Accordingly, in one aspect, the present invention provides methods for treating or preventing an immunocompromised condition in a subject, which condition results from exposure of the subject to a medical treatment. These methods generally comprise administering to the subject an E-selectin antagonist in an effective amount to treat or prevent the immunocompromised condition. Suitably, the immunocompromised condition is selected from neutropenia, agranulocytosis, thrombocytopenia, and anemia. In some embodiments, the methods further comprise identifying a subject having or at risk of developing the immunocompromised condition.

In some embodiments, the medical treatment targets rapidly dividing cells or disrupts the cell cycle or cell division. In illustrative examples of this type, the medical treatment is selected from chemotherapy and radiation therapy.

Non limiting examples of suitable E-selectin antagonists include small molecules, such as nucleic acids, peptides, polypeptides, peptidomimetics, carbohydrates, lipids or other organic (carbon containing) or inorganic molecules. Suitably, the E-selectin antagonist is selected from antigen-binding molecules that are immuno-interactive with E-selectin, peptides that bind to E-selectin and that block cell-cell adhesion, and carbohydrate or peptide mimetics of E-selectin ligands. In some embodiments, the E-selectin antagonist reduces the expression of an E-selectin gene or the level or functional activity of an expression product of that gene. For example, the E-selectin antagonist may antagonize the function of E-selectin, including reducing or abrogating the activity of at least one of its ligand-binding sites. Suitably, the E-selectin antagonist reduces the expression of the E-selectin gene or the level or functional activity of an expression product of that gene by at least 10%, 20%, 30%, 40%, 50%, 60%, 70%, 80%, 90% relative to the expression, level or functional activity in the absence of the agent. In some embodiments, the E-selectin antagonist is a selective E-selectin antagonist.

The E-selectin antagonist is suitably administered to the subject simultaneously, sequentially or separately with the medical treatment. For example, the E-selectin antagonist may be administered to the subject prior to, during or after the medical treatment. In some embodiments, the administration of the E-selectin is a prophylactic treatment (e.g., the subject is preparing to undergo chemotherapy or radiation treatment). In others, it is a therapeutic treatment (e.g., the subject has received at least one dose of chemotherapy or at least one radiation treatment).

Suitably, the medical treatment comprises treatment or prophylaxis of a cancer (e.g., a primary cancer or a metastatic cancer) or an autoimmune disease.

The present invention also contemplates combination therapy or prophylaxis of the immunocompromised condition and accordingly, the method may further comprise exposing the subject to an ancillary treatment that treats or prevents the immunocompromised condition. In illustrative examples of this type, the immunocompromised condition is anemia and the ancillary treatment may comprise administering to the subject an anemia medicament selected from recombinant erythropoietin (EPO), recombinant granulocyte-macrophage colony-stimulating factor (GM-CSF), recombinant granulocyte colony-stimulating factor (G-CSF), recombinant interleukin 11 (IL-11), ferrous iron, ferric iron, vitamin B12, vitamin B6, vitamin C, vitamin D, calcitriol, alphacalcidol, folate, androgen, and carnitine. In other illustrative examples, the immunocompromised condition is thrombocytopenia and the ancillary treatment may comprise administering to the subject a thrombocytopenia medicament selected from a glucocorticoid, recombinant thrombopoietin (TPO), recombinant megakaryocyte growth and development factor (MGDF), pegylated recombinant MGDF, lisophylline, recombinant IL-1, recombinant IL-3, recombinant IL-6, and recombinant IL-11. In still other illustrative examples, the immunocompromised condition is neutropenia and the ancillary treatment suitably comprises administering to the subject a neutropenia medicament selected from glucocorticoid, recombinant G-CSF, recombinant GM-CSF, recombinant macrophage colony-simulating factor (M-CSF), recombinant IL-1, recombinant IL-3, recombinant IL-6, immunoglobulin, androgens, recombinant IFN-γ, small molecule G-CSF mimetics, G-CSF receptor antagonists, IL-3 receptor antagonists, and uteroferrin. In further illustrative examples, the immunocompromised condition is agranulocytosis and the ancillary treatment suitably comprises administering to the subject an agranulocytosis medicament selected from an agent that stimulates the production of granulocytes (e.g., recombinant G-CSF and recombinant GM-CSF) and hematopoeitic stem cells (e.g., transplantation of bone marrow) into the subject. In some embodiments, the E-selectin antagonist is administered to the subject simultaneously, sequentially or separately with the ancillary treatment.

In some embodiments, the medical treatment is likely to expose the subject to a higher risk of infection. Accordingly, in these embodiments, the methods may further comprise administering simultaneously, sequentially or separately with the E-selectin antagonist at least one anti-infective agent that is effective against an infection that develops or that has an increased risk of developing from the immunocompromised condition, wherein the anti-infective is selected from antimicrobials, antibiotics, antivirals, antifungals, anthelmintics, antiprotozoals and nematocides.

Typically, the E-selectin antagonist is administered on a routine schedule, for example, every day, at least twice a week, at least three times a week, at least four times a week, at least five times a week, at least six times a week, every week, every other week, every third week, every fourth week, every month, every two months, every three months, every four months, and every six months.

In some advantageous embodiments, the E-selectin antagonist is useful for treating or preventing hematopoeitic disorders such as neutropenia, agranulocytosis, thrombocytopenia, and anemia, which may result, for example, from myelosuppressive treatments that target rapidly dividing cells or that disrupt the cell cycle or cell division (e.g., chemotherapy or radiation therapy). It is proposed, therefore, that since administration of the E-selectin antagonist will reduce the risk of having or developing a hematopoeitic disorder as a side effect of the myelosuppressive treatment, it is possible to administer higher therapeutic doses of a chemotherapeutic agent or radiation to a subject in order to kill or inhibit the growth or proliferation of a tumor or to treat or prevent an autoimmune disease in the subject. It is generally not desirable to administer such high doses alone, in the absence of the E-selectin antagonist, because of the side effects resulting from the high doses. Accordingly, in another aspect, the present invention provides methods for increasing the dose of a medicament in a subject, wherein the medicament results or increases the risk of developing an immunocompromised condition. These methods generally comprise administering the medicament to the subject in a dose that ordinarily induces side effects (e.g., the development of the immunocompromised condition), together with an amount of an E-selectin antagonist that is effective for inhibiting or preventing the induction of those side effects.

Non limiting examples of suitable E-selectin antagonists include small molecules, such as nucleic acids, peptides, polypeptides, peptidomimetics, carbohydrates, lipids or other organic (carbon containing) or inorganic molecules. In some embodiments, the E-selectin antagonist is selected from antigen-binding molecules that are immuno-interactive with E-selectin, peptides that bind to E-selectin and that block cell-cell adhesion, and carbohydrate or peptide mimetics of E-selectin ligands.

In some embodiments, the E-selectin antagonist reduces the expression of an E-selectin gene or the level or functional activity of an expression product of that gene. For example, the E-selectin antagonist may antagonize the function of E-selectin, including reducing or abrogating the activity of at least one of its ligand-binding sites. Suitably, the E-selectin antagonist reduces the expression of the E-selectin gene or the level or functional activity of an expression product of that gene by at least 10%, 20%, 30%, 40%, 50%, 60%, 70%, 80%, 90% relative to the expression, level or functional activity in the absence of the agent.

In yet another aspect, the present invention provides pharmaceutical compositions for treating or preventing a disease (e.g., cancer or an autoimmune disease) that is treatable or preventable by a medical treatment that targets rapidly dividing cells or that disrupts the cell cycle or cell division (e.g., chemotherapy or radiation therapy). These compositions generally comprise an E-selectin antagonist and at least one other agent selected from a chemotherapeutic agent (e.g., a cytotoxic agent), a radiosensitizing agent, an anemia medicament, a thrombocytopenia medicament, a neutropenia medicament, an agranulocytosis medicament and an anti-infective agent. In some embodiments, the compositions further comprise a pharmaceutically acceptable carrier.

In yet another aspect, the invention provides methods for identifying agents that are useful for treating or preventing an immunocompromised condition in a subject, wherein the condition results from exposure of the subject to a medical treatment. These methods typically comprise contacting a preparation with a test agent, wherein the preparation comprises (i) a polypeptide comprising an amino acid sequence corresponding to at least a biologically active fragment of an E-selectin polypeptide, or to a variant or derivative thereof; or (ii) a polynucleotide comprising at least a portion of a genetic sequence (e.g., a transcriptional element) that regulates the expression of an E-selectin gene, which is operably linked to a reporter gene. A detected reduction in the level and/or functional activity of the polypeptide, or an expression product of the reporter gene, relative to a normal or reference level and/or functional activity in the absence of the test agent, indicates that the agent is useful for useful for treating or preventing the immunocompromised condition.

In some embodiments, an agent which is useful for treating or preventing the immunocompromised condition antagonises the binding between E-selectin and an E-selectin ligand, as determined by: contacting an E-selectin and the ligand with the agent and measuring the binding of the E-selectin with the ligand. In these embodiments, agents can bind to the E-selectin or to the ligand and test positive when they reduce or abrogate the binding of the E-selectin with the ligand. The agents can be small molecules or antigen-binding molecules specific for the E-selectin or for the ligand.

Still another aspect of the present invention provides methods of producing an agent for treating or preventing the immunocompromised condition that results from a medical treatment, as broadly described above. These methods generally comprise: testing an agent suspected of antagonizing the function of E-selectin as broadly described above; and synthesising the agent on the basis that it tests positive for the antagonism. Suitably, the method further comprises derivatising the agent, and optionally formulating the derivatised agent with a pharmaceutically acceptable carrier and/or diluent, to improve the efficacy of the agent for treating or preventing the immunocompromised condition.

Still another aspect of the present invention provides the use of an E-selectin antagonist for treating or preventing an immunocompromised condition that results from a medical treatment, as broadly described above. In some embodiments, the E-selectin antagonist is prepared or manufactured as a medicament for this purpose.

BRIEF DESCRIPTION OF THE DRAWINGS

FIGS. 2A-D are a graphical representation showing that LSK hematopoietic stem cells are less metabolically active in E-selectin KO mice than wild-type mice. Upper panels show the gating strategy to measure rhodamine123 incorporation into LSK hematopoietic stem cells. The bottom panel shows the percentage of bone marrow LSK hematopoietic stem cells that incorporate low levels of Rhodamine123.

FIGS. 3A-B are a graphical representation showing lower HSC turn-over in bone marrow of E-selectin KO mice following chemotherapy with the cytotoxic drug 5FU. These data represent the percentage of cycling lineage-negative Sca1-positive CD41-negative CD48-negative CD150-positive long-term reconstituting hematopoietic stem cells that incorporated BrdU over a period of 17 hours of continuous administration of BrdU prior sacrifice at days 3 (left panel) and day 7 (right panel) following administration of a single dose of 150 mg/kg of 5FU. Each dot represents result from an individual mouse. The horizontal bar is the average of the group.

FIG. 4 is a graphical representation showing higher number of long-term reconstituting hematopoietic stem cells in E-selectin KO bone marrow following chemotherapy with the cytotoxic drug 5-FU. These data represent the total number of lineage-negative Sca1-positive CD41-negative CD48-negative CD150-positive long-term reconstituting hematopoietic stem cells per femur at the indicated time-points following administration of a single dose of 150 mg/kg of 5FU. Each dot represents result from an individual mouse. The horizontal bar is the average of the group.

FIGS. 6A-C are a graphical representation showing that deletion of CD44 and PSGL1 genes does not perturb binding of soluble recombinant E-selectin-IgMFc fusion protein to the surface of LSK hematopoietic stem cells. Top panels show the gating strategy to measure selectin-IgM binding at the surface of bone marrow CD11b-positive Gr1-positive granulocytes and lineage-negative Sca1-positive CD117-positive (LSK) hematopoietic stem cells. The bottom panels show the proportion of these binding either the recombinant E-selectin-IgMFc or P-selectin-IgMFc fusion proteins.

DETAILED DESCRIPTION OF THE INVENTION

1. Definitions

Figure 1A:
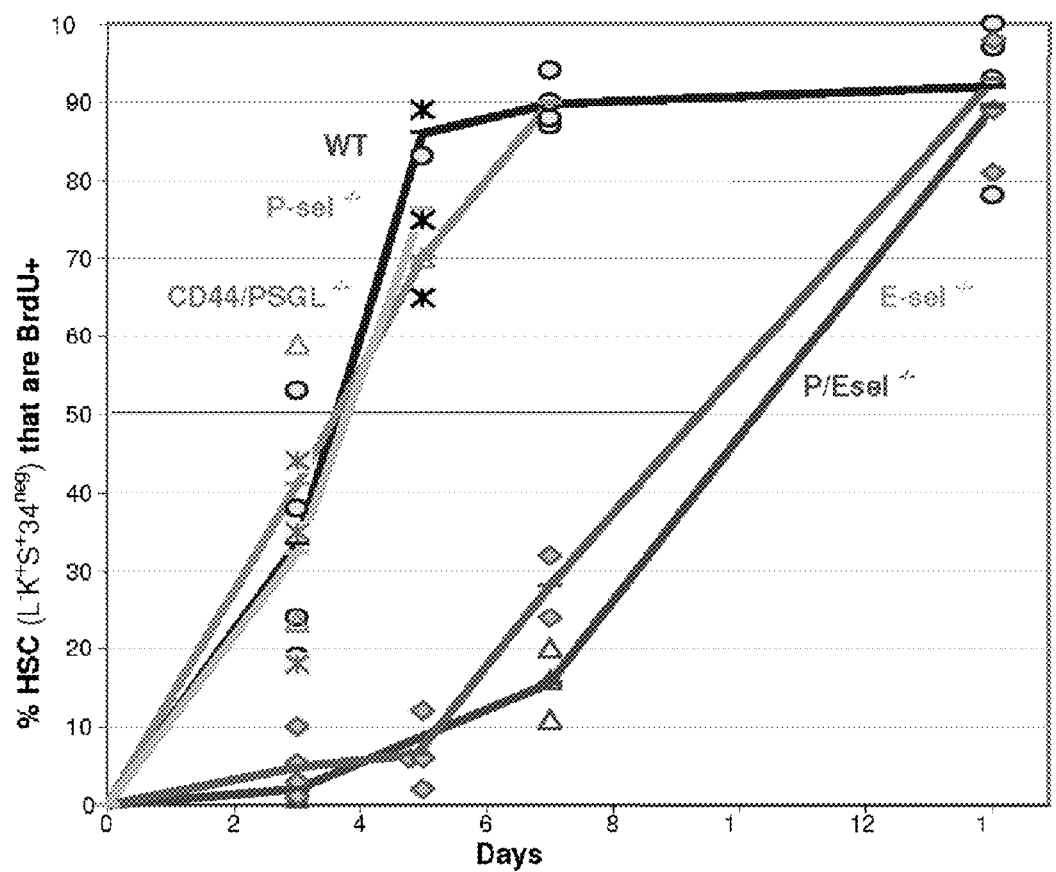
FIGS. 1A and B are is a graphical and photographic representation, respectively, showing the kinetics of BrdU incorporation in vivo in hematopoietic stem cells isolated from the bone marrow of mice lacking P-selectin and/or E-selectin genes. The top panel shows the percentage of bone marrow LSK34-hematopoietic stem cells positive for BrdU in different knock-out strains and wild-type mice. The bottom panel shows a typographical micrograph of BrdU staining (brown colour) in hematopoietic stem cells isolated from bone marrow of wild-type and P/E-selection double knock-out mice fed for 5 days with BrdU.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The term "agent" or "modulatory agent" includes a compound that induces a desired pharmacological and/or physiological effect. The term also encompass pharmaceutically acceptable and pharmacologically active ingredients of those compounds specifically mentioned herein including but not limited to salts, esters, amides, prodrugs, active metabolites, analogs and the like. When the above term is used, then it is to be understood that this includes the active agent per se as well as pharmaceutically acceptable, pharmacologically active salts, esters, amides, prodrugs, metabolites, analogs, etc. The term "agent" is not to be construed narrowly but extends to small molecules, proteinaceous molecules such as peptides, polypeptides and proteins as well as compositions comprising them and genetic molecules such as RNA, DNA and mimetics and chemical analogs thereof as well as cellular agents. The term "agent" includes a cell which is capable of producing and secreting the polypeptides referred to herein as well as a polynucleotide comprising a nucleotide sequence that encodes this polypeptide. Thus, the term "agent" extends to nucleic acid constructs including vectors such as viral or non-viral vectors, expression vectors and plasmids for expression in and secretion in a range of cells.

An "agranulocytosis medicament" as used herein refers to a composition of matter which reduces the symptoms related to agranulocytosis, prevents the development of agranulocytosis, or treats existing agranulocytosis.

An "anemia medicament" as used herein refers to a composition of matter which reduces the symptoms related to anemia, prevents the development of anemia, or treats existing anemia.

As used herein, the term "antagonist" means an agent that decreases or inhibits the function or biological activity of E-selectin (also known as CD62E, ELAM-1, LECAM-2) or the expression of the E-selectin gene.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

"Antigenic or immunogenic activity" refers to the ability of a polypeptide, fragment, variant or derivative according to the invention to produce an antigenic or immunogenic response in an animal, suitably a mammal, to which it is administered, wherein the response includes the production of elements which specifically bind the polypeptide or fragment thereof.

Reference herein to "bacteria" or "bacterial infection" includes any bacterial pathogen including emerging bacterial pathogen of vertebrates. Representative bacterial pathogens include without limitation species of: *Acinetobacter, Actinobacillus, Actinomycetes, Actinomyces, Aeromonas, Bacillus, Bacteroides, Bordetella, Borrelia, Brucella* (brucellosis), *Burkholderia, Campylobacter, Citrobacter, Clostridium, Corynebacterium, Enterobacter, Enterococcus, Erysipelothrix, Escherichia, Francisella, Haemophilus, Helicobacter, Klebsiella, Legionella, Leptospira, Listeria,* *Micrococcus, Moraxella, Morganella, Mycobacterium* (tuberculosis), *Nocardia, Neisseria, Pasteurella, Plesiomonas, Propionibacterium, Proteus, Providencia, Pseudomonas, Rhodococcus, Salmonella, Serratia, Shigella, Staphylococcus, Stenotrophomonas, Streptococcus, Treponema, Vibrio* (cholera) and *Yersinia* (plague).

By "co-administered," "co-administration" and the like is meant simultaneous administration in the same formulation or in two different formulations via the same or different routes or sequential administration by the same or different routes. For example, an E-selectin antagonist may be administered together with another agent in order to enhance its effects. By "sequential" administration is meant a time difference of from seconds, minutes, hours or days between the administration of the two types of molecules. These molecules may be administered in any order.

Throughout this specification, unless the context requires otherwise, the words "comprise," "comprises" and "comprising" will be understood to imply the inclusion of a stated step or element or group of steps or elements but not the exclusion of any other step or element or group of steps or elements.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions or deletions that provide for functional equivalent molecules.

By "effective amount," is meant the administration of an amount of active agent to a subject, either in a single dose or as part of a series or slow release system, which is effective for prevention or treatment. The effective amount will vary depending upon the health and physical condition of the subject and the taxonomic group of individual to be treated, the formulation of the composition, the assessment of the medical situation, and other relevant factors.

As used herein, the term "function" refers to a biological, enzymatic, or therapeutic function.

The terms "expression" or "gene expression" refer to either production of RNA message or translation of RNA message into proteins or polypeptides. By "expression vector" is meant any genetic element capable of directing the transcription of a polynucleotide contained within the vector and suitably the synthesis of a peptide or polypeptide encoded by the polynucleotide. Such expression vectors are known to practitioners in the art.

The term "gene" as used herein refers to any and all discrete coding regions of the cell's genome, as well as associated non-coding and regulatory regions. The term is intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

"Homolog" is used herein to denote a gene or its product which is related to another gene or product by decent from a common ancestral DNA sequence.

"Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances as known to those of skill in the art.

The phrase "hybridizing specifically to" and the like refer to the binding, duplexing, or hybridizing of a molecule only to a particular nucleotide sequence under stringent conditions when that sequence is present in a complex mixture (e.g., total cellular) DNA or RNA.

The term "immunocompromised" as used herein refers to a subject with an innate, acquired, or induced inability to develop a normal immune response. An immunocompromised subject, therefore, has a weakened or impaired immune system relative to one of a normal subject. A subject with a weakened or impaired immune system has an "immunodeficiency" or "immunocompromised condition," which is associated with a primary or secondary deficiency, induced or non-induced, in one or more of the elements of the normal immune defense system. An immunocompromised condition is commonly due to a medical treatment, e.g., radiation therapy, chemotherapy or other immunosuppressing treatment, such as induced by treatment with steroids, cyclophosphamide, azathioprine, methotrexate, cyclosporine or rapamycin, in particular in relation to cancer treatment or the treatment or prevention of transplant rejection. However, it will be understood that the phrase "risk of acquiring an immunocompromised condition resulting from a medical treatment" refers only to medical treatments that leads to or confers an immunocompromised condition, especially chemotherapy or other immunosuppressing treatment, such as induced by treatment with radiation, steroids, cyclophosphamide, azathioprine, methotrexate, cyclosporine or rapamycin. The presence of an immunocompromised condition in a subject can be diagnosed by any suitable technique known to persons of skill the art. Strong indicators that an immunocompromised condition may be present is when rare diseases occur or the subject gets ill from organisms that do not normally cause diseases, especially if the subject gets repeatedly infected. Other possibilities are typically considered, such as recently acquired infections—for example, HIV, hepatitis, tuberculosis, etc. Generally, however, definitive diagnoses are based on laboratory tests that determine the exact nature of the immunocompromised condition. Most tests are performed on blood samples. Blood contains antibodies, lymphocytes, phagocytes, and complement components—all of the major immune components that might cause immunodeficiency. A blood cell count will determine if the number of phagocytic cells or lymphocytes is below normal. Lower than normal counts of either of these two cell types correlates with an immunocompromised condition. The blood cells are also checked for their appearance. Occasionally, a subject may have normal cell counts, but the cells are structurally defective. If the lymphocyte cell count is low, further testing is usually conducted to determine whether any particular type of lymphocyte is lower than normal. A lymphocyte proliferation test may be conducted to determine if the lymphocytes can respond to stimuli. The failure to respond to stimulants correlates with an immunocompromised condition. Antibody levels and complement levels can also be determined for diagnosing the presence of an immunocompromised condition. However, it shall be understood that the methods of the present invention are not predicated upon diagnosing the absence of an immunocompromised condition in the subjects to be treated.

Reference herein to "immuno-interactive" includes reference to any interaction, reaction, or other form of association between molecules and in particular where one of the molecules is, or mimics, a component of the immune system.

Reference herein to a "infectious agent," "infectious organism," "microbe" or "pathogen" includes any one or more species or subspecies of bacterium, fungus, virus, algae, parasite, (including ecto- or endo-parasites) prion, oomycetes, slime, moulds, nematodes, mycoplasma and the like. The present invention is particularly suited to treating or preventing mixed infections by more than one microbe. Pathogenic algae include *Prototheca* and *Pfiesteria*. Also includes within the scope of these terms are prion proteins causing conditions such as Creutzfeldt-Jakob disease. As the skilled artisan will appreciate, pathogenicity or the ability of a classically non-pathogenic agent to infect a subject and cause pathology can vary with the genotype and expression profile of the infectious agent, the host and the environment. Fungal pathogens include without limitation species of the following genera: *Absidia, Acremonium, Aspergillus, Basidiobolus, Bipolaris, Blastomyces, Candida* (yeast), *Cladophialophora, Coccidioides, Cryptococcus, Cunninghamella, Curvularia, Epidermophyton, Exophiala, Exserohilum, Fonsecaea, Fusarium, Geotrichum, Histoplasma, Hortaea, Lacazia, Lasiodiplodia, Leptosphaeria, Madurella, Malassezia, Microsporum, Mucor, Neotestudina, Onychocola, Paecilomyces, Paracoccidioides, Penicillium, Phialophora, Piedraia, Piedra, Pityriasis, Pneumocystis, Pseudallescheria, Pyrenochaeta, Rhizomucor, Rhizopus, Rhodotorula, Scedosporium, Scopulariopsis, Scytalidium, Sporothrix, Trichophyton, Trichosporon* and *Zygomycete*. Pathogenic conditions include any deleterious condition that develops as a result of infection with an infectious organism.

By "isolated" is meant material that is substantially or essentially free from components that normally accompany it in its native state.

The term "lower alkyl" refers to straight and branched chain alkyl groups having from 1 to 6 carbon atoms, such as methyl, ethyl, n-propyl, iso-propyl, n-butyl, tert-butyl, sec-butyl, n-pentyl, n-hexyl, 2-methylpentyl, and the like. In some embodiments, the lower alkyl group is methyl or ethyl.

The term "lower alkoxy" refers to straight and branched chain alkoxy groups having from 1 to 6 carbon atoms, such as methoxy, ethoxy, n-propoxy, iso-propoxy, n-butoxy, tertbutoxy, sec-butoxy, n-pentoxy, n-hexoxy, 2-methyl-pentoxy, and the like. Usually, the lower alkoxy group is methoxy or ethoxy.

By "modulating" is meant increasing or decreasing, either directly or indirectly, the level or functional activity of a target molecule. For example, an agent may indirectly modulate the level/activity by interacting with a molecule other than the target molecule. In this regard, indirect modulation of a gene encoding a target polypeptide includes within its scope modulation of the expression of a first nucleic acid molecule, wherein an expression product of the first nucleic acid molecule modulates the expression of a nucleic acid molecule encoding the target polypeptide.

A "neutropenia medicament" as used herein refers to a composition of matter which reduces the symptoms related to neutropenia, prevents the development of neutropenia, or treats existing neutropenia.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

By "operably linked" is meant that transcriptional and translational regulatory polynucleotides are positioned relative to a polypeptide-encoding polynucleotide in such a manner that the polynucleotide is transcribed and the polypeptide is translated.

By "pharmaceutically acceptable carrier" is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, amide, prodrug or derivative of a compound as provided herein is a salt, ester, amide, prodrug or derivative that this not biologically or otherwise undesirable.

Pathogenic "protozoa" include, without limitation, *Trypanosoma, Leishmania, Giardia, Trichomonas, Entamoeba, Naegleria, Acanthamoeba, Plasmodium, Toxoplasma, Cryptosporidium, Isospora* and *Balantidium*.

Larger pathogenic "parasites" include those from the phyla Cestoda (tapeworms), Nematoda and Trematoda (flukes). Pathogenic trematodes are, for example, species of the following genera; *Schistosoma, Echinostoma, Fasciolopsis, Clonorchis, Fasciola, Opisthorchis* and *Paragonimus*. Cestode pathogens include, without limitation, species from the following orders; Pseudophyllidea (e.g., *Diphyllobothrium*) and Cyclophyllidea (e.g., *Taenia*). Pathogenic nematodes include species from the orders; Rhabditida (e.g., *Strongyloides*), Strongylida (e.g., *Ancylostoma*), Ascaridia (e.g., *Ascaris, Toxocara*), Spirurida (e.g., *Dracunculus, Brugia, Onchocerca, Wucheria*) and Adenophorea (e.g., *Trichuris* and *Trichinella*).

The terms "polynucleotide," "genetic material," "genetic forms," "nucleic acids" and "nucleotide sequence" include RNA, cDNA, genomic DNA, synthetic forms and mixed polymers, both sense and antisense strands, and may be chemically or biochemically modified or may contain nonnatural or derivatized nucleotide bases, as will be readily appreciated by those skilled in the art.

The terms "polynucleotide variant" and "variant" refer to polynucleotides displaying substantial sequence identity with a reference polynucleotide sequence or polynucleotides that hybridise with a reference sequence under stringent conditions as known in the art (see for example Sambrook et al., Molecular Cloning. A Laboratory Manual", Cold Spring Harbor Press, 1989). These terms also encompass polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains a biological function or activity of the reference polynucleotide. The terms "polynucleotide variant" and "variant" also include naturally-occurring allelic variants.

The terms "polypeptide," "proteinaceous molecule," "peptide" and "protein" are used interchangeably herein to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers. These terms do not exclude modifications, for example, glycosylations, acetylations, phosphorylations and the like. Soluble forms of the subject proteinaceous molecules are particularly useful. Included within the definition are, for example, polypeptides containing one or more analogs of an amino acid including, for example, unnatural amino acids or polypeptides with substituted linkages.

The term "polypeptide variant" refers to polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted, or replaced with different amino acids.

As used herein, the terms "prevent," "prevented," or "preventing," when used with respect to the treatment of an immunocompromised condition (e.g., anemia, thrombocytopenia, agranulocytosis or neutropenia), refers to a prophylactic treatment which increases the resistance of a subject to developing the immunocompromised condition or, in other words, decreases the likelihood that the subject will develop the immunocompromised condition as well as a treatment after the immunocompromised condition has begun in order to reduce or eliminate it altogether or prevent it from becoming worse.

As used herein; a "reporter gene" refers to any gene or DNA that expresses a product that is detectable by spectroscopic, photochemical, biochemical, enzymatic, immunochemical, electrical, optical or chemical means. The preferred reporter gene to which a promoter element is ligated is luciferase. Other reporter genes for use for this purpose include, for example, β-galactosidase gene (β-gal) and chloramphenicol acetyltransferase gene (CAT) Assays for expression produced in conjunction with each of these reporter gene elements are well-known to those skilled in the art.

The term "selective" refers to compounds that inhibit or display antagonism towards E-selectin without displaying substantial inhibition or antagonism towards another selectin (e.g., P-selectin). Accordingly, a compound that is selective for E-selectin exhibits an E-selectin selectivity of greater than about 2-fold, 5-fold, 10-fold, 20-fold, 50-fold or greater than about 100-fold with respect to inhibition or antagonism of another selectin (i.e., a selectin other than E-selectin). In some embodiments, selective compounds display at least 50-fold greater inhibition or antagonism towards E-selectin than towards P-selectin. In still other embodiments, selective compounds inhibit or display at least 100-fold greater inhibition or antagonism towards E-selectin than towards P-selectin. In still other embodiments, selective compounds display at least 500-fold greater inhibition or antagonism towards E-selectin than towards P-selectin. In still other embodiments, selective compounds display at least 1000-fold greater inhibition or antagonism towards E-selectin than towards P-selectin.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by an appropriate method. For example, sequence identity analysis may be carried out using the DNASIS computer program (Version 2.5 for windows; available from Hitachi Software engineering Co., Ltd., South San Francisco, Calif., USA) using standard defaults as used in the reference manual accompanying the software.

"Similarity" refers to the percentage number of amino acids that are identical or constitute conservative substitutions as defined in Table A below. Similarity may be determined using sequence comparison programs such as GAP (Deveraux et al. 1984, Nucleic Acids Research 12, 387-395). In this way, sequences of a similar or substantially different length to those cited herein might be compared by insertion of gaps into the alignment, such gaps being determined, for example, by the comparison algorithm used by GAP. Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology", John Wiley & Sons Inc, 1994-1998, Chapter 15.

"Stringency" as used herein refers to the temperature and ionic strength conditions, and presence or absence of certain organic solvents, during hybridization. The higher the stringency, the higher will be the observed degree of complementarity between sequences. "Stringent conditions" as used herein refers to temperature and ionic conditions under which only polynucleotides having a high proportion of complementary bases, preferably having exact complementarity, will hybridize. The stringency required is nucleotide sequence dependent and depends upon the various components present during hybridization, and is greatly changed when nucleotide analogues are used. Generally, stringent conditions are selected to be about 10° C. to 20° C. less than the thermal melting point (Tm) for the specific sequence at a defined ionic strength and pH. The Tm is the temperature (under defined ionic strength and pH) at which 50% of a target sequence hybridizes to a complementary probe. It will be understood that a polynucleotide will hybridize to a target sequence under at least low stringency conditions, preferably under at least medium stringency conditions and more preferably under high stringency conditions. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at room temperature. Medium stringency conditions include and encompass from at least about 16% v/v to at least about 30% v/v formamide and from at least about 0.5 M to at least about 0.9 M salt for hybridization at 42° C., and at least about 0.5 M to at least about 0.9 M salt for washing at 42° C. Medium stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at 42° C. High stringency conditions include and encompass from at least about 31% v/v to at least about 50% v/v formamide and from at least about 0.01 M to at least about 0.15 M salt for hybridization at 42° C., and at least about 0.01 M to at least about 0.15 M salt for washing at 42° C. High stringency conditions also may include 1% BSA, 1 mM EDTA, 0.5 M NaHPO4 (pH 7.2), 7% SDS for hybridization at 65° C., and (i) 0.2×SSC, 0.1% SDS; or (ii) 0.5% BSA, 1 mM EDTA, 40 mM NaHPO4 (pH 7.2), 1% SDS for washing at a temperature in excess of 65° C. Other stringent conditions are well known in the art. A skilled addressee will recognize that various factors can be manipulated to optimize the specificity of the hybridization. Optimization of the stringency of the final washes can serve to ensure a high degree of hybridization. For detailed examples, see CURRENT PROTOCOLS 1N MOLECULAR BIOLOGY (supra) at pages 2.10.1 to 2.10.16 and MOLECULAR CLONING. A LABORATORY MANUAL (Sambrook, et al., eds.) (Cold Spring Harbor Press 1989) at sections 1.101 to 1.104.

"Subjects" contemplated in the present invention include any animal of commercial humanitarian or epidemiological interest including conveniently, primates, livestock animals (such as sheep, cows, horses, donkeys, pigs, fish and birds), laboratory test animals (such as mice, rabbits, guinea pigs and hamsters and the like), companion animals (such as dogs and cats), or captive wild animals. Avian species include poultry birds and caged avian species. In some embodiments the subject is a mammalian animal. In other embodiments, the subject is a human subject. The present composition and methods have applications in human and veterinary medicine, domestic or wild animal husbandry, cosmetic or aesthetic treatments for the skin after injury or surgery.

By "substantially complementary" it is meant that an oligonucleotide or a subsequence thereof is sufficiently complementary to hybridize with a target sequence. Accordingly, the nucleotide sequence of the oligonucleotide or subsequence need not reflect the exact complementary sequence of the target sequence. In a preferred embodiment, the oligonucleotide contains no mismatches and with the target sequence.

A "thrombocytopenia medicament" as used herein refers to a composition of matter which reduces the symptoms related to thrombocytopenia, prevents the development of thrombocytopenia, or treats existing thrombocytopenia.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

Reference herein to "a virus" includes any virus or viral pathogen or emerging viral pathogen. Viral families contemplated include Adenoviridae, African swine fever-like viruses, Arenaviridae (such as viral haemorrhagic fevers, Lassa fever), Astroviridae (astroviruses) Bunyaviridae (La Crosse), Caliciviridae (Norovirus), Coronaviridae (Corona virus), Filoviridae (such as Ebola virus, Marburg virus), Parvoviridae (B19 virus), Flaviviridae (such as hepatitis C virus, Dengue viruses), Hepadnaviridae (such as hepatitis B virus, Deltavirus), Herpesviridae (herpes simplex virus, varicella zoster virus), Orthomyxoviridae (influenza virus) Papovaviridae (papilloma virus) Paramyxoviridae (such as human parainfluenza viruses, mumps virus, measles virus, human respiratory syncytial virus, Nipah virus, Hendra virus), Picornaviridae (common cold virus), Poxyiridae (small pox virus, orf virus, monkey poxvirus) Reoviridae (rotavirus) Retroviridae (human immunodeficiency virus) Parvoviridae (parvoviruses) Papillomaviridae, (papillomaviruses) alphaviruses and Rhabdoviridae (rabies virus).

As used herein, underscoring or italicizing the name of a gene shall indicate the gene, in contrast to its protein product, which is indicated by the name of the gene in the absence of any underscoring or italicizing. For example, "E-selectin" shall mean the E-selecting gene, whereas "E-selectin" shall indicate the protein product or products generated from transcription and translation and alternative splicing of the "E-selectin" gene.

2. Compositions and Methods for the Treatment or Prophylaxis of Immunocompromised Conditions Resulting from Medical Treatment The present invention is based in part on the surprising discovery that the absence of E-selectin at the endothelial niche significantly delays hematopoietic stem cell turnover. Based on this finding, the present inventors propose that E-selectin antagonists are useful in methods and compositions for reducing hematopoietic stem cell turnover, thereby rendering the treated hematopoeitic stem cells resistant to medical treatments, especially those that target rapidly dividing cells or that disrupt the cell cycle or cell division. The methods and compositions of the present invention are thus particularly useful in the treatment or prophylaxis of immunocompromised conditions resulting from such medical treatments.

Accordingly, in some embodiments, the present invention provides methods for treating or preventing immunocompromised conditions resulting from a medical treatment (e.g., chemotherapy and/or radiation treatment), wherein the methods generally comprise administering to an individual having, or at risk of developing, the immunocompromised condition, an effective amount of an E-selectin antagonist, which is suitably in the form of a pharmaceutical composition. In accordance with the present invention, the E-selectin antagonist can act to prevent or attenuate hematopoietic disorders including, but not limited to, neutropenia, agranulocytosis, thrombocytopenia, and anemia.

The E-selectin antagonist includes and encompasses any active compound that binds to E-selectin and that suitably inhibits the functional activity of E-selectin, including small molecules, such as nucleic acids, peptides, polypeptides, peptidomimetics, carbohydrates, lipids or other organic (carbon containing) or inorganic molecules. In some embodiments, the E-selectin antagonist is selected from antigen-binding molecules that are immuno-interactive with E-selectin, peptides that bind to E-selectin and that block cell-cell adhesion, as well as carbohydrate or peptide mimetics of E-selectin ligands. In some embodiments, the E-selectin antagonist reduces the expression of an E-selectin gene or the level or functional activity of an expression product of that gene. For example, the E-selectin antagonist may antagonize the function of E-selectin, including reducing or abrogating the activity of at least one of its ligand-binding sites. Alternatively, the E-selectin antagonist may act indirectly on E-selectin expression by modulating the level or functional activity of a regulator of E-selectin. For example, it is known that cytokine-dependent induction of E-selectin expression is mediated through cooperative signaling involving the Ras/Raf protein kinase pathway and that inhibition of C-raf antisense molecules can block E-selectin expression and E-selectin mediated cell-cell adhesion.

Illustrative agents for reducing or abrogating gene expression include, but are not restricted to, oligoribonucleotide sequences, including anti-sense RNA and DNA molecules and ribozymes, that function to inhibit the translation, for example, of E-selectin-encoding transcripts including E-selectin mRNA. Representative transcripts of this type include:

nucleotide sequences that comprise the sequence:

[SEQ ID NO: 1]
```
atgattgcttcacagtttctctcagctctcactttggtgcttctcattaaagaga
gtggagcctggtattacaacacctccacggaagctatgacttatgatgaggccagtgcttattgtcag
caaaggtacacacacctggttgcaattcaaaacaaagaagagattgagtacctaaactccatattgag
ctattcaccaagttattactggattggaatcagaaaagtcaacaatgtgtgggtctgggtaggaaccc
agaaacctctgacagaagaagccaagaactgggctccaggtgaacccaacaataggcaaaaagatgag
gactgcgtggagatctacatcaagagagaaaaagatgtgggcatgtggaatgatgagaggtgcagcaa
gaagaagattgccctatgctacacagctgcctgtaccaatacatcctgcagtggccacggtgaatgtg
tagagaccatcaataattacacttgcaagtgtgaccctggcttcagtggactcaagtgtgagcaaatt
gtgaactgtacagcactggaatccctgagcatggaagcctggtttgcagtcacccactgggaaactt
cagctacaattcttcatgctctatcagctgtgatagggggttacctgccaagcagcatggagaccatgc
agtgtatgtcctctggagaatggagtgctactattccagcctgcaatgtggttgagtgtgatgctgtg
acaaatccagccaatgggttcgtggaatgtttccaaaaccatggaagcttaccatggaacacaacctg
tacatttgactgtgaagaaggatttgaactaatgggagcccagagccttcagtgtacctcatctggga
attgggacaacgagaagccaacgtgtaaagctgtgacatgcagggccgtacgccagcctcagaatggc
tctgtgaggtgcagccattccctgctggagagttcaccttcaaatcatcctgcaacttcacctgtga
ggaaggcttcatgttgcagggaccagcccaggttgaatgcaccactcaagggcagtggacacagcaaa
tcccagtttgtgaagctttccagtgcacagccttgtccaaccccgagcgaggctacatgaattgtctt
cctagtgcttctggcagtttccgttatgggtccagctgtgagttctcctgtgagcagggttttgtgtt
gaagggatccaaaaggctccaatgtggacccacagggggagtgggacaacgagaagcccacatgtgaag
ctgtgagatgcgatgatgtccaccagcccccgaagggtttggtgaggtgtgctcattccactattgga
gaattcacctacaagtcctcttgtgccttcagctgtgaggagggatttgaattacatggatcaactca
acttgagtgcacatctcagggacaatggacagaagaggttccttcctgccaagtggtaaaatgttcaa
gcctggcagttccgggaaagatcaacatgagctgcagtggggagcccgtgtttggcactgtgtgcaag
ttcgcctgtcctgaaggatggacgctcaatggctctgcagctcggacatgtggagccacaggacactg
gtctggcctgctacctacctgtgaagctcccactgagtccaacattcccttggtagctggactttctg
ctgctggactctccctcctgacattagcaccatttatcctctggcttcggaaatgcttacggaaagca
aagaaatttgttcctgccagcagctgccaaagccttgaatcagatggaagctaccaaaagccttctta
catcctttaa;
``` nucleotide sequences that share at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity with SEQ ID NO: 1;

nucleotide sequences that hybridize under at least low, medium or high stringency conditions to SEQ ID NO: 1;

nucleotide sequences that encode the amino acid sequence:

[SEQ ID NO: 2]

```
MIASQFLSALTLVLLIKESGAWSYNTSTEAMTYDEASAYCQQRYTHLVAIQNKEE

IEYLNSILSYSPSYYWIGIRKVNNVWVWVGTQKPLTEEAKNWAPGEPNNRQKDEDCVEIYIKREKDVG

MWNDERCSKKKLALCYTAACTNTSCSGHGECVETINNYTCKCDPGFSGLKCEQIVNCTALESPEHGSL

VCSHPLGNFSYNSSCSISCDRGYLPSSMETMQCMSSGEWSAPIPACNVVECDAVTNPANGFVECFQNP

GSFPWNTTCTFDCEEGFELMGAQSLQCTSSGNWDNEKPTCKAVTCRAVRQPQNGSVRCSHSPAGEFTF

KSSCNFTCEEGFMLQGPAQVECTTQGQWTQQIPVCEAFQCTALSNPERGYMNCLPSASGSFRYGSSCE

FSCEQGFVLKGSKRLQCGPTGEWDNEKPTCEAVRCDAVHQPPKGLVRCAHSPIGEFTYKSSCAFSCEE

GFELHGSTQLECTSQGQWTEEVPSCQVVKCSSLAVPGKINMSCSGEPVFGTVCKFACPEGWTLNGSAA

RTCGATGHWSGLLPTCEAPTESNIPLVAGLSAAGLSLLTLAPFLLWLRKCLRKAKKFVPASSCQSLES

DGSYQKPSYIL;
``` nucleotide sequences that encode an amino acid sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence similarity with SEQ ID NO: 2; and nucleotide sequences that encode an amino acid sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity with SEQ ID NO: 2.

Anti-sense RNA and DNA molecules act to directly block the translation of mRNA by binding to targeted mRNA and preventing protein translation. In regard to antisense DNA, oligodeoxyribonucleotides derived from the translation initiation site, e.g., between – and + regions are preferred.

In some embodiments, anti-sense RNA and DNA molecules are used to directly block the translation of E-selectin mRNA by binding to targeted mRNA and preventing protein translation. In regard to antisense DNA, oligodeoxyribonucleotides derived from the translation initiation site, e.g., between −10 and +10 regions are desirable. Illustrative E-selectin antisense molecules are described, for example, by Bennett et al. (1994, J. Immunol., 152(7): 3530-3540) and by Baker et al. (U.S. Pat. No. 5,789,573). In other embodiments, C-raf antisense molecules can be used, which block C-raf expression, leading to reduced or abrogated E-selectin expression, as disclosed for example by Khatib et al. (2002, Cancer Res. 62(19):5393-5398).

In other embodiments, anti-E-selectin ribozymes are used for catalyzing the specific cleavage of E-selectin RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyse endonucleolytic cleavage of target sequences. Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' or 3' ends of the molecule or the use of phosphorothioate or 2'O-methyl rather than phosphodiesterase linkages within the oligodeoxyribonucleotide backbone.

In other embodiments, RNA molecules that mediate RNA interference (RNAi) of an E-selectin gene or E-selectin transcript can be used to reduce or abrogate gene expression. RNAi refers to interference with or destruction of the product of a target gene by introducing a single stranded, and typically a double stranded RNA (dsRNA) that is homologous to the transcript of a target gene. Thus, in some embodiments, dsRNA per se and especially dsRNA-producing constructs corresponding to at least a portion of an E-selectin gene may be used to reduce or abrogate its expression. RNAi-mediated inhibition of gene expression may be accomplished using any of the techniques reported in the art, for instance by transfecting a nucleic acid construct encoding a stem-loop or hairpin RNA structure into the genome of the target cell, or by expressing a transfected nucleic acid construct having homology for an E-selectin gene from between convergent promoters, or as a head to head or tail to tail duplication from behind a single promoter. Any similar construct may be used so long as it produces a single RNA having the ability to fold back on itself and produce a dsRNA, or so long as it produces two separate RNA transcripts which then anneal to form a dsRNA having homology to a target gene.

Absolute homology is not required for RNAi, with a lower threshold being described at about 85% homology for a dsRNA of about 200 base pairs (Plasterk and betting, 2000, *Current Opinion in Genetics and Dev.* 10: 562-67). Therefore, depending on the length of the dsRNA, the RNAi-encoding nucleic acids can vary in the level of homology they contain toward the target gene transcript, i.e., with dsRNAs of 100 to 200 base pairs having at least about 85% homology with the target gene, and longer dsRNAs, i.e., 300 to 100 base pairs, having at least about 75% homology to the target gene. RNA-encoding constructs that express a single RNA transcript designed to anneal to a separately expressed RNA, or single constructs expressing separate transcripts from convergent promoters, are suitably at least about 100 nucleotides in length. RNA-encoding constructs that express a single RNA designed to form a dsRNA via internal folding are usually at least about 200 nucleotides in length.

The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors.

In other embodiments, RNA molecules of about 21 to about 23 nucleotides, which direct cleavage of specific mRNA to which they correspond, as for example described by Tuschl et al. in U.S. Patent Application Publication No. 20020086356, can be utilised for mediating RNAi. Such 21-23 nt RNA molecules can comprise a 3' hydroxyl group, can be single-stranded or double stranded (as two 21-23 nt RNAs) wherein the dsRNA molecules can be blunt ended or comprise overhanging ends (e.g., 5', 3').

Illustrative RNAi molecules are commercially available from Santa Cruz Biotechnology, Inc. (Santa Cruz, Calif., USA).

In still other embodiments, the functional activity of an E-selectin polypeptide in the cell is inhibited through use of an anti-E-selectin antigen-binding molecule (e.g., a neutralising antibody) as described for example by Owens et al. in U.S. Pat. No. 6,407,214 or by Sanz et al. (2007, Br 3 Pharmacol. 152(4): 481-492). A range of anti-E-selectin antibodies is available commercially, for example from Abeam (Cambridge, UK), Beckman Coulter (Fullerton, Calif., USA), Bender MedSystems (Vienna, Austria), BioGenex (San Ramon, Calif., USA), Biomeda Corporation (Foster City, Calif., USA), BioVision, Inc. (Mountain View, Calif., USA), Cell Sciences (Canton, Mass., USA), Covance Research Products (Denver, Pa., USA), Celltech Chirosci-ence (Slough, UK; CDP850 humanized monoclonal antibody against E-selectin), GeneTex (San Antonio, Tex., USA), Hycult Biotechnology BV (Uden, The Netherlands), Protein Design Labs (Freemont, Calif., USA; SMART HuEP57C humanized monoclonal antibody), and R&D Systems (Minneapolis, Minn., USA).

In some embodiments, the E-selectin antagonist is selected from peptide inhibitors of E-selectin. Representative inhibitors of this type are disclosed, for example, by Cwirla et al. in International Publication WO 94/25043, which is expressly incorporated herein by reference in its entirety, and include peptides of from 9 to 20 amino acids having a core structure comprising:

WXXLWXXX' [SEQ ID NO: 3] where each amino acid is indicated by the one-letter amino acid code where specifically W is tryptophan, L is leucine, and X is any amino acid and X' is selected from the group consisting of M and Nle where M is methionine and Nle is norleucine. Specific peptides having this core structure comprise the sequence $X_1X_2X_3WX_4X_5LWX_6X_7X_8X_9$ [SEQ ID NO: 4], wherein each residue can be independently selected as follows: X is H, E, or D; $X_2$ is I, M, or Nie; $X_3$ is T or S; $X_4$ is D, E, or L; $X_5$ is Q or E; X* is N or D; $X_7$ is L, M, V, or I; $X_s$ is M or Nle; and X, is N, S, Q.

In specific embodiments, the peptides are selected from the following sequences:

| | |
|---|---|
| DGDITWDQLWDLMK; | [SEQ ID NO: 5] |
| DYTWFELWDMMQ; | [SEQ ID NO: 6] |
| DITWDELWKIMN; | [SEQ ID NO: 7] |
| QITWAQLWNMMK; | [SEQ ID NO: 8] |
| DYSWHDLWEMMS; | [SEQ ID NO: 9] |
| DITWDQLWDLNleK; | [SEQ ID NO: 10] |
| HITWDQLWRIMT; | [SEQ ID NO 11] |
| d-DITWDQLWDLMK; | [SEQ ID NO: 12] |
| Dd-ITWDQLWDLMK; | |
| DId-TWDQLWDLMK; | |
| DITWd-DQLWDLMK; | |
| DITWDQLWDd-LMK; | |
| DITWDQLWDLMd-K; and | |
| HITWDQLWNVMN; | |
| ITWDQLWDLMK; (amino acids 4-14 of SEQ ID NO: 5) | |
| DITWDQLWDLMK; (amino acids 3-14 of SEQ ID NO: 5) | |
| DGDTTWDQLWDLMK | [SEQ ID NO: 13] |
| DYTWFELWDMMQ; | [SEQ ID NO: 14] |
| DITWDELWKIMN; | [SEQ ID NO: 15] |
| QITWAQLWNMMK; | [SEQ ID NO: 16] |
| DYSWHDLWEMMS; | [SEQ ID NO: 17] |
| DITWDQLWDLNleK; | [SEQ ID NO: 18] |
| ATTWDQLWLLMS; | [SEQ ID NO: 19] |
| ELTWDQLWVLMS; | [SEQ ID NO: 20] |
| DVTWDQLWELMT; | [SEQ ID NO: 21] |
| EVTWDQLWVMMQ; | [SEQ ID NO: 22] |

-continued

| | |
|---|---|
| NLTWDQLWVLMS; | [SEQ ID NO: 23] |
| EMSWLELWNVMN; | [SEQ ID NO: 24] |
| TITWDQLWQMMS; | [SEQ ID NO: 25] |
| ELSWDQLWNVMN; | [SEQ ID NO: 26] |
| EMTWQELWNVMN; | [SEQ ID NO: 27] |
| EMTWTELWNVMN; | [SEQ ID NO: 28] |
| DMTWSQLWNVMN; | [SEQ ID NO: 29] |
| EMTWLGLWNVMN; | [SEQ ID NO: 30] |
| QITWMELWNLMN; | [SEQ ID NO: 31] |
| ETTWDQLWEVMN; | [SEQ ID NO: 32] |
| ETTWDQLWDVMN; | [SEQ ID NO: 33] |
| DISWDQLWNVMN; | [SEQ ID NO: 34] |
| QITWDQLWDLMK; | [SEQ ID NO: 35] |
| EMTWDQLWNVMN; | [SEQ ID NO: 36] |
| DITWDQLWNMMD; | [SEQ ID NO: 37] |
| DITWNMLWNMMQ; | [SEQ ID NO: 38] |
| DISWDDLWIMMN; | [SEQ ID NO: 39] |
| DITWHQLWNLMN; | [SEQ ID NO: 40] |
| EISWEQLWTMMN; | [SEQ ID NO: 41] |
| DITWEQLWNMMN; | [SEQ ID NO: 42] |
| EITWDQLWTLMT; | [SEQ ID NO: 43] |
| DITWHQLWNLMN; | [SEQ ID NO: 44] |
| DMTWDQLWIVMN; | [SEQ ID NO: 45] |
| DITWEQLWNLMN; | [SEQ ID NO: 46] |
| QITWYQLWNMMN; | [SEQ ID NO: 47] |
| HISWHELWNLMQ; | [SEQ ID NO: 48] |
| YTTWEQLWTMMN; | [SEQ ID NO: 49] |
| HITWDQLWDLMQ; | [SEQ ID NO: 50] |
| QITWDQLWDLMY; | [SEQ ID NO: 51] |
| QITWDQLWNMMI; | [SEQ ID NO: 52] |
| YITWEQLWNMMN; | [SEQ ID NO: 53] |
| HITWDQLWDTMS; | [SEQ ID NO: 54] |
| HITWDQLWEIMS; | [SEQ ID NO: 55] |
| HITWDQLWALMT; | [SEQ ID NO: 56] |
| HITWDQLWSLMS; | [SEQ ID NO: 57] |
| HITWDQLWLMMS; | [SEQ ID NO: 58] |
| HITWDQLWDLMQ; | [SEQ ID NO: 59] |
| HITWDQLWWTMA; | [SEQ ID NO: 60] |
| HITWDQLWLLMA; | [SEQ ID NO: 61] |
| HITWDQLWMLMA; | [SEQ ID NO: 62] |
| GSDSHTTWDELWNLMNPVLA; | [SEQ ID NO: 63] |

-continued

| | |
|---|---|
| NWLDDITWDELWKIMNPSTA; | [SEQ ID NO: 64] |
| ETDDHITWDQLWRTMTATMA; | [SEQ ID NO: 65] |
| WTDTHITWDQLWHFMNMGEQ; | [SEQ ID NO: 66] |
| GFGEAITWDQLWDMMNGEDA; | [SEQ ID NO: 67] |
| NVAEQITWDQLWNLMSVGSS; | [SEQ ID NO: 68] |
| GQTGLITWDMLWNLMNPVGE; | [SEQ ID NO: 69] |
| GTGDHITWDQLWNLMINEKG; | [SEQ ID NO: 70] |
| EYGRHITWDQLWQLMQSATA; | [SEQ ID NO: 71] |
| MNNWHVSWEQLWDIMNGPPN; | [SEQ ID NO: 72] |
| ESASHITWGQLWDLMNASEV; | [SEQ ID NO: 73] |
| YWRGNITWDQLWNIMNSEYS; | [SEQ ID NO: 74] |
| AGASHITWAQLWNMMNGNEG; | [SEQ ID NO: 75] |
| GSWAHITWDQLWNLMNMGTQ; | [SEQ ID NO: 76] |
| YGNSNITWDQLWSTMNRQTT; | [SEQ ID NO: 77] |
| AHLPHISWDTLWHIMNKGEK; | [SEQ ID NO: 78] |
| ESASHITWGQLWDLMNASEV; | [SEQ ID NO: 79] |
| MNNWHVSWEQLWDIMNGPPN; | [SEQ ID NO: 80] |
| GFGEAITWDQLWDMMNGEDA; | [SEQ ID NO: 81] |
| WTDTHITWDQLWHFMNMGEQ; | [SEQ ID NO: 82] |
| EMTWAELWTLME; | [SEQ ID NO: 83] |
| DISWRQLWDIMN; | [SEQ ID NO: 84] |
| EISWLGLWDIMN; | [SEQ ID NO: 85] |
| DMTWHDLWTLMS; | [SEQ ID NO: 86] |
| RGVWGGLWSMTW; | [SEQ ID NO: 87] |
| EMTWQQLWWMQ; | [SEQ ID NO: 88] |
| AEWTWDQLWHVMNPAESQ; | [SEQ ID NO: 89] |
| RNMSWLELWEHMK; | [SEQ ID NO: 90] |
| SQVTWNDLWSVMNPEVVN; | [SEQ ID NO: 91] |
| HRAEWLALWEQMSP; | [SEQ ID NO: 92] |
| YKKEWLELWHQMQA; | [SEQ ID NO: 93] |
| RSLSWLQLWDQMK; | [SEQ ID NO: 94] |
| KEQQWRNLWKMMS; | [SEQ ID NO: 95] |
| KKEDWLALWRIMSVPD; | [SEQ ID NO: 96] |
| RNMSWLELWEHMK; | [SEQ ID NO: 97] |
| GRPTWNELWDMMQAP; | [SEQ ID NO: 98] |
| KRKQWIELWNIMS; | [SEQ ID NO: 99] |
| KTSEWNNLWKLMSQ | [SEQ ID NO: 100] |
| HVSWEQLWDIMN | [SEQ ID NO: 101] |
| KKEDWLALWRIMSV; | [SEQ ID NO: 102] |
| HRAEWLALWEQMS; | [SEQ ID NO: 103] |

```
DGDITWDQLWDLNleK;          [SEQ ID NO: 104]

QITWDQLWDLNleK;            [SEQ ID NO: 105]

AETWDQLWHVMNPAESQ;         [SEQ ID NO: 106]

DITWAQLWNNleNleN;          [SEQ ID NO: 107]
and

DITWDQLWDLM;               [SEQ ID NO: 108]
(amino acids 3-13 of
SEQ ID NO: 5)

DITWDQLWDL
(amino acids 3-12 of
SEQ ID NO: 5);

TWDQLWDLMK
(amino acids 5-14 of
SEQ ID NO: 5);
and

DITWDQLWDLMK-C(O)NH2
(amino acids 3-14 of
SEQ ID NO: 5)
wherein d-indicates a D-amino
acid and -C(O)NH2
represents an amidated
carboxy terminus.
```

Alternative peptide inhibitors of E-selectin can be selected from those disclosed by Barrett et al. in International Publication WO 95/31210, which is expressly incorporated herein by reference in its entirety, and which include peptides and peptide mimetics comprising: a molecular weight of less than about 2000 daltons, and a binding affinity to E-selectin as expressed by an $IC_{50}$—HL6O of no more than about 100 μM wherein from zero to all of the —C(O)NH— linkages of the peptide have been replaced by a linkage selected from the group consisting of a —CH$_2$OC(O)NR— linkage, a phosphonate linkage, a —CH$_2$S(O)$_2$N— linkage, a —CH$_2$NR— linkage, a —C(O)NR$^6$— linkage, and a —NHC(O)NH— linkage where R is hydrogen or lower alkyl, and R$^6$ is lower alkyl, further wherein the N-terminus of said peptide or peptide mimetic is selected from the group consisting of a —NRR$^1$ group, a —NRC(O)R group, a —NRC(O)OR group, a —NRS(O)$_2$R group, a —NHC(O)NHR group, a succinimide group, a benzyloxycarbonyl-NH— group, and a benzyloxycarbonyl-NH— group having from 1 to 3 substituents on the phenyl ring selected from the group consisting of lower alkyl, lower alkoxy, chloro, and bromo, where R and R$^1$ are independently selected from the group consisting of hydrogen and lower alkyl, and still further wherein the C-terminus of said peptide or peptide mimetic has the formula —C(O)R$^2$ where R$^2$ is selected from the group consisting of hydroxy, lower alkoxy, and —NR$^3$R$^4$ where R$^3$ and R$^4$ are independently selected from the group consisting of hydrogen and lower alkyl and where the nitrogen atom of the —NR$^3$R$^4$ group can optionally be the amine group of the N-terminus of the peptide so as to form a cyclic peptide and physiologically acceptable salts thereof.

Representative peptides and peptide mimetics disclosed in WO 95/31210 include peptides which comprise the following sequences:

```
YDDVCCELLF;                    [SEQ ID NO: 109]

DLPQWYTEWC;                    [SEQ ID NO: 110]

ENSHWCTCPC;                    [SEQ ID NO: 111]

DIEQDWVTWM;                    [SEQ ID NO: 112]

NEWCWPCRL;                     [SEQ ID NO: 1113]

DIWQDWVRWM;                    [SEQ ID NO: 114]

DLWQDWVTWM;                    [SEQ ID NO: 115]

DLWQDWVHWM;                    [SEQ ID NO: 116]

DIWQDWVTWM;                    [SEQ ID NO: 117]

DIWQDWVKWM                     [SEQ ID NO: 118]

DIWQDWVRWM-C(O)NH2;            [SEQ ID NO: 119]

DIWEDWVRWM;                    [SEQ ID NO: 120]

DIWQDWTTWM;                    [SEQ ID NO: 121]

DITNal(1)DQLWDLMK-C(O)NH2;     [SEQ ID NO: 122]

DITWDQLNal(1)DLMK-C(O)NH2;     [SEQ ID NO: 123]

DITNal(2)DQLWDLMK-C(O)NH2;     [SEQ ID NO: 124]

DITWDQLNal(2)DLMK-C(O)NH2;     [SEQ ID NO: 125]

DITChaDQLWbLMK-C(O)NH2;        [SEQ ID NO: 126]

DITWDQLChaDLMK-C(O)NH2;        [SEQ ID NO: 127]

DITWDQLWDLM(OCH3)K-C(O)NH2;    [SEQ ID NO: 128]

DITWDQLWDLM(SOCH3)K-C(O)NH2;   [SEQ ID NO: 129]

DITWDQLWDLM(SO2CH3)K-C(O)NH2;  [SEQ ID NO: 130]

DITWDQLW-Aib-LMK-C(O)NH2;      [SEQ ID NO: 131]

DITWDQLW-Aib-LMK;              [SEQ ID NO: 132]

DITW-Aib-QLWKLMK;              [SEQ ID NO: 133]

DITW-Aib-QLWDLMK-C(O)NH2;      [SEQ ID NO: 134]

DITW-Aib-QLW-Aib-LMK-C(O)NH2;  [SEQ ID NO: 135]

DITW-Aib-QLWDLMK;              [SEQ ID NO: 136]

DITW-Aib-QLW-Aib-LMK;          [SEQ ID NO: 137]
```

AITWDQLWDLNleK; [SEQ ID NO: 138]

DATWDQLWDLNleK; [SEQ ID NO: 139]

DITADQLWDLNleK; [SEQ ID NO: 140]

DITWAQLWDLNleK; [SEQ ID NO: 141]

DITWDALWDLNleK; [SEQ ID NO: 142]

DITWDQAWDLNleK; [SEQ ID NO: 143]

DITWDQLADLNleK; [SEQ ID NO: 144]

DITWDQLWALNleK; [SEQ ID NO: 145]

DITWDQLWDANleK; [SEQ ID NO: 146]

DITWDQLWDLAK; [SEQ ID NO: 147]

DITWDQLWDLNleA; [SEQ ID NO: 148]

DITNal(1)DQLNal(1)DLMK-C(O)NH$_2$; [SEQ ID NO: 149]

DITWAQLNal(1)DLMK-C(O)NH$_2$; [SEQ ID NO: 150]

DITNal(1)AQLNal(1)DLMK-C(O)NH$_2$; [SEQ ID NO: 151]

DITNal(1)AQLNal(1)DLM(OCH$_3$)K-C(O)NH$_2$; [SEQ ID NO: 152]

DITWAQLWDLM(SO$_2$CH$_3$)K-C(O)NH$_2$; [SEQ ID NO: 153]

DITWAQLNal(1)DLM(SO$_2$CH$_3$)K-C(O)NH$_2$; [SEQ ID NO: 154]

DITNal(1)AQLWDLM(SO$_2$CH$_3$)K-C(O)NH$_2$; [SEQ ID NO: 155]

DITWAQLWDLM(OCH$_3$)K-C(O)NH$_2$; [SEQ ID NO: 156]

DITNal(1)AQLWDLMK-C(O)NH$_2$; [SEQ ID NO: 157]

DITNal(1)DQLWDLM(SO$_2$CH$_3$)K-C(O)NH$_2$; [SEQ ID NO: 158]

DITWDQLNal(1)DLM(SO$_2$CH$_3$)K-C(O)NH$_2$; [SEQ ID NO: 159]

DITWAQLWDLMK-C(O)NH$_2$; [SEQ ID NO: 160]

DITWAibQLWDLMK-C(O)NH$_2$; [SEQ ID NO: 161]

Ac-DITWDQLWKLMK; [SEQ ID NO: 162]

Ac-DITWDQLWDL-Nle-K-C(O)NH$_2$; [SEQ ID NO: 163]

Succ-ITWDQLWDLMK; [SEQ ID NO: 164]

Cbz-TWDQLWDLMK; [SEQ ID NO: 165]

Succ-ITWDQLWDLMK-C(O)NH$_2$; [SEQ ID NO: 166]

Cbz-DITWDQLWDLMK-C(O)NH$_2$; [SEQ ID NO: 167]

Ac-DITWDQLWDLMK-C(O)NH$_2$; [SEQ ID NO: 168]

Cbz-ITWDQLWDLMK; [SEQ ID NO: 169]

Succ-ITWDQLWAibLM(SO$_2$CH$_3$)K-C(O)NH$_2$; [SEQ ID NO: 170]

Succ-ITWAQLWAibLM(SO$_2$CH$_3$)K-C(O)NH$_2$; [SEQ ID NO: 171]

Succ-ITWAQLWDLM(SO$_2$CH$_3$)K-C(O)NH$_2$; [SEQ ID NO: 172]

Succ-rrWAQLWDLM(OCH$_3$)K-C(O)NH$_2$; [SEQ ID NO: 173]

Succ-ITWAQLWAibLM(OCH$_3$)K-C(O)NH$_2$; [SEQ ID NO: 174]

Succ-ITWDQLWAibLM(OCH$_3$)K-C(O)NH$_2$; [SEQ ID NO: 175]

Ac-DITWAQLWDLMK-C(O)NH$_2$; [SEQ ID NO: 176]

Ac-DITWDQLWAibLM(OCH$_3$)K-C(O)NH$_2$; [SEQ ID NO: 177]

Ac-DITWAQLWAibLM(SO$_2$CH$_3$)K-C(O)NH$_2$; [SEQ ID NO: 178]

Ac-DITWDQLWAibLM(SO$_2$CH$_3$)K-C(O)NH$_2$; [SEQ ID NO: 179]

Ac-DITWAQLWDLM(SO$_2$CH$_3$)K-C(O)NH$_2$; [SEQ ID NO: 180]

Ac-DITWAQLWDLM(OCH$_3$)K-C(O)NH$_2$; [SEQ ID NO: 181]

Ac-DITWAQLWAibLM(OCH$_3$)K-C(O)NH$_2$; [SEQ ID NO: 182]

Ac-DITWDQLWAibLM(OCH$_3$)K-C(O)NH$_2$; [SEQ ID NO: 183]

DITWAQLWAibLM(OCH$_3$)K-C(O)NH$_2$; [SEQ ID NO: 184]

DITWAQLWAibLM(SO$_2$CH$_3$)K-C(O)NH$_2$; [SEQ ID NO: 185]

DITWDQLWAibLM(OCH$_3$)K-C(O)NH$_2$; [SEQ ID NO: 186]

WDLMK-C(O)NH$_2$; [SEQ ID NO: 187]

Cbz-WDLM-C(O)NH$_2$; [SEQ ID NO: 188]

Cbz-QLWD-C(O)NH$_2$; [SEQ ID NO: 189]

Cbz-QLWDLM-C(O)NH$_2$; [SEQ ID NO: 190]

Cbz-ITWDQ-C(O)NH$_2$; [SEQ ID NO: 191]

```
Cbz-TWDQLW-C(O)NH₂;                                [SEQ ID NO: 192]

Cbz-WDQLWD-C(O)NH₂;                                [SEQ ID NO: 193]

Cbz-ITWAQ-C(O)NH₂;                                 [SEQ ID NO: 194]

Cbz-ITWDQL-C(O)NH₂;                                [SEQ ID NO: 195]

N-Cbz, N-Me-ITW-C(O)NH₂;                           [SEQ ID NO: 196]

Cbz-rr-[(Me)(DL)W]-C(O)NH₂;                        [SEQ ID NO: 197]

N-Cbz, N-Me-ITWDQ-C(O)NH₂;                         [SEQ ID NO: 198]

Cbz-ITW-N-Me-DQ-C(O)NH₂;                           [SEQ ID NO: 199]

Cbz-rr-N-Me-WDQ-C(O)NH₂;                           [SEQ ID NO: 200]

Cbz-I-(N-Me T)WDQ-C(O)NH₂;                         [SEQ ID NO: 201]

Cbz-I-(N-Me-T)W-C(O)NH₂;                           [SEQ ID NO: 202]

Cbz-IT-[(aMe)(DL)W]-DQ-C(O)NH₂;                    [SEQ ID NO: 203]

Cbz-N-Me-I-T-[(aMe)(DL)W]-C(O)NH₂;                 [SEQ ID NO: 204]

DITWDELWTLML;                                      [SEQ ID NO: 205]

HLTWDQLWRIMN;                                      [SEQ ID NO: 206]

HITWDQLWNLMN;                                      [SEQ ID NO: 207]

HITWDQLWDTMN;                                      [SEQ ID NO: 208]

HVTWELLWDIMN;                                      [SEQ ID NO: 209]

HITWGQLWDLMN;                                      [SEQ ID NO: 210]

HITWEQLWDLMN;                                      [SEQ ID NO: 211]

EITWFELWEWME;                                      [SEQ ID NO: 212]

MASWVLLWPYMG-C(O)NH₂;                              [SEQ ID NO: 213]

DITWAQLWNIMN,                                      [SEQ ID NO: 214]
where Aib is aminoisobutryic acid, Nal(1) is α-
naphthylalanine, Nal(2) is β-naphthylalanine,
M(SO₂CH₃) is methionine sulfone,
M(OCH₃) is O-methylmethione,
Cbz is benzoxycarbonyl, Ac is acetyl, Succ is
succinimidyl, and N-Me is a methylated
nitrogen on the amine or amide group as
designated therein.
```

Alternative peptide inhibitors of E-selectin are disclosed for example in US Pat. Appl. Pub. No 2005/0181987, which is expressly incorporated herein by reference in its entirety, and which discloses several peptido-mimetics which mimic the topography of the E-selectin ligand:

```
ASAVNLYIPTQE,        [SEQ ID NO: 215]

VYLAPGRISRDY,        [SEQ ID NO: 216]

VYLAPGRFSRDY,        [SEQ ID NO: 217]

CTSHWGVLSQRR,        [SEQ ID NO: 218]

RVLSPESYLGPS,        [SEQ ID NO: 219]

RVLSPESYLGPA,        [SEQ ID NO: 220]

VGNGVLMGRRG,         [SEQ ID NO: 221]

RVLSPESYLGPA,        [SEQ ID NO: 222]

GNCRYIGLRQFG,        [SEQ ID NO: 223]

DIRVEPGGGYTH,        [SEQ ID NO: 224]

APIHTYTGRARG,        [SEQ ID NO: 225]

and RHTCVRSCGHDR.    [SEQ ID NO: 226]
```

In other embodiments, the peptide inhibitors are glycopeptide molecules. Representative molecules of this type are disclosed, for example, by Cummings et al. in International Publication WO 99/065712, which is expressly incorporated herein by reference in its entirety. In particular, this reference discloses glycosulfopeptides (GSPs) which have one or more sulfated tyrosine residues and a glycan linked to the peptide, the glycan desirably including a sialyl Lewis' group or a sialyl Lewis' group. Illustrative GSPs of this type have an O-glycan comprising a β1,6 linkage to a GalNAc. Several exemplary GSPs are disclosed including compounds represented by the formula:

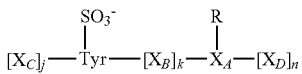

wherein: Tyr is a tyrosine residue; $SO_3^-$ is a sulfate group attached to the tyrosine residue; $X_A$ is an N- or O-linking amino acid residue; R is a sialylated, fucosylated, N-acetyllactosamino glycan in O- or N-linkage to $X_A$; $X_B$, $X_C$, and $X_D$ are amino acid residues; and j, k and n are each from 0 to 12, wherein each amino acid sequence $[X_B]_j$ $[_C]_k$, or $[X_D]_n$ comprises from 0 to 12 amino acid residues. In illustrative examples of this type, the compound comprises no more than 38 amino acids.

In specific embodiments, X comprises one or two sulfated tyrosine residues; j=0 to 10, k=0 to 5, and n=0 to 10; R is selected from the group consisting of $R_1$-$R_{15}$; j=0, k=0 to 5 and n=0; $X_B$ comprises proline; $X_C$ comprises tyrosine; the compound further comprises at least one additional sialylated, fucosylated O-glycan linked to an amino acid residue; $X_A$ is an O-linking amino acid; the O-linking amino acid residue is serine or threonine; $X_A$ is an N-linking amino acid; R comprises a β1,6 linkage to a GAlNAc; and/or R is core-2 based.

In other embodiments, suitable GSPs are selected from the compounds disclosed by Cummings et al in International Publication No. WO 2003/032925, which is expressly incorporated herein by reference in its entirety. Representative GSPs disclosed in the reference have the formula:

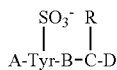

wherein: Tyr is a tyrosine residue; C is an N-, S-, or O-linking amino acid residue; R is a sialylated, fucosylated, N-acetyllactosaminoglycan in O-, S-, or N-linkage to C; A, B, and D are amino acid sequences each comprising from 0 to 12 amino acid residues. In specific embodiments C is serine, threonine, hydroxyproline, tyrosine, lysine, hydroxylysine, methionine, cysteine, asparagine or glutamine; the glycosulfopeptide is conjugated, linked or complexed to a polymeric carrier molecule (e.g., PEG); A of the glycosulfopeptide comprises $X_1$-$X_2$-$X_3$-$X_4$-$X_5$, wherein $X_1$ and $X_3$ are sulfated tyrosines and X2, X4 and X5 are amino acids selected from the group consisting of Ala, Asp, Cys, Glu, Phe, Gly, His, Ile, Lys, Leu, Met, Asn, Pro, Gly, Org, Ser, Thr, Val, Trp, and Tyr, or is absent; B of the glycosulfopeptide is $X_6$-$X_7$-$X_8$-$X_9$-$X_{10}$ wherein each of $X_6$-$X_{10}$ is an amino acid selected from the group consisting of Ala, Asp, Cys, Glu, Phe, Gly, His, Ile, Lys, Leu, Met, Asn, Pro, Gly, Org, Ser, Thr, Val, Trp, and Tyr, or is absent; D of the glycosulfopeptide is $X_{11}$-$X_{12}$-$X_{13}$-$X_{14}$-$X_{15}$-$X_{16}$ wherein each of $X_{11}$-$X_{16}$ is an amino acid selected from the group consisting of Ala, Asp, Cys, Glu, Phe, Gly, His, Ile, Lys, Leu, Met, Asn, Pro, Gly, Org, Ser, Thr, Val, Trp, and Tyr, or is absent.

In still other embodiments, the peptide inhibitor of E-selectin is Ac-TWDQLWDLMK-CONH$_2$ as disclosed for example by Rinnbauer et al. (2003, Glycobiology 13(6). 435-443), which is expressly incorporated herein by reference in its entirety.

In still other embodiments, the E-selectin antagonist is selected from carbohydrate inhibitors of E-selectin. In illustrative examples of this type, the carbohydrate inhibitor is selected from the compounds described by Wong et al. in U.S. Pat. No. 5,830,871, which is expressly incorporated herein by reference in its entirety. In some embodiments, these compounds are represented by any one of the following formulae:

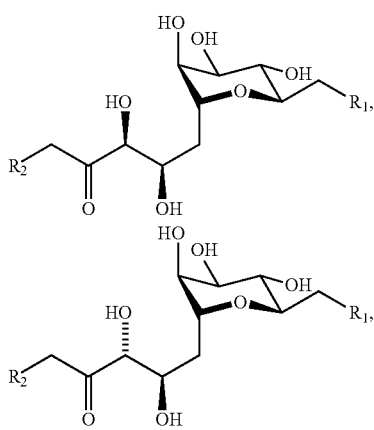

In the above formulas, $R_1$ is a radical selected from the group consisting of —H, —OH, —O—$C_1$-$C_6$, —OBn, —N$_3$, —OSO$_3^{2-}$, —OCOCH$_2$CH$_2$CONHCH(CH$_2$CO$_2$H)CO$_2$H, and —NHR'. R' is a radical selected from the group consisting of alkyl ($C_1$-$C_6$), acyl, decanoyl, phenylacetyl, and —COCH$_2$CH$_2$CO$_2$H. $R_2$ is a radical selected from the group consisting of —CH$_2$PO$_3^{2-}$ and —OPO$_3^{2-}$.

Other embodiments of the carbohydrate inhibitors disclosed by Wong et al., are represented by the following formulae:

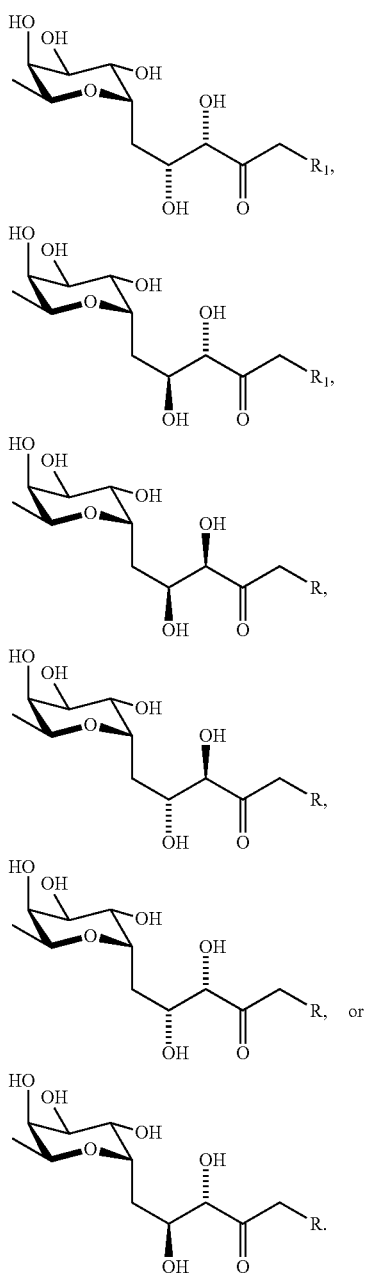

In these embodiments, $R_1$ is a radical selected from the group consisting of —$CH_2POPO_3^{2-}$ and —$OPOPO_3^{2-}$.

Still other embodiments of the carbohydrate inhibitors disclosed by Wong et al., are represented by the following formulae:

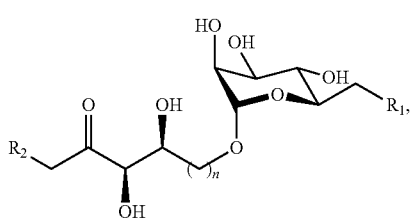

In the above formulas: $R_1$ is a radical selected from the group consisting of —H, —OH, —O-alkyl ($C_1$-$C_6$), —OBn, —$N_3$, —$OPOPO_3^{2-}$, —$OCOCH_2CH_2CONHCH(CH_2CO_2H)CO_2H$, and —NHR'; R' is a radical selected from the group consisting of alkyl ($C_1$-$C_6$), acyl, decanoyl, phenylacetyl, and —$COCH_2CH_2CO_2H$; $R_2$ is a radical selected from the group consisting of —$CH_2PO_3^{2-}$ and $OPO_3^{2-}$; and "n" runs from 1 to 4.

In other illustrative examples, the carbohydrate inhibitor is selected from the oligosaccharide or glycomimetic compounds described by Magnani et al. in International Publication Nos. WO 2008/100453 and WO 2008/060378, which are expressly incorporated herein by reference in their entirety. These compounds are represented by the formula:

wherein:

$R^1$=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; C(=O)OX, alkanyl substituted with C(=O)OX, C(=O)NHX, alkanyl substituted with C(=O)NHX, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH;

$R^2$=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, $OH_1$ or NHX where X=$H_1C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; —C(=O)OX where X is $C_1$-$C_8$ alkanyl, alkenyl, $C_1$-$C_8$ alkynyl, aryl or heteroaryl either of which may be substituted with one or more of Me, OMe, halide, or OH; —C(=O)NH(CH$_2$)—NH$_2$ where n=0-30, C(=O)NHX or CX$_2$OH, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of $Me_1$ OMe, halide, or OH; O(=O)X, OX, NHX, NH(=O)X, where X=$H_1C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; with the proviso that $R^1$ and $R^2$ are not both H;

the cyclohexane derivative is at least attached to the oligosaccharide or glycomimetic compound at an OH, $R^1$ or $R^2$.

In some embodiments, the oligosaccharide or glycomimetic compounds comprise:

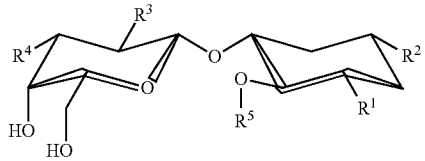

wherein:

$R^1$=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=$H_1C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, $OMe_1$ halide, or OH; C(=O)OX, alkanyl substituted with C(=O)OX, C(=O)NHX, alkanyl substituted with C(=O)NHX, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of $Me_1$ $OMe_1$ halide, or OH;

$R^2$=$H_1C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, $OMe_1$ halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; —C(=O)OX where X is $C_1$-$C_8$ alkanyl, $C_1$-$C_8$ alkenyl, $C_1$-$C_8$ alkynyl, aryl or heteroaryl either of which may be substituted with one or more of Me, OMe, halide, or OH; —C(=O)NH(CH$_2$)$_n$NH$_2$ where n=0-30, C(=O)NHX or CX$_2$OH, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX$_1$ NH(=O)X, where X=$H_1C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; with the proviso that $R^1$ and $R^2$ are not both H;

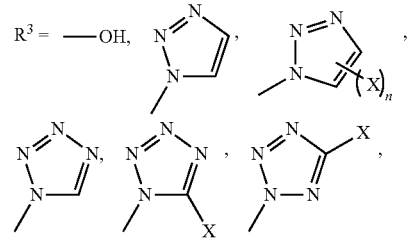

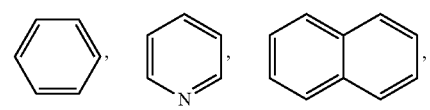

—O—C(=O)—X, —NH$_2$, —NH—C(=O)—NHX, or —NH—C(=O)—X where n=0-2 and X is independently selected from $C_1$-$C_8$ alkanyl, $C_1$-$C_8$ alkenyl, $C_1$-$C_8$ alkynyl,

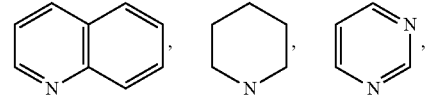

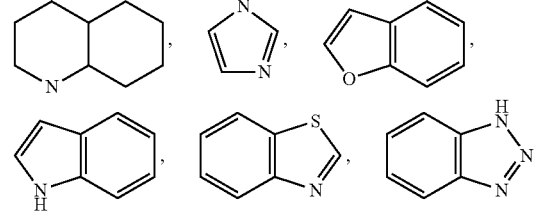

-continued

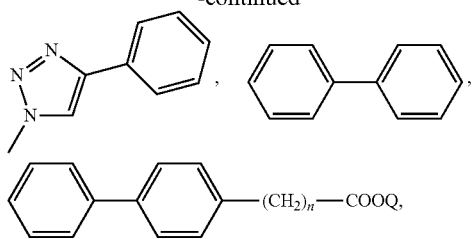

where Q is H or a physiologically acceptable salt, $C_1$-$C_8$ alkanyl, $C_rC_8$ alkenyl, $C_rC_8$ alkynyl, aryl, heteroaryl, $(CH_2)_m$-aryl or $(CH_2)_m$-heteroaryl where m is 1-10, and where n=0-10, and any of the above ring compounds may be substituted with one to three independently selected of Cl, F, $CF_3$, $C_rC_8$ alkoxy, $NO_2$, $C_1$-$C_8$ alkanyl, $C_rC_8$ alkenyl, $C_1$-$C_8$ alkynyl, $C_1$-$C_{14}$ aryl, or OY, C(=O)OY, $NY_2$ or C(=O)NHY where Y is H, $C_1$-$C_8$ alkanyl, $C_1$-$C_8$ alkenyl, $C_1$-$C_8$ alkynyl, or $C_1$-$C_{14}$ aryl;

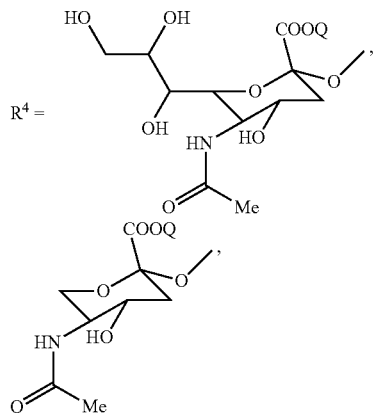

6'sulfated GlcNAc, 6'carboxylated GlcNAc, 6'sulfated GalNAc, 6'sulfated galactose, 6'carboxylated galactose,

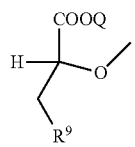

where Q is H or a physiologically acceptable salt or $C_rC_8$ alkanyl, $C_1$-$C_8$ alkenyl, $C_1$-$C_8$ alkynyl, aryl, heteroaryl, $(CH_2)_n$-aryl or $(CH_2)_n$-heteroaryl where n is 1-10, and where $R^9$ is aryl, heteroaryl, cyclohexane, t-butane, adamantane, or triazole, and any of $R^9$ may be substituted with one to three independently selected of Cl, F, $CF_3$, $C_1$-$C_8$ alkoxy, $NO_2$, $C_1$-$C_8$ alkanyl, $C_1$-$C_8$ alkenyl, $C_1$-$C_8$ alkynyl or OY, $NY_2$ or C(=O)NHY where Y is H, $C_1$-$C_8$ alkanyl, $C_1$-$C_8$ alkenyl, $C_1$-$C_8$ alkynyl or $C_1$-$C_{14}$ aryl; or

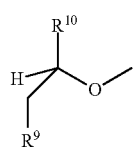

where $R^{10}$ is one of

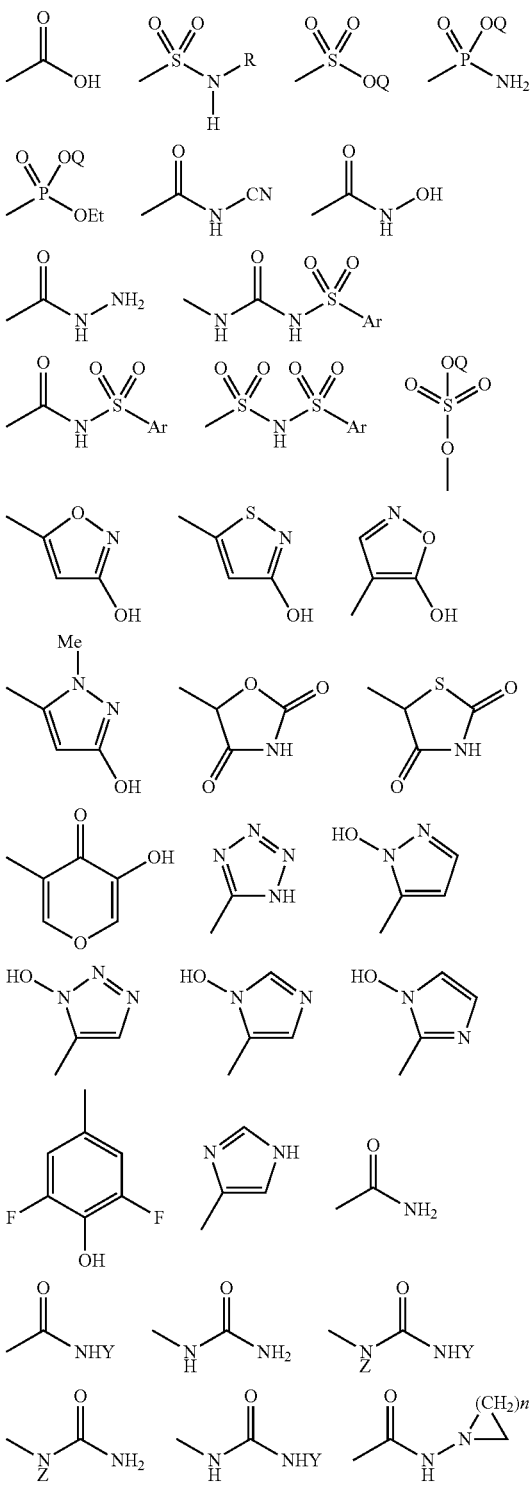

where Q is H or a physiologically acceptable salt, $C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, n=1-4, Z and Y=$C_1$-$C_8$ alkanyl, $C_rC_8$ alkenyl, $C_rC_8$ alkynyl, halogenated $C_rC_8$ alkanyl, aryl and heteroaryl substituted with Me, OMe, halide, OH; and $R^5$=H, D-mannose, L-galactose, D-arabinose, L-fucose, polyols

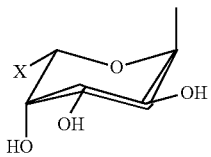

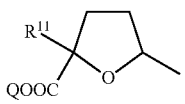

where X=$CF_3$, cyclopropyl or phenyl, or where Q is H or a physiologically acceptable salt, $C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, and where $R^{11}$ is aryl, heteroaryl,

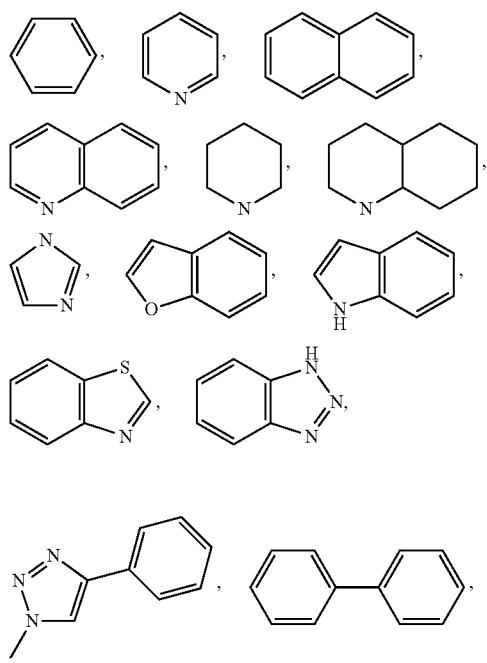

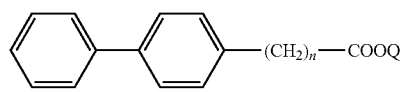

where Q is H or a physiologically acceptable salt, $C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, and where n=0-10, and any one of the above ring compounds may be substituted with one to three independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl or $C_1$-$C_8$ alkynyl.

In some embodiments, the oligosaccharide or glycomimetic compounds are represented by the formula:

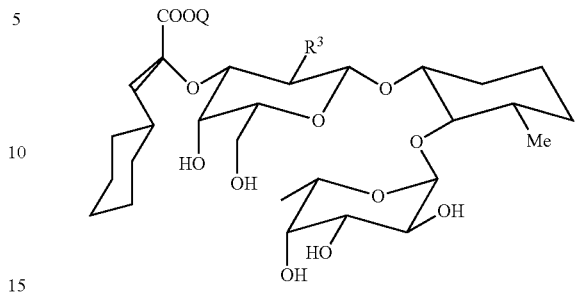

where Q is H or a physiologically acceptable salt, and Me is methyl.

In other embodiments, the oligosaccharide or glycomimetic compounds are represented by the formula:

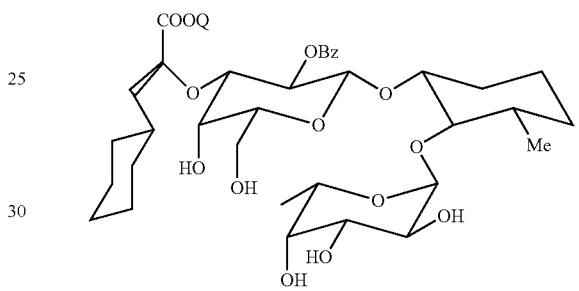

where Q is H or a physiologically acceptable salt, Me is methyl and Bz is benzoyl.

In still other embodiments, the oligosaccharide or glycomimetic compounds are represented by the formula:

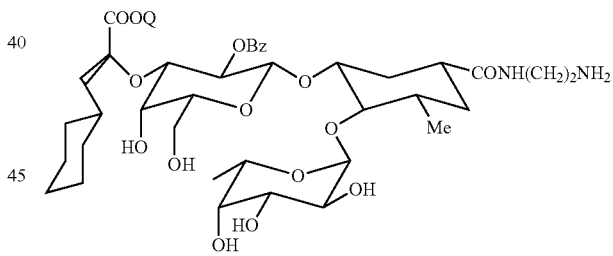

where Q is H or a physiologically acceptable salt, Me is methyl and Bz is benzoyl.

In other embodiments, the oligosaccharide or glycomimetic compounds are represented by the formula:

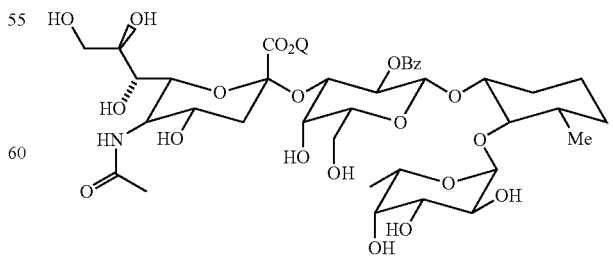

where Q is H or a physiologically acceptable salt, Me is methyl and Bz is benzoyl.

In still other embodiments, the oligosaccharide or glycomimetic compounds are represented by the formula:

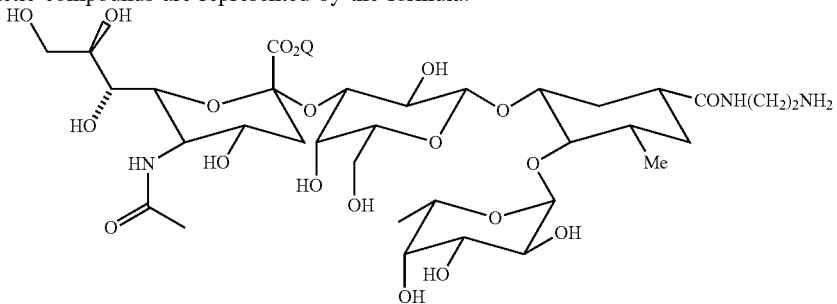

where Q is H or a physiologically acceptable salt and Me is methyl.

In further embodiments, the oligosaccharide or glycomimetic compounds are represented by the formula:

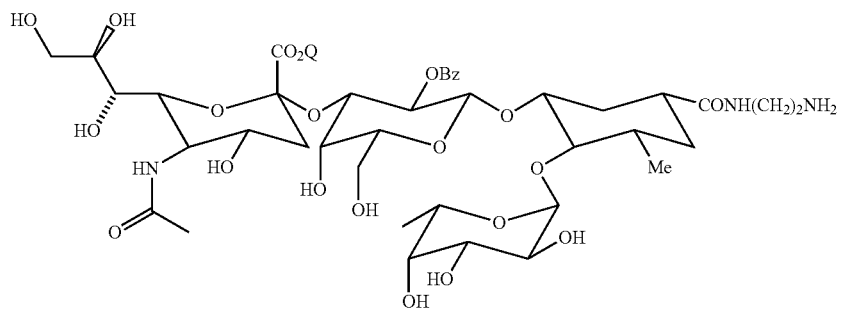

where Q is H or a physiologically acceptable salt, Me is methyl and Bz is benzoyl.

In other embodiments, the oligosaccharide or glycomimetic compounds are represented by the formula:

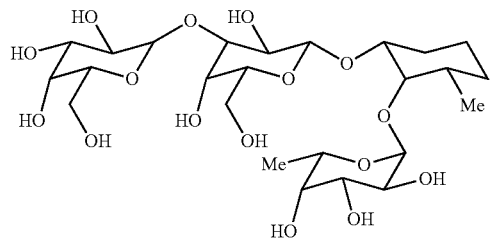

where Me is methyl.

In still other embodiments, the oligosaccharide or glycomimetic compounds are represented by the formula:

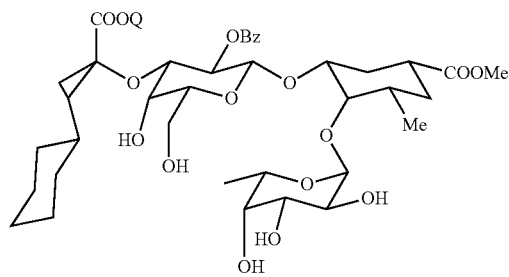

where Q is H or a physiologically acceptable salt, Me is methyl and Bz is benzoyl.

In other embodiments, the oligosaccharide or glycomimetic compounds are represented by the formula:

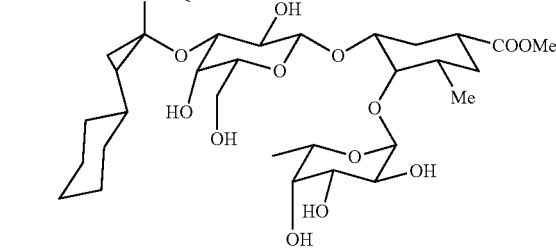

where Q is H or a physiologically acceptable salt, Me is methyl and Bz is benzoyl.

Still other embodiments of the oligosaccharide or glycomimetic compounds are represented by the formula:

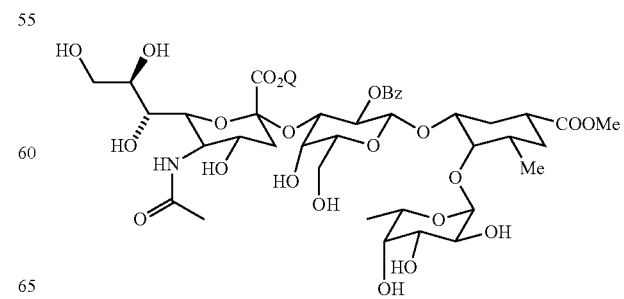

where Q is H or a physiologically acceptable salt, Me is methyl and Bz is benzoyl.

Yet other embodiments of the oligosaccharide or glycomimetic compounds are represented by the formula:

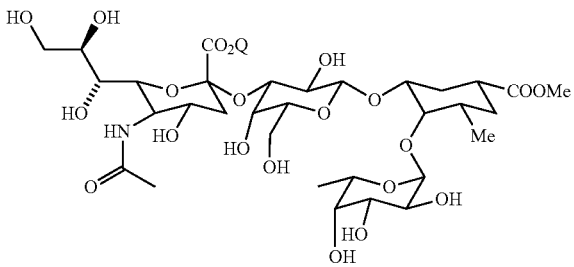

where Q is H or a physiologically acceptable salt and Me is methyl.

Other embodiments of the oligosaccharide or glycomimetic compounds are represented by the formula:

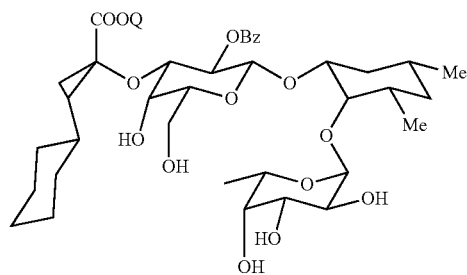

where Q is H or a physiologically acceptable salt, Me is methyl and Bz is benzoyl.

In other embodiments, the oligosaccharide or glycomimetic compounds are represented by the formula:

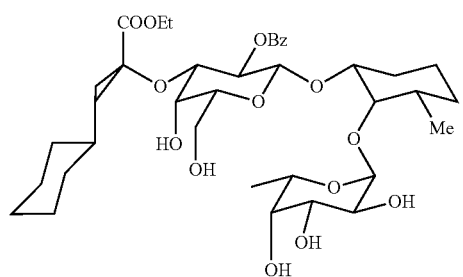

where Me is methyl, Et is ethyl and Bz is benzoyl.

In still other embodiments, the oligosaccharide or glycomimetic compounds are represented by the formula:

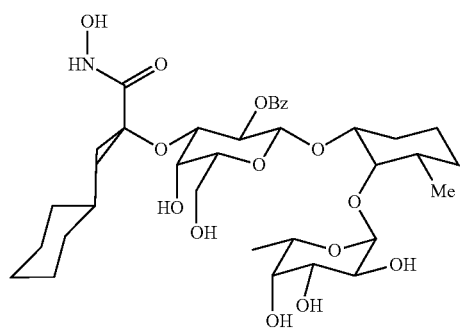

where Me is methyl and Bz is benzoyl.

Other embodiments of the oligosaccharide or glycomimetic compounds are represented by the formula:

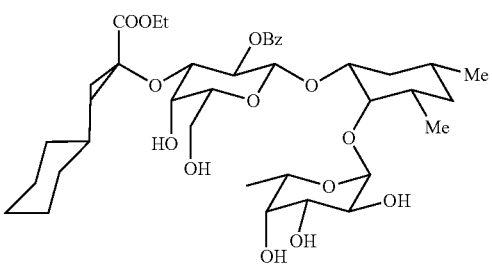

where Me is methyl, Et is ethyl and Bz is benzoyl.

Still other embodiments of the oligosaccharide or glycomimetic compounds are represented by the formula:

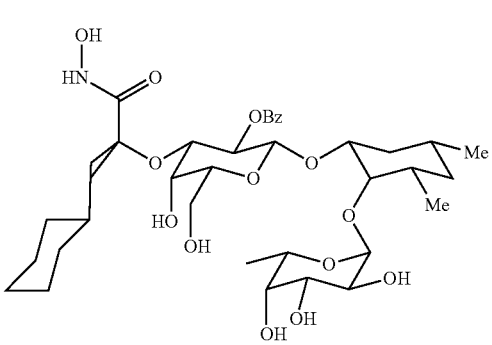

where Me is methyl and Bz is benzoyl.

Alternative carbohydrate inhibitors by Magnani et al. are disclosed in International Publication No. WO 2007/028050, which is expressly incorporated herein by reference in its entirety. These compounds are represented by the formula:

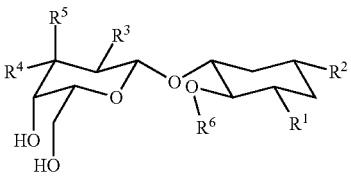

wherein:

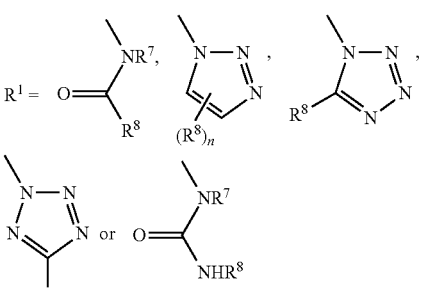

where n=0-2, and $R^8$ are independently selected where n=2;

R² = H, —C(═O)OX where X is $C_1$-$C_8$ alkanyl, $C_1$-$C_8$ alkenyl, $C_1$-$C_8$ alkynyl or $C_1$-$C_{14}$ aryl, —C(═O)NH(CH₂)ₙNH₂, —[C(═O)NH(CH₂)ₙNHC(═O)]ₘ(L)ₘZ, where n=0-30, m=0-1, L is a linker, and Z is a benzyl amino sulfonic acid, a benzyl amino carboxylic acid, a polyethylene glycol, or a second compound or salt thereof having the above formula to form a dimer where R² of the second compound or salt thereof has m=0, no Z, and is the point of attachment;

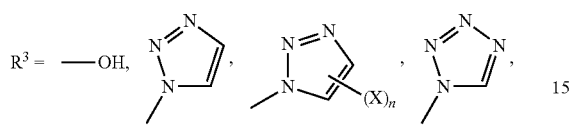

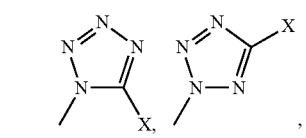

—O—C(═O)—X, —NH₂, —NH—C(═O)—NHX, or —NH—C(═O)—X where n=0-2 and X is independently selected from $C_1$-$C_8$ alkanyl, $C_1$-$C_8$ alkenyl, $C_1$-$C_8$ alkynyl,

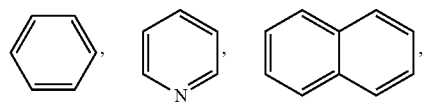

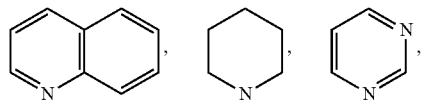

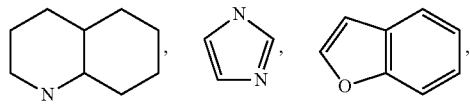

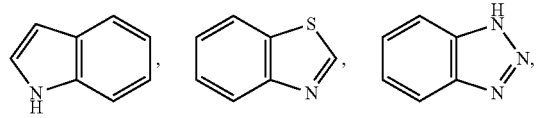

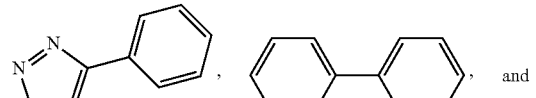

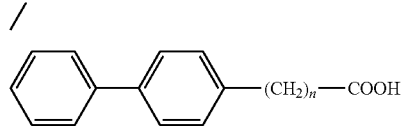

where n=0-10,
and any of the above ring compounds may be substituted with one to three independently selected of Cl, F, $C_1$-$C_8$ alkanyl, $C_1$-$C_8$ alkenyl, $C_1$-$C_8$ alkynyl, $C_1$-$C_{14}$ aryl, or OY where Y is H, $C_1$-$C_8$ alkanyl, $C_1$-$C_8$ alkenyl, $C_1$-$C_8$ alkynyl, or $C_1$-$C_{14}$ aryl;

R⁴ = 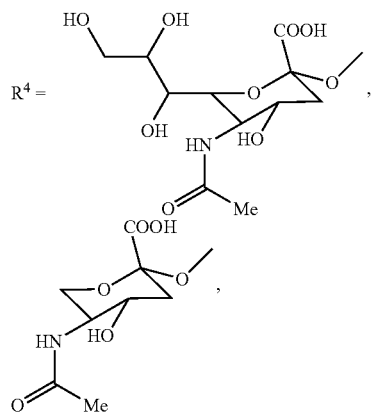

6'sulfated GlcNAc, 6'carboxylated GlcNAc, 6'sulfated GalNAc, 6'sulfated galactose, 6'carboxylated galactose or

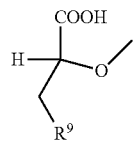

where R⁹ is aryl, heteroaryl, cyclohexane, t-butane, adamantane, or triazole, and any of R⁹ may be substituted with one to three independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl, $C_1$-$C_8$ alkynyl or $C_1$-$C_{14}$ aryl;

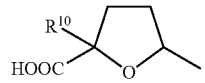

R⁵=H, or R⁴ and R are taken together to form where R¹⁰ is aryl, heteroaryl,

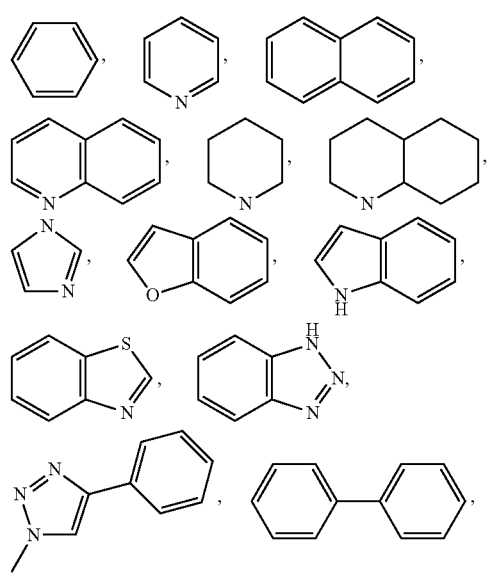

where n=0-10, and any one of the above ring compounds may be substituted with one to three independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl or $C_1$-$C_8$ alkynyl;

$R^6$=H, fucose, mannose, arabinose, galactose or polyols;

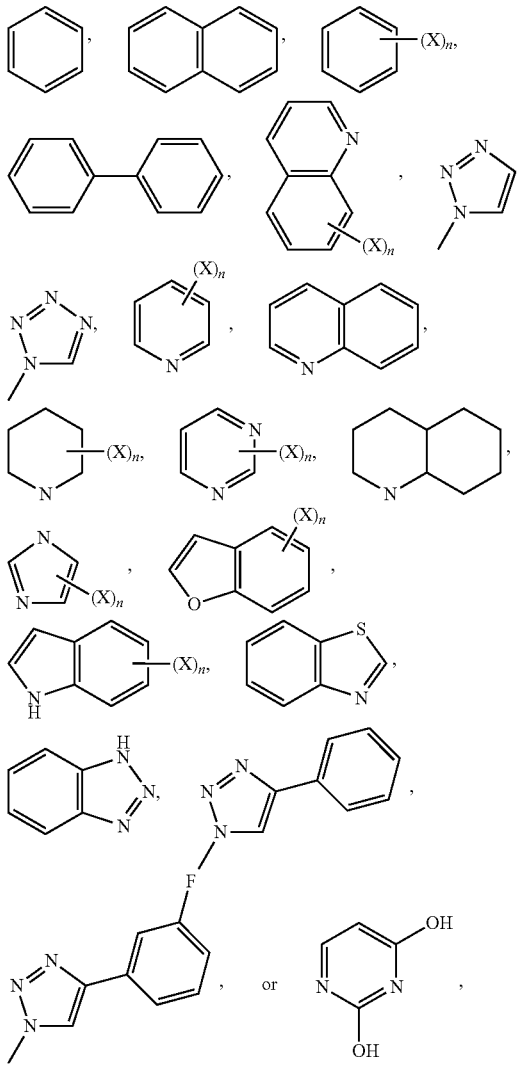

$R^7$=H, $C_1$-$C_8$ alkanyl, $C_1$-$C_8$ alkenyl, $C_1$-$C_8$ alkynyl or
$R^8$=H, $C_1$-$C_8$ alkanyl, $C_1$-$C_8$ alkenyl, $C_1$-$C_8$ alkynyl, where n=0-3 and X is independently selected from H, OH, Cl, F, $N_3$, $NH_2$, $C_1$-$C_8$ alkanyl, $C_1$-$C_8$ alkenyl, $C_1$-$C_8$ alkynyl, $C_1$-$C_{14}$ aryl, $OC_1$-$C_8$ alkanyl, $OC_1$-$C_8$ alkenyl, $OC_1$-$C_8$ alkynyl, and $OC_1$-$C_{14}$ aryl, and any of the above ring compounds may be substituted with one to three independently selected of Cl, F, $C_1$-$C_8$ alkanyl, $C_1$-$C_8$ alkenyl, $C_1$-$C_8$ alkynyl, $C_1$-$C_{14}$ aryl or OY where Y is H, $C_1$-$C_8$ alkanyl, $C_1$-$C_8$ alkenyl, $C_1$-$C_8$ alkynyl, or $C_1$-$C_{14}$ aryl.

Alternate carbohydrate inhibitors by Magnani et al. are disclosed in US Appl. Pub. No. 2006/0194745, which is expressly incorporated herein by reference in its entirety. These compounds have the formula:

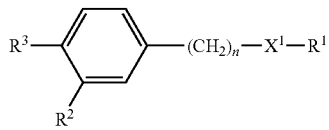

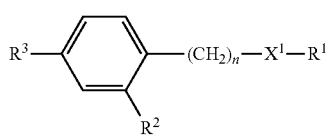

where n is 0 or 1; $X^1$ is —$PO_2M$, —$SO_2M$ or —$CF_2$— wherein M is a pharmaceutically acceptable counterion; $R^1$ is —OH, —F or —$CO_2R^4$ where $R^4$ is —H or —$(CH_2)_m$—$CH_3$ and m is 0 to 3; $R^2$ is —H, —$PO_3M_2$, —$SO_3M_2$, —$CH_2$—$PO_3M_2$, —$CH_2$—$SO_3M_2$, —$CF_3$, —$(CH_2)_m$—$C(R^6)H$—$R^5$ or $R^9$—$N(R^{19})$— wherein M is defined as above; $R^3$ is —H, —$(CH_2)_m$—$C(R^6)H$—$R^5$ or $R^9$—$N(R^1)$ where $R^5$ and $R^6$ are independently selected from —H, —$CO_2$—$R^7$ and —NH—$R^8$; $R^7$ and $R^8$ are independently selected from hydrogen, an alkyl group, an aromatic group, an amino group and a carboxy group, and $R^9$ and $R^{10}$ are independently selected from —H, —$(CH_2)_m$—$CH_3$; —$CH_2$—Ar, and —CO—Ar, where m is 0 to 3 and Ar is an aromatic group; or

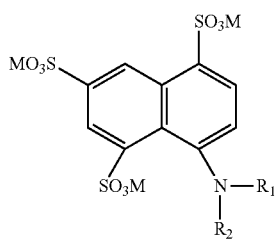

where $R_1$ and $R_2$ are independently selected from hydrogen, an alkyl group, an aromatic group, an amino group or a carboxy group, and —CO—$R_3$ where $R_3$ is as defined above; and M is a pharmaceutically acceptable counterion.

Other carbohydrate inhibitors by Magnani et al. are disclosed in International Publication No. WO 2006/127906, which is expressly incorporated herein by reference in its entirety. These compounds have the formula:

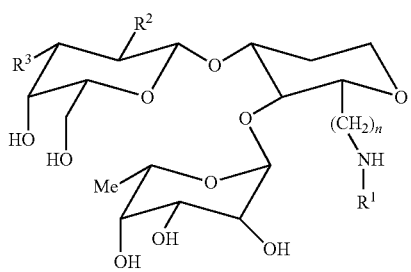

wherein: n=0-20

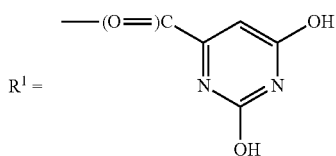

a benzyl amino sulfonic acid, a benzyl amino carboxylic acid, or a second compound or salt thereof having the above formula to form a dimer;

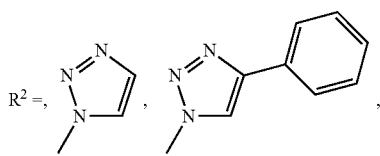

—O—C(=O)—X or —NH—C(=O)—X
where X is

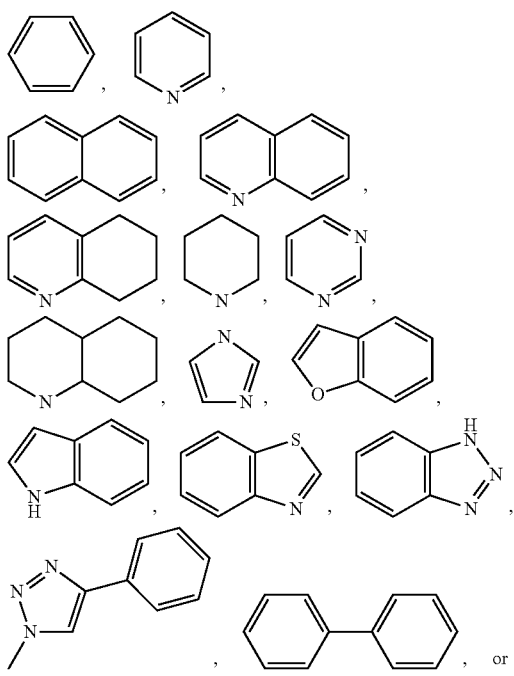

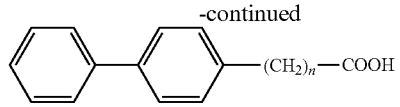

where n=0-10, and any of the above ring compounds may be substituted with one to three of Cl, F, $C_1$-$C_8$ alkanyl or OY where Y is H or $C_1$-$C_8$ alkanyl;

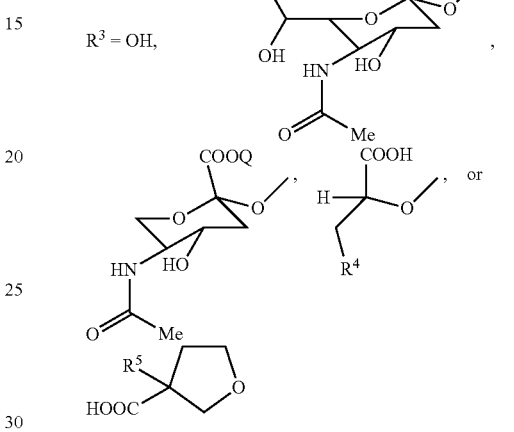

where $R^4$ is cyclohexane, t-butane, adamantane, benzene, triazole, or triazole substituted with one to three of $C_1$, $F_1$ $C_1$-$C_8$ alkanyl or OY where Y is H or $C_1$-$C_8$ alkanyl, and where $R^5$ is

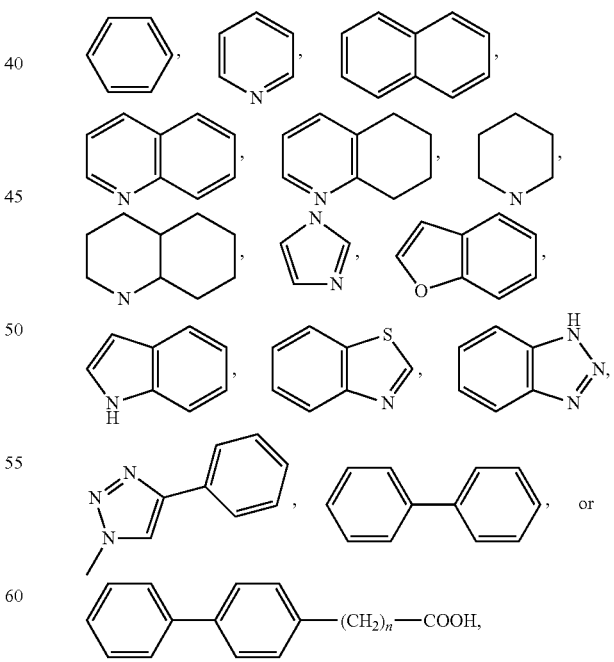

where n=0-10, and any one of the above ring compounds may be substituted with one to three of Cl, F, $C_1$-$C_8$ alkanyl or OY where Y is H or $C_1$-$C_8$ alkanyl; and with the proviso that where $R^1$ is a benzyl amino sulfonic acid and $R^2$ or X of $R^2$ is aromatic, then $R^4$ of $R^3$ is not cyclohexane.

Alternative carbohydrate inhibitors by Magnani et al. are disclosed in International Publication No. WO 2005/054264, which is expressly incorporated herein by reference in its entirety. These compounds are represented by the formula:

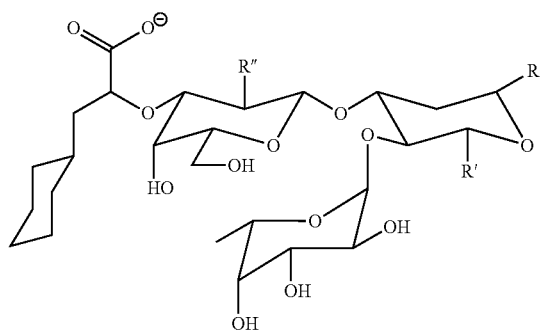

wherein;
R=H or a benzyl amino sulfonic acid;
R'=a benzyl amino sulfonic acid,

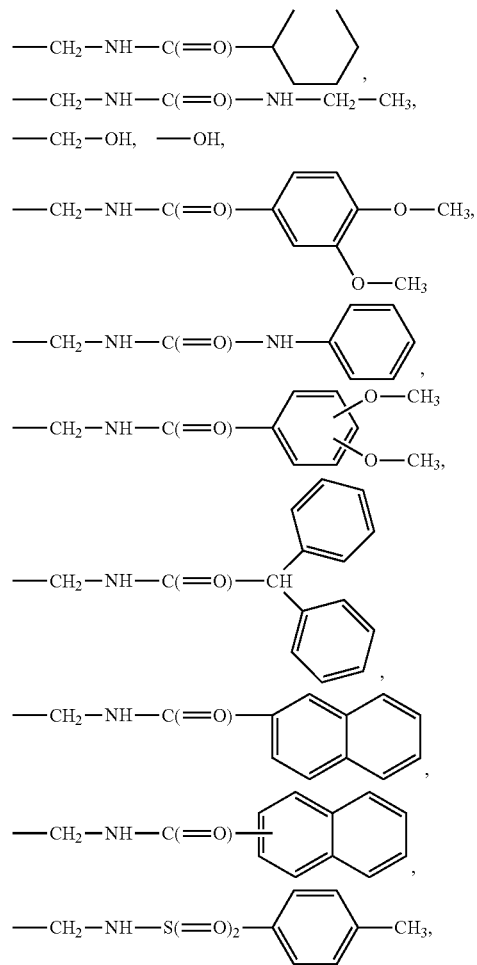

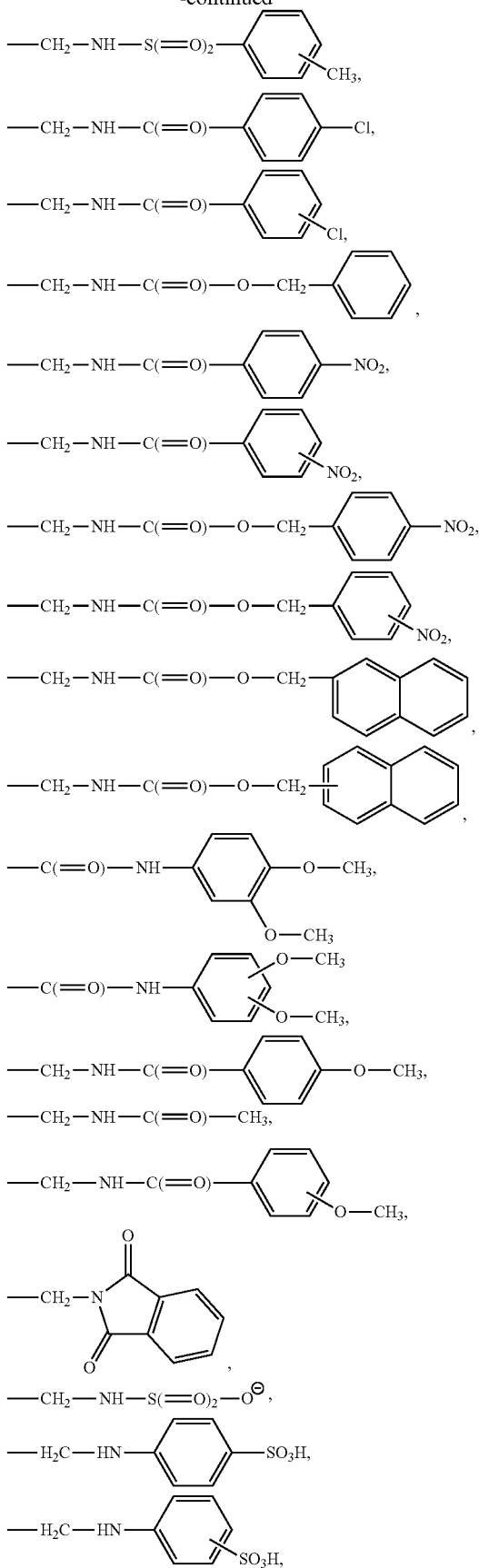

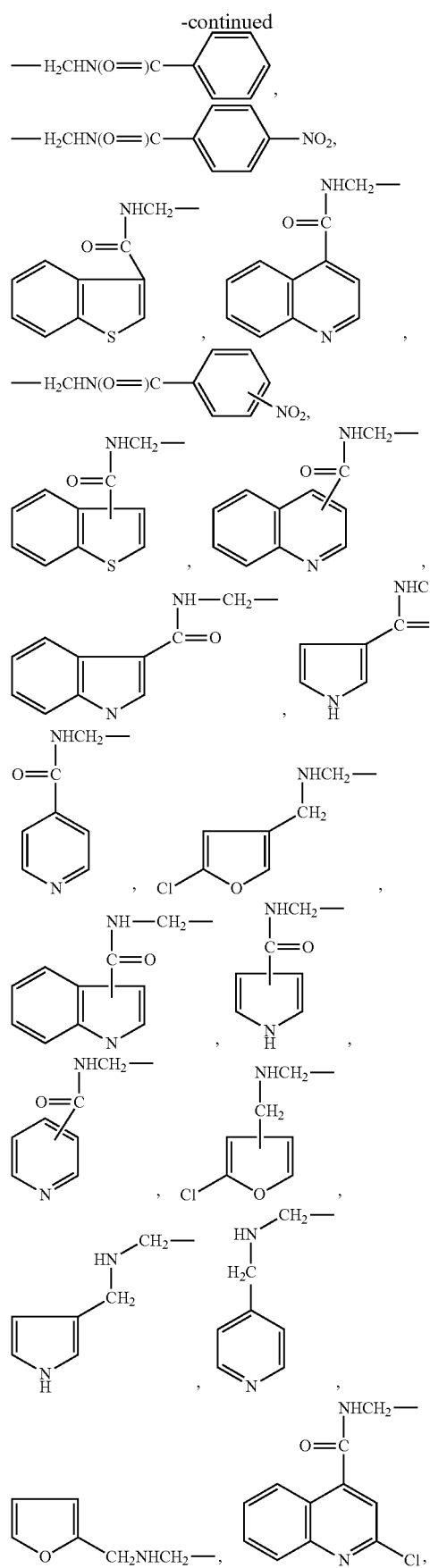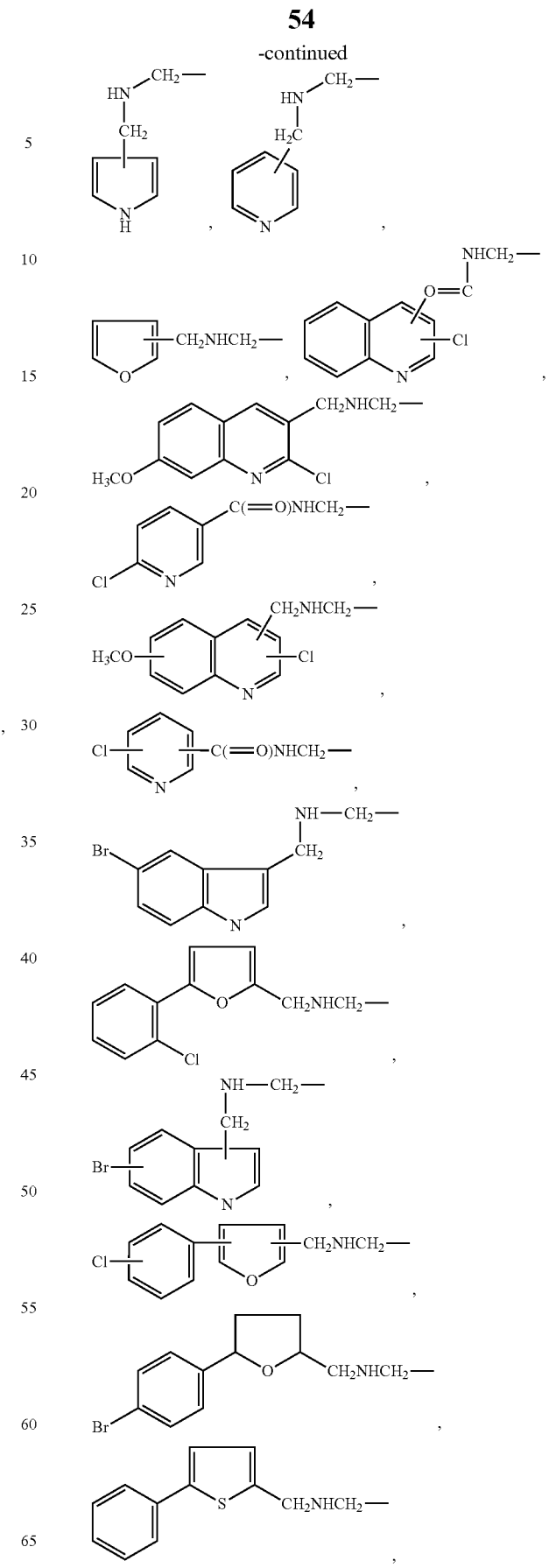

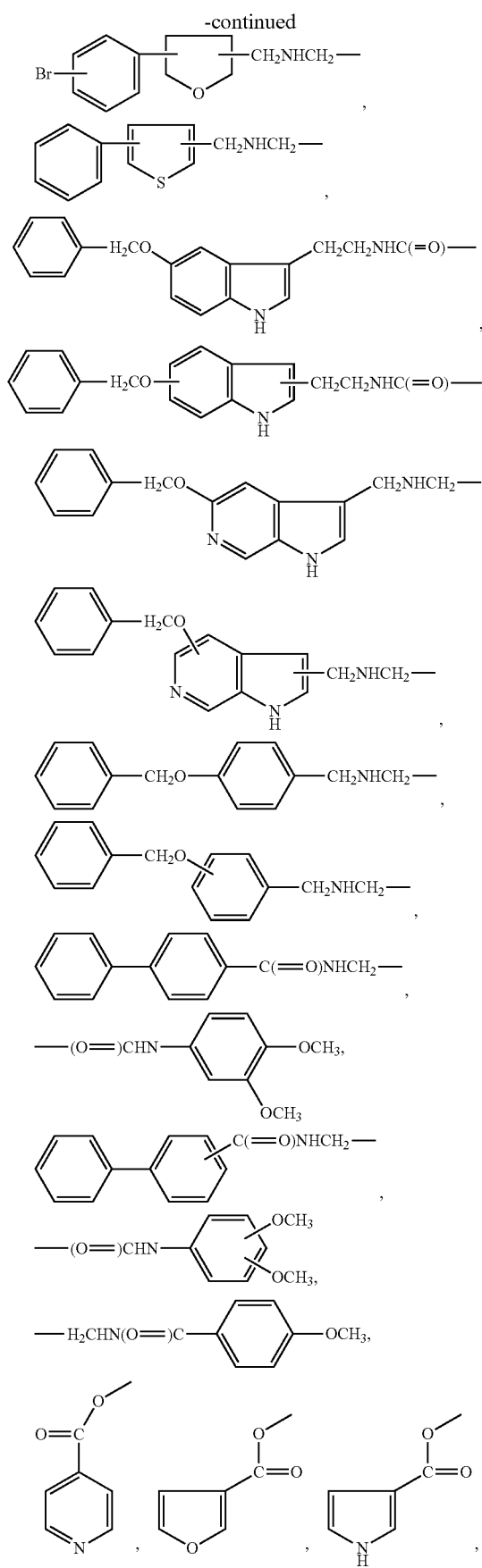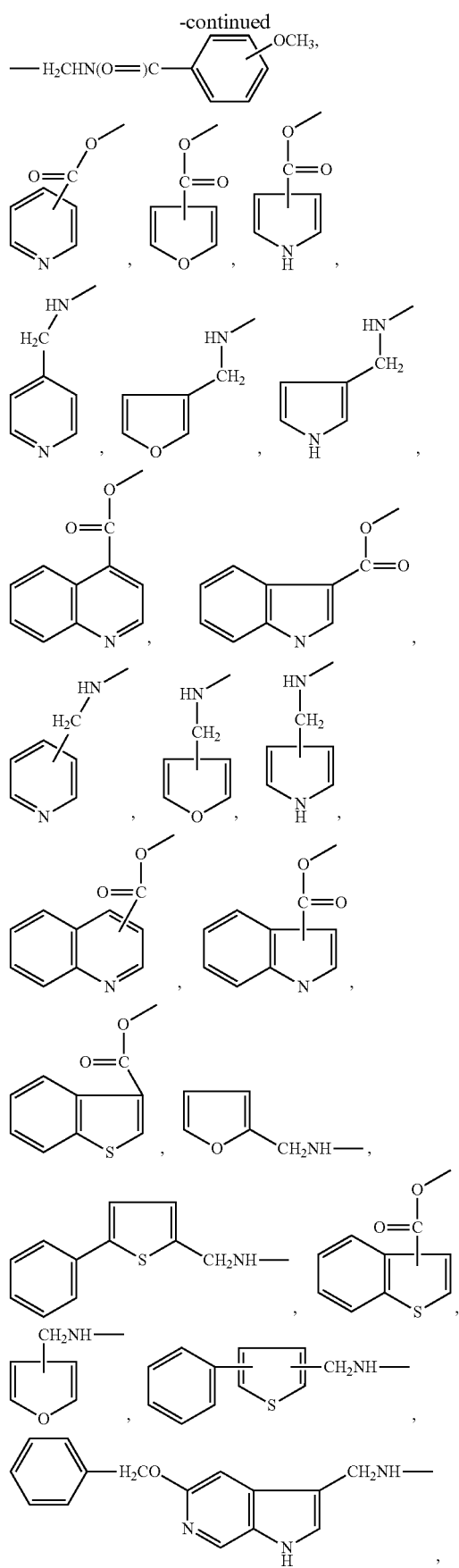

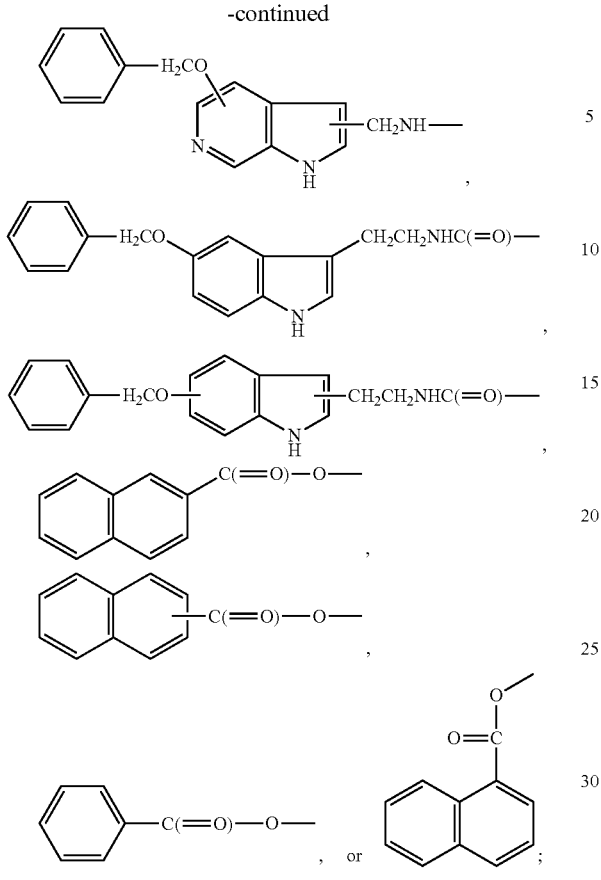
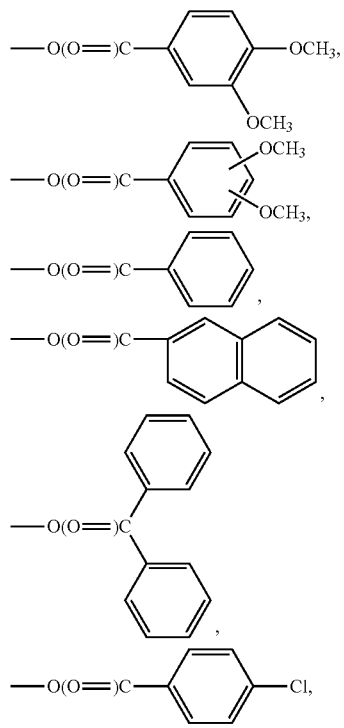
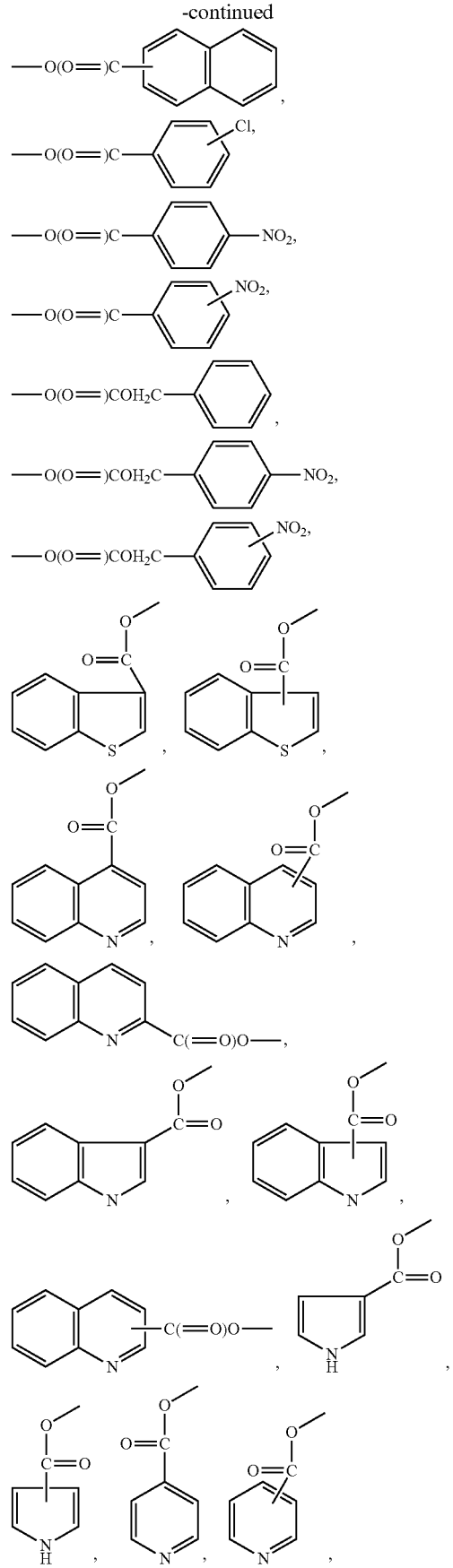
R″=a benzyl amino sulfonic acid, —OH, —OC(=O)—NH—CH$_2$—CH$_3$,

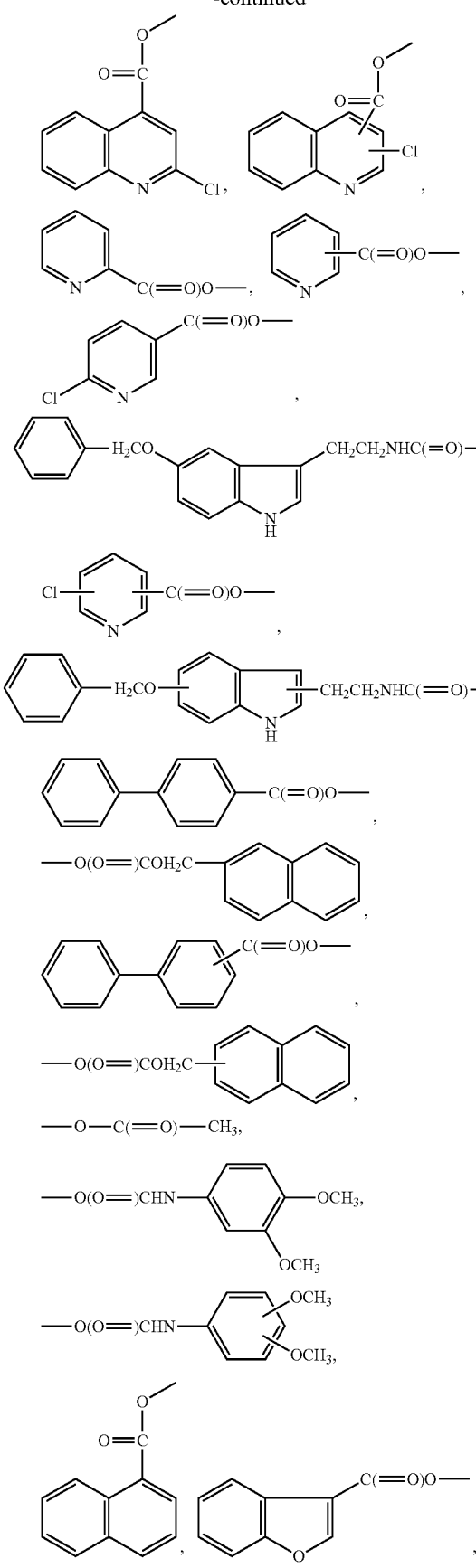
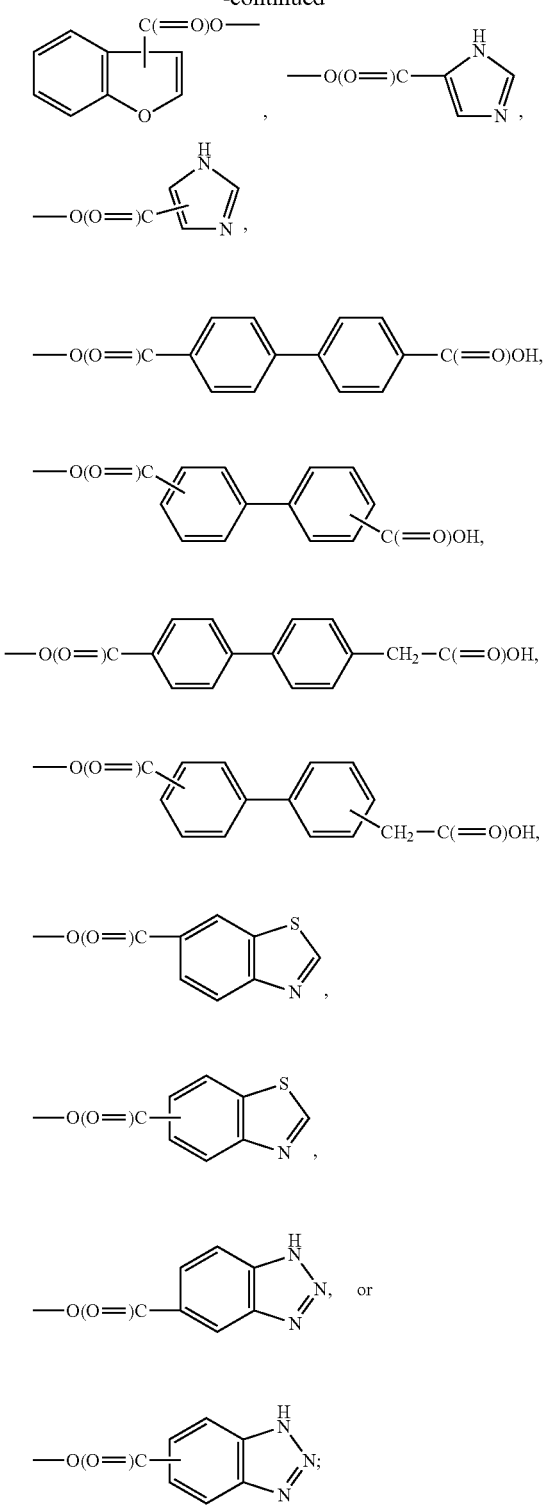
wherein the compound possesses a benzyl amino sulfonic acid at R, R' or R" but not at more than one of R, R' and R".
Still other carbohydrate inhibitors by Magnani et al. are disclosed in International Publication No. WO 2005/051920, which is expressly incorporated herein by reference in its entirety. These compounds are represented by the formula:

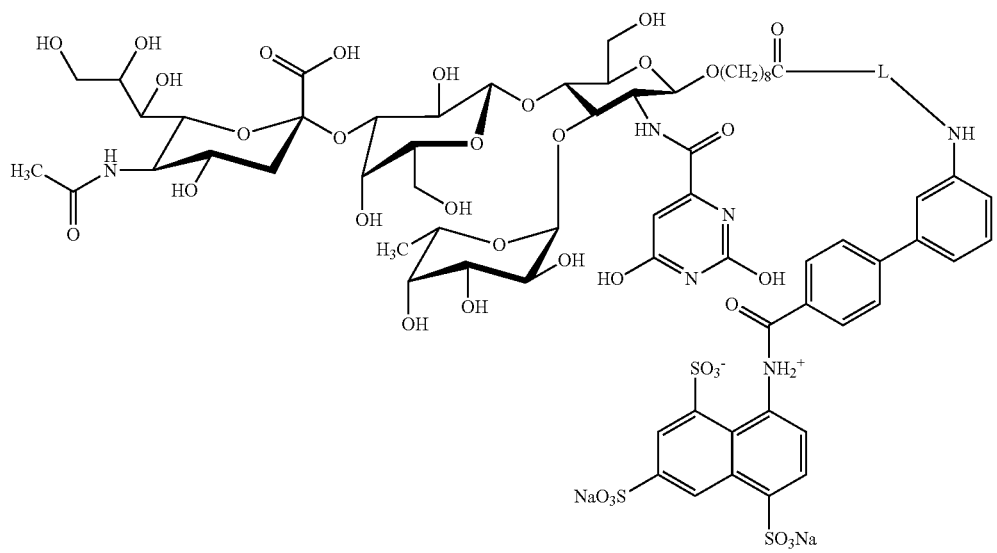
where L is a linker, which is suitably selected from:
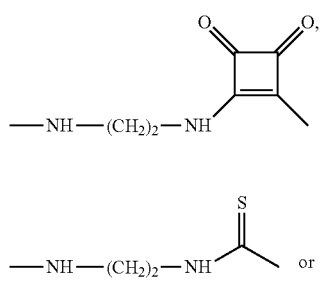
Alternative carbohydrate inhibitors by Magnani et al. are disclosed in International Publication No. WO 2004/004636, which is expressly incorporated herein by reference in its entirety. Non-limiting examples of these compounds are selected from:
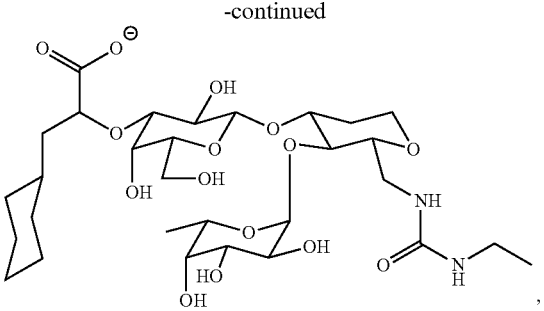
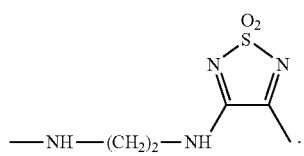
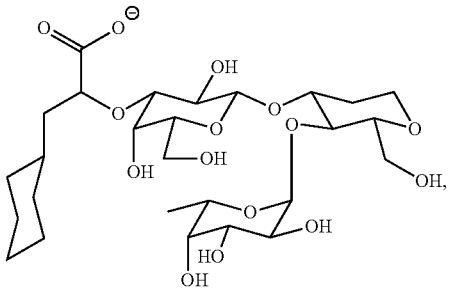
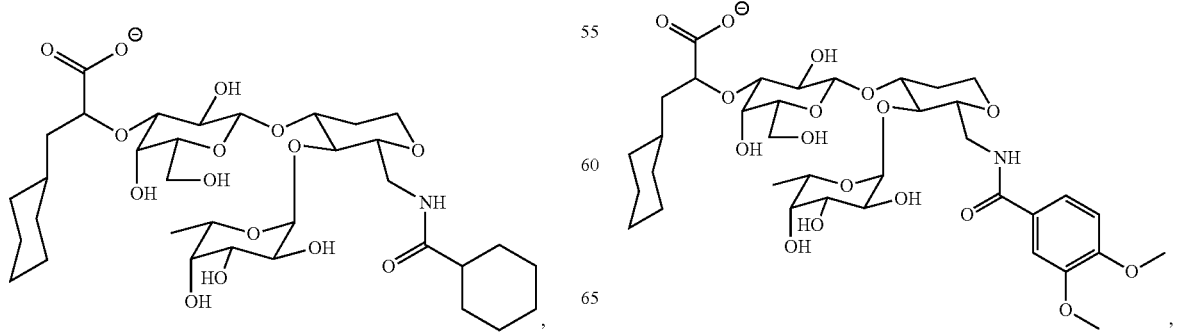

63
-continued
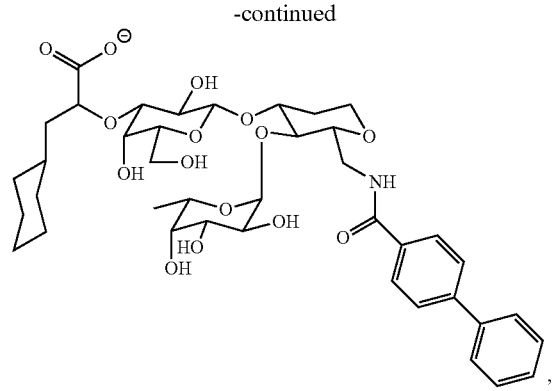
,
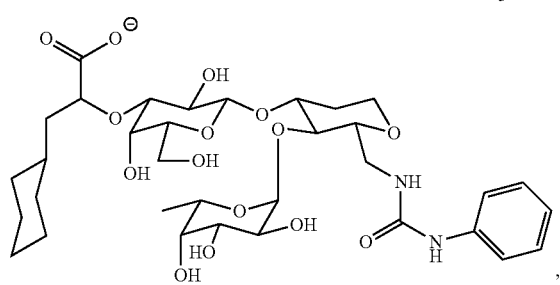
,
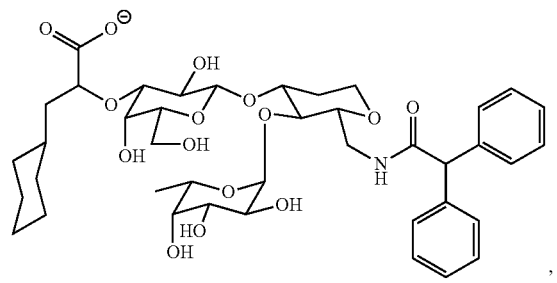
,
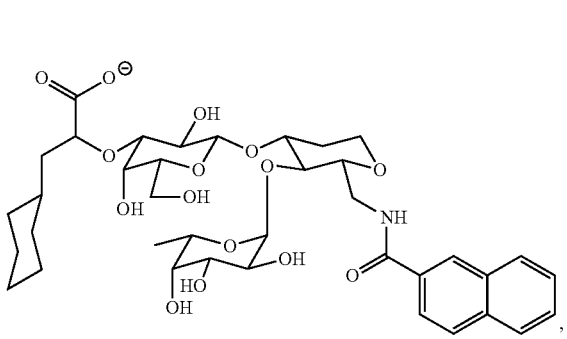
,
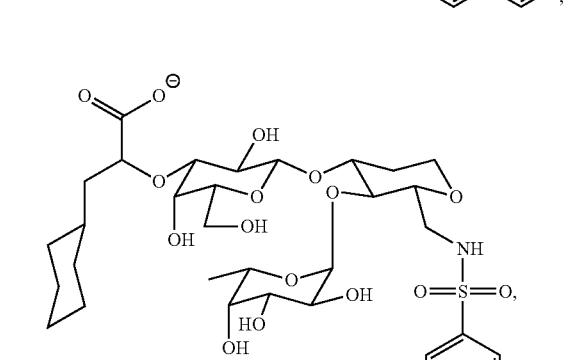
,
64
-continued
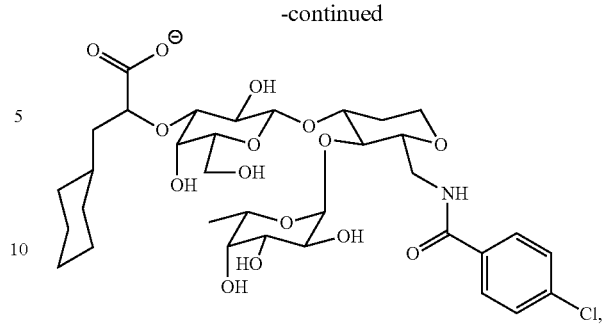
Cl,
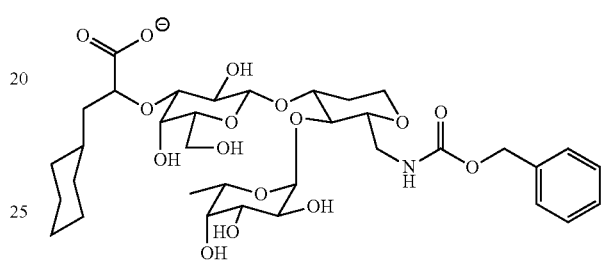
,
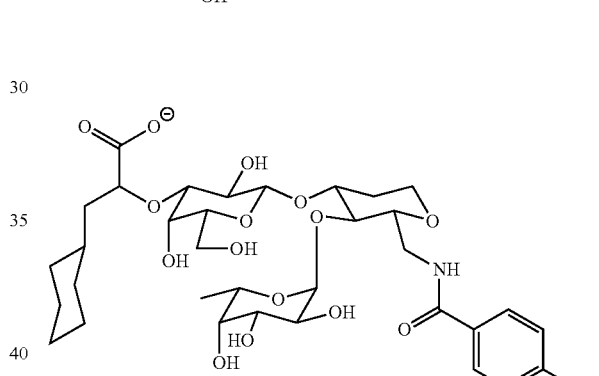
NO₂,
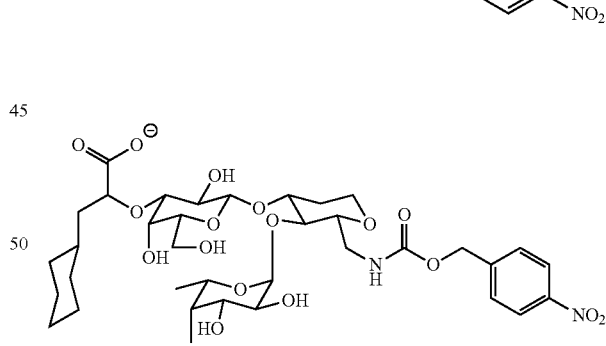
NO₂,
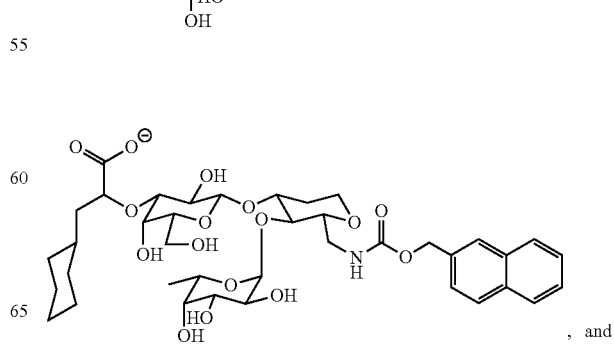
, and -continued
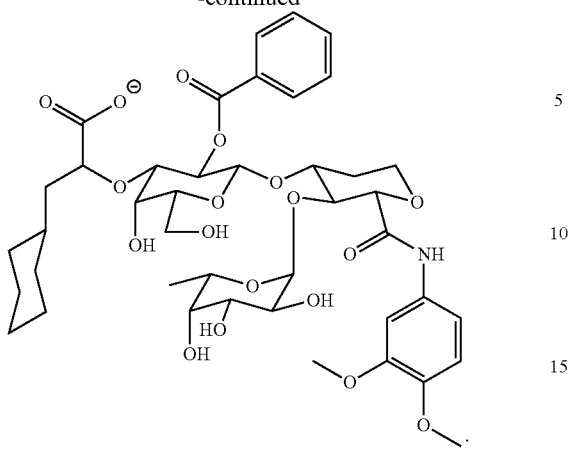
Further carbohydrate inhibitors by Magnani et al. are disclosed in International Publication No. WO 2003/097658, which is expressly incorporated herein by reference in its entirety. These compounds are represented by a formula selected from the group consisting of:
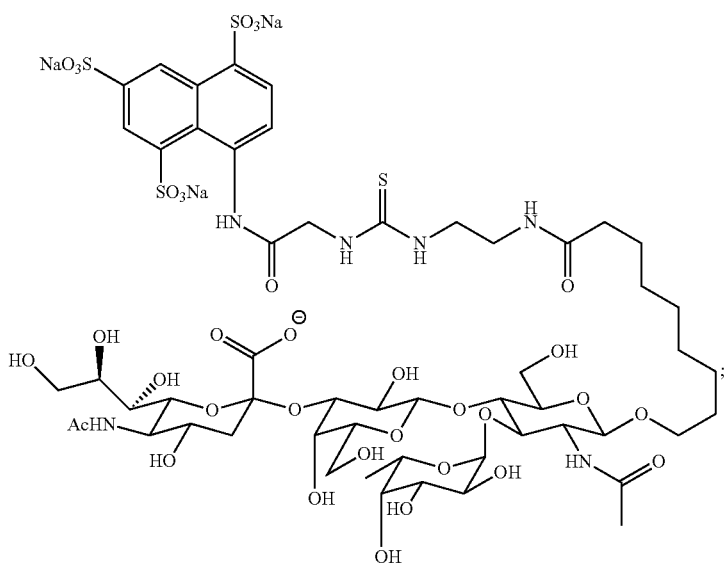

-continued
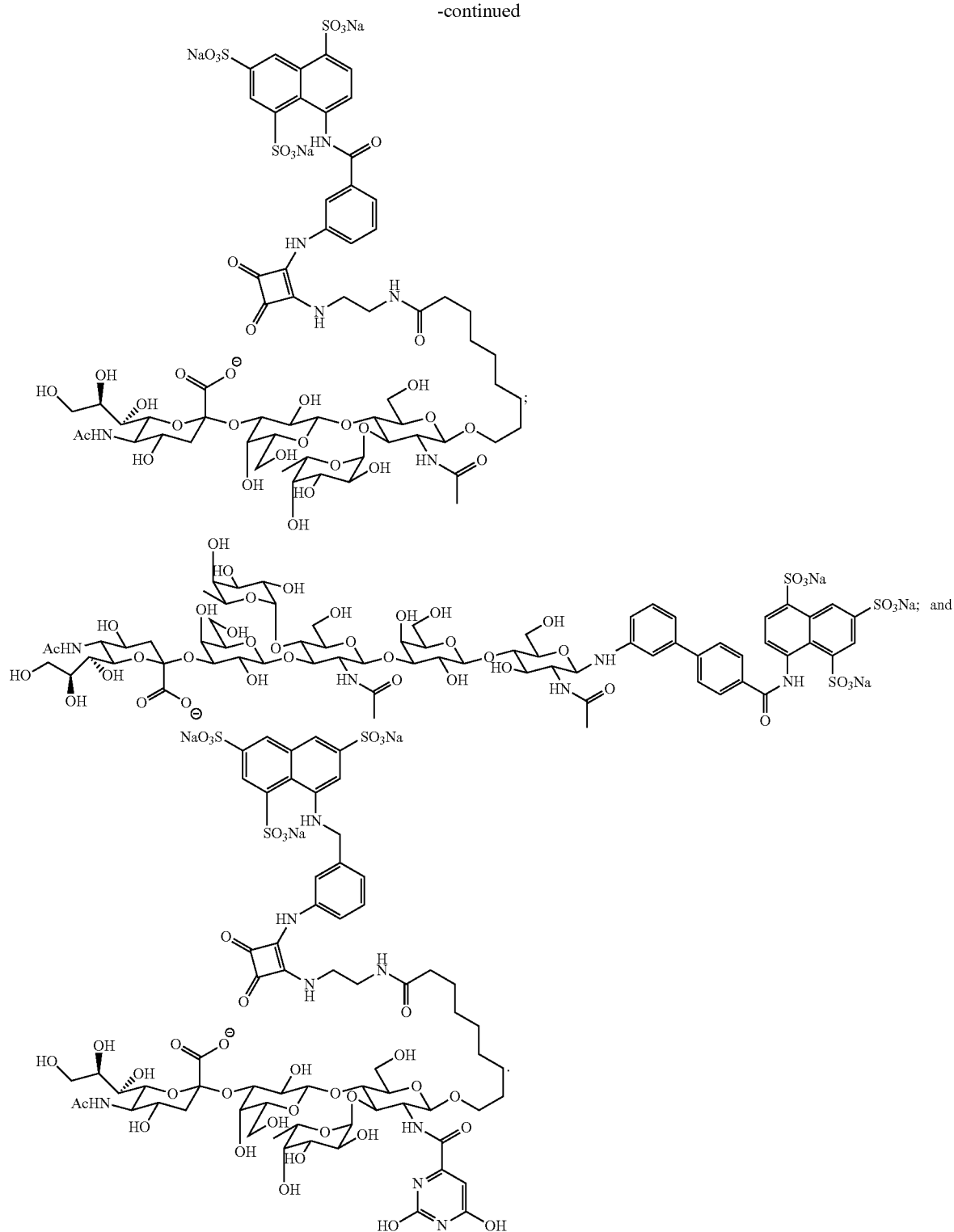
Still other carbohydrate inhibitors by Magnani et al. are disclosed in U.S. Pat. No. 7,361,644, which is expressly incorporated herein by reference in their entirety. These compounds are selected from the following formulas:

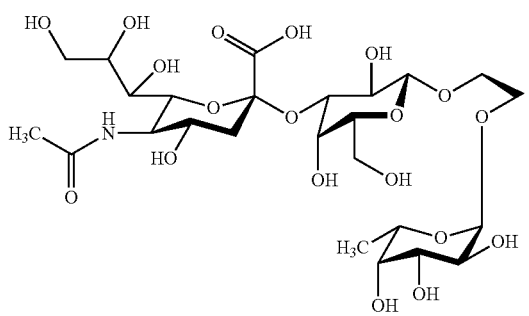
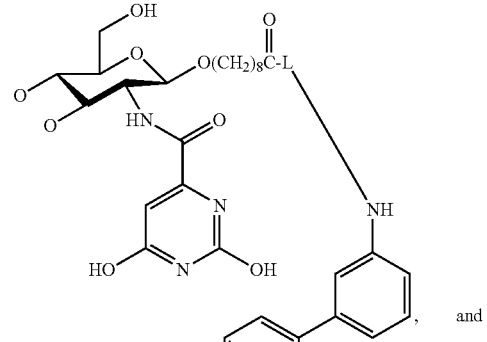

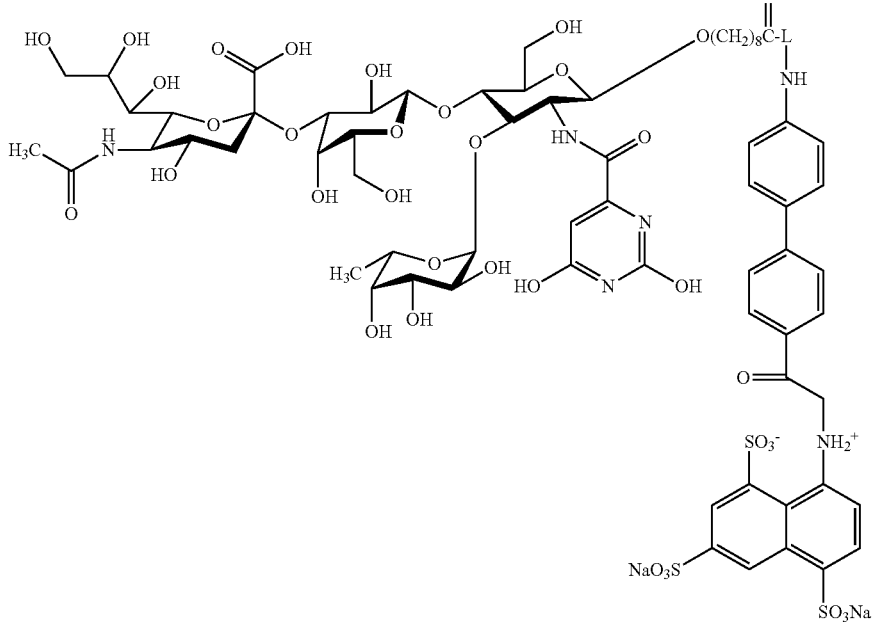

wherein L is a linker.
Representative linkers according to these examples are selected from:

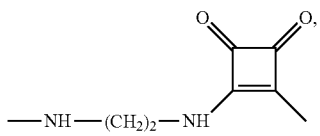

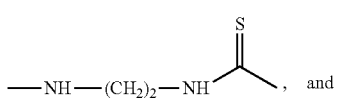
, and

-continued

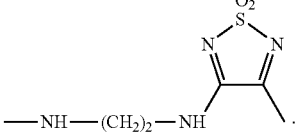

Other carbohydrate inhibitors by Magnani et al. are disclosed in U.S. Pat. No. 7,060,685, which is expressly incorporated herein by reference in their entirety. These compounds consist of a benzyl amino sulfonic acid (BASA) linked to a carbohydrate or a glycomimetic, wherein the carbohydrate or the glycomimetic binds a selectin; wherein the BASA is

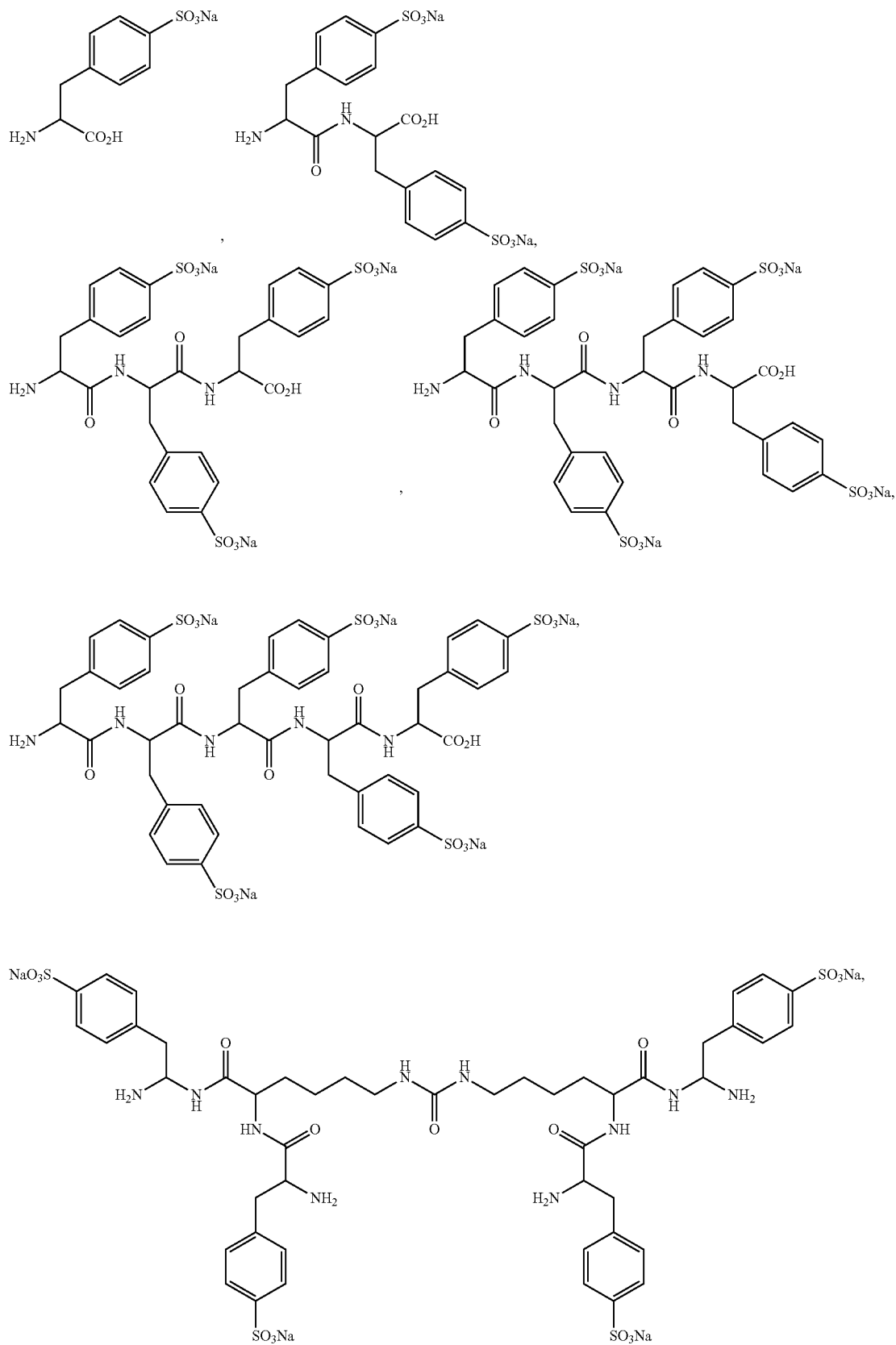

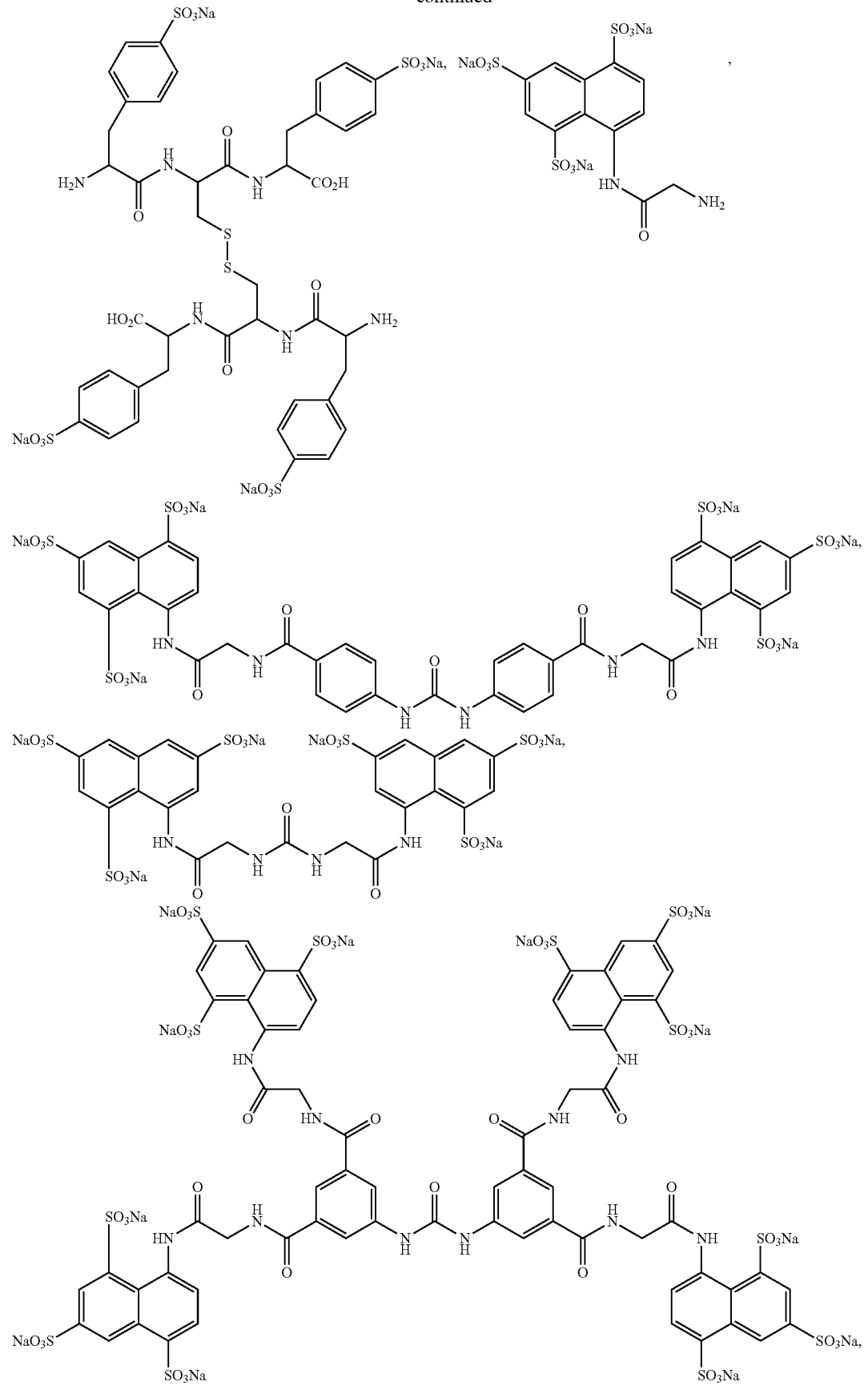

-continued
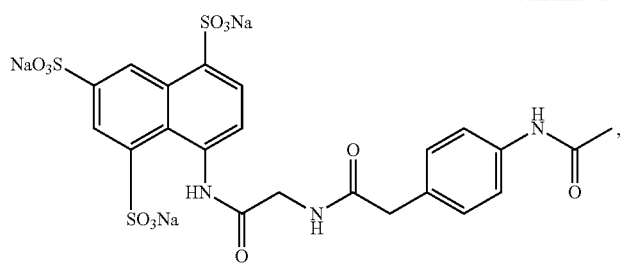
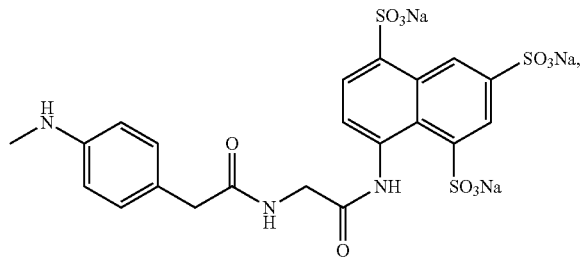
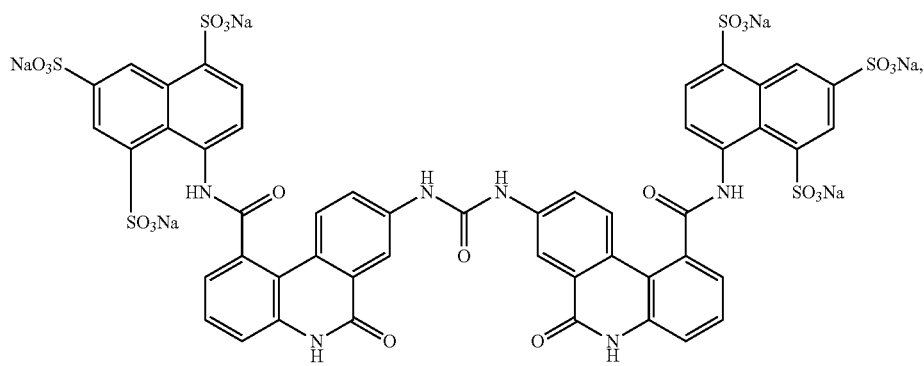
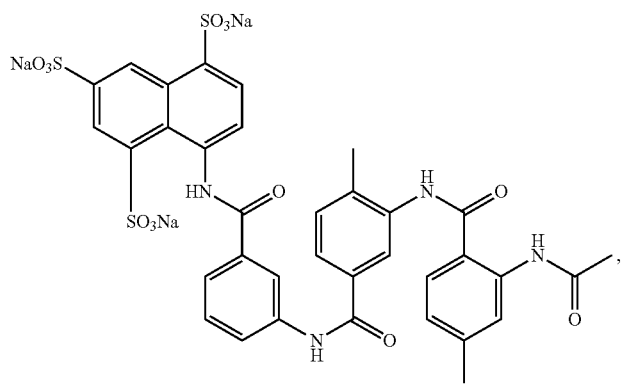
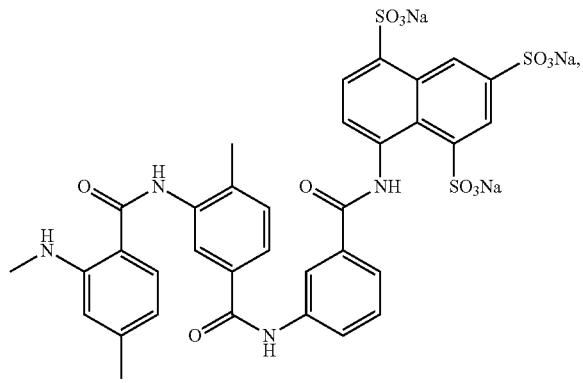

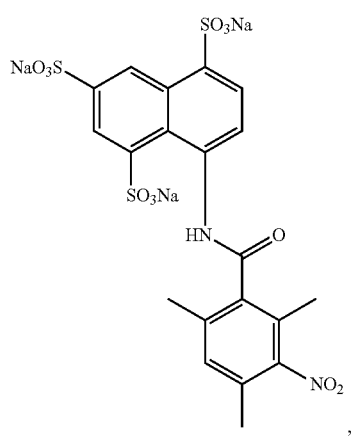
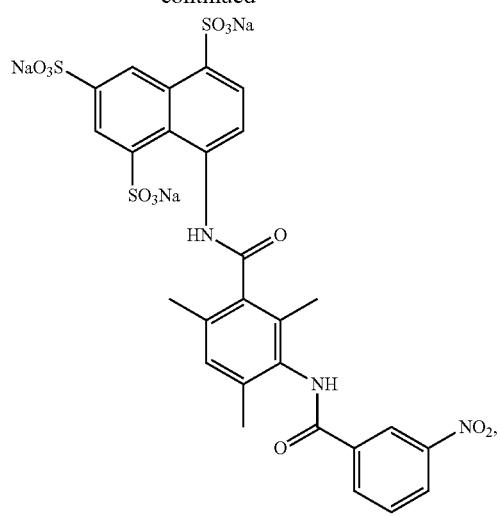
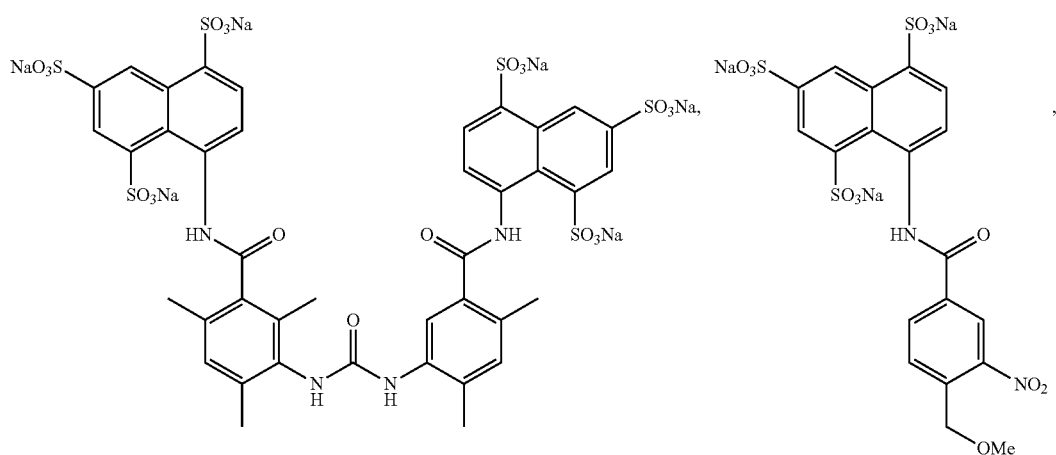
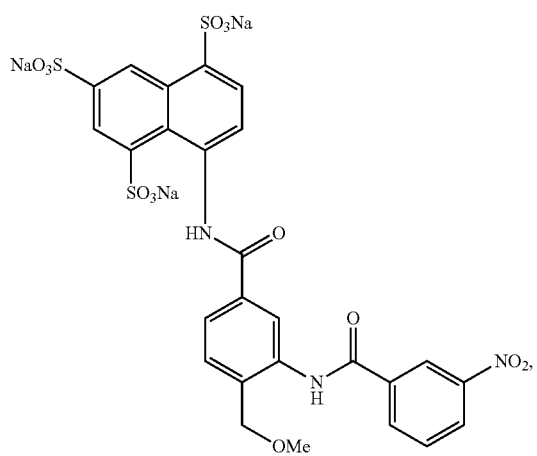

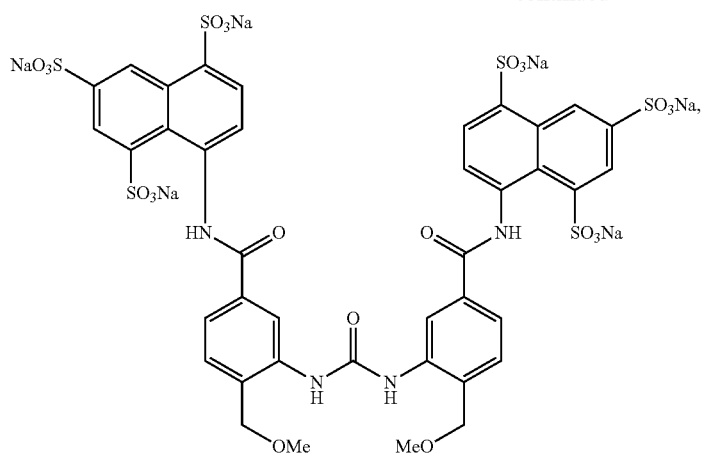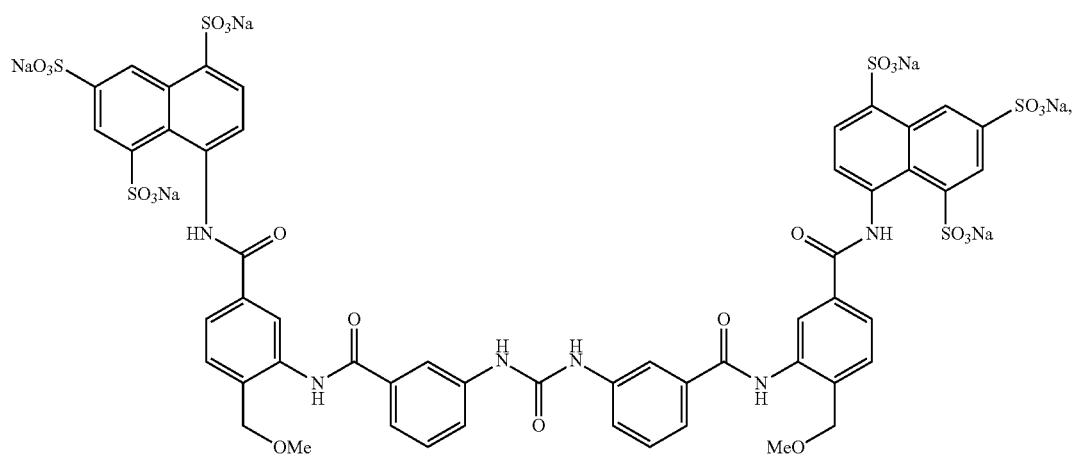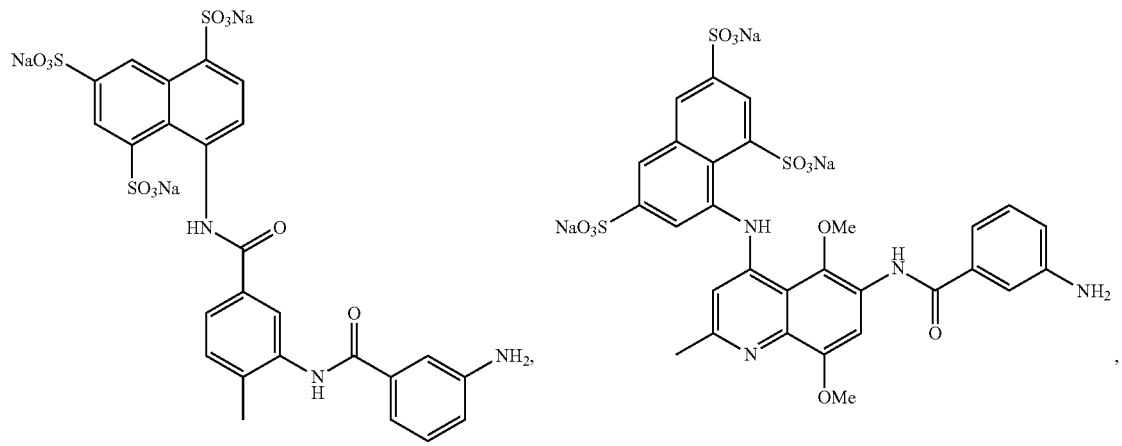

81
82
-continued
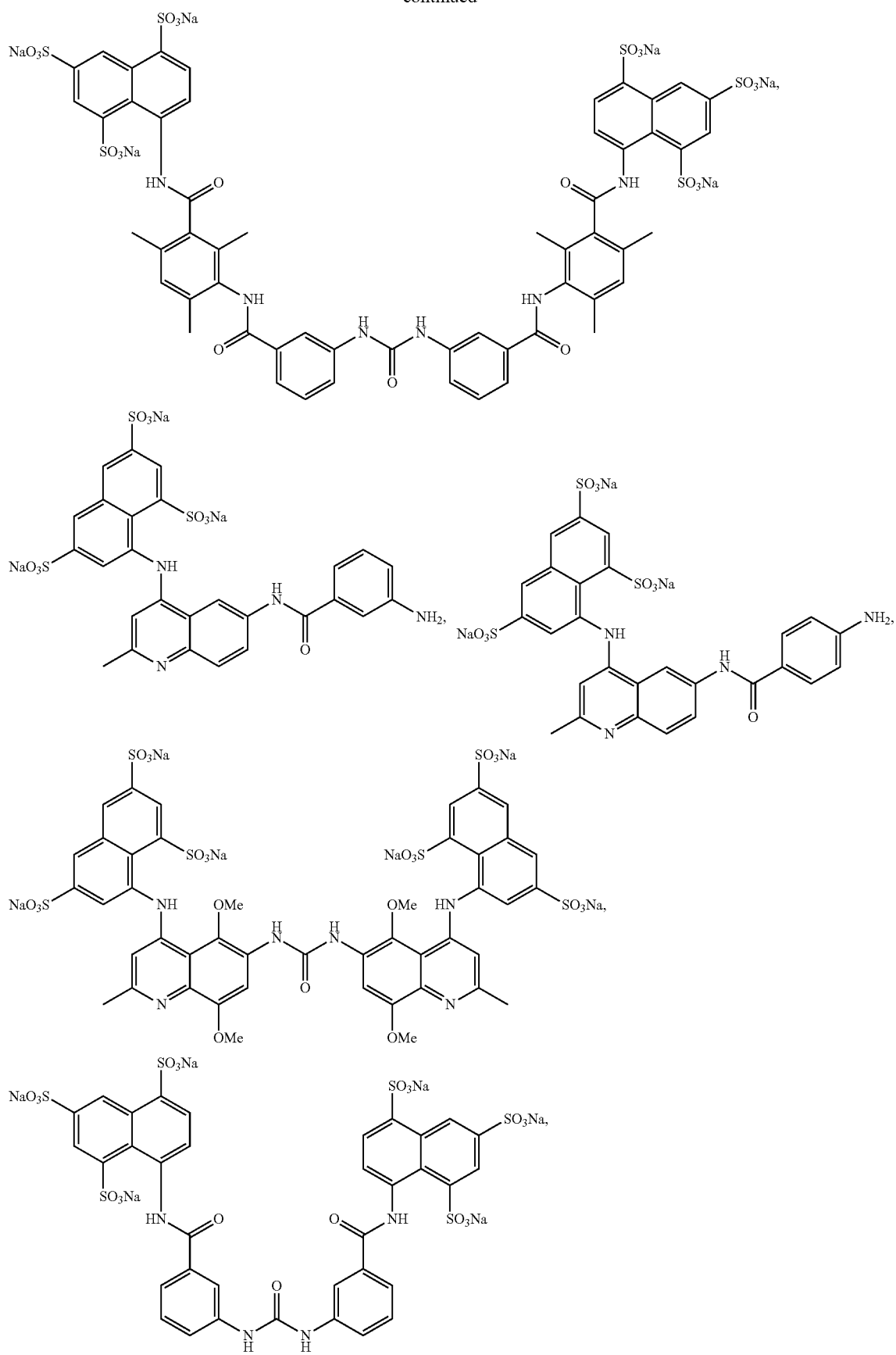

83 84
-continued
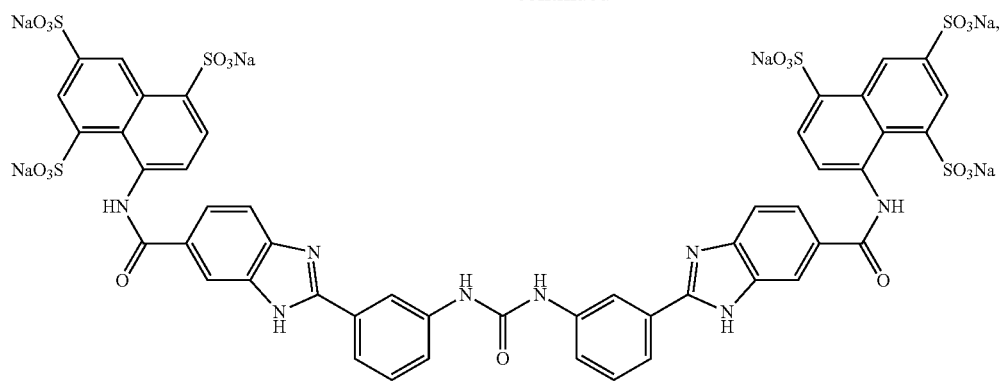
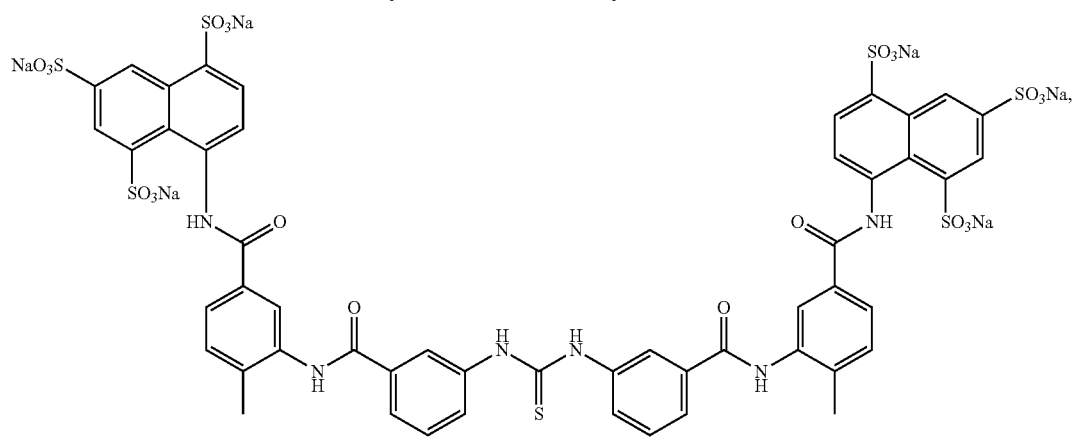
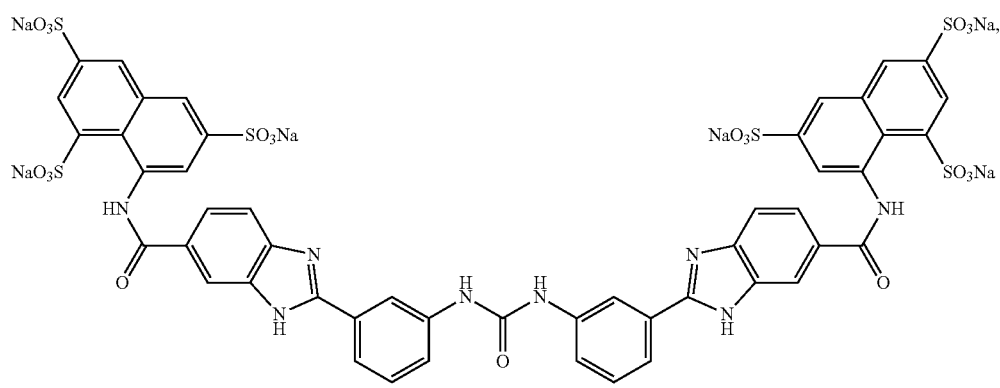
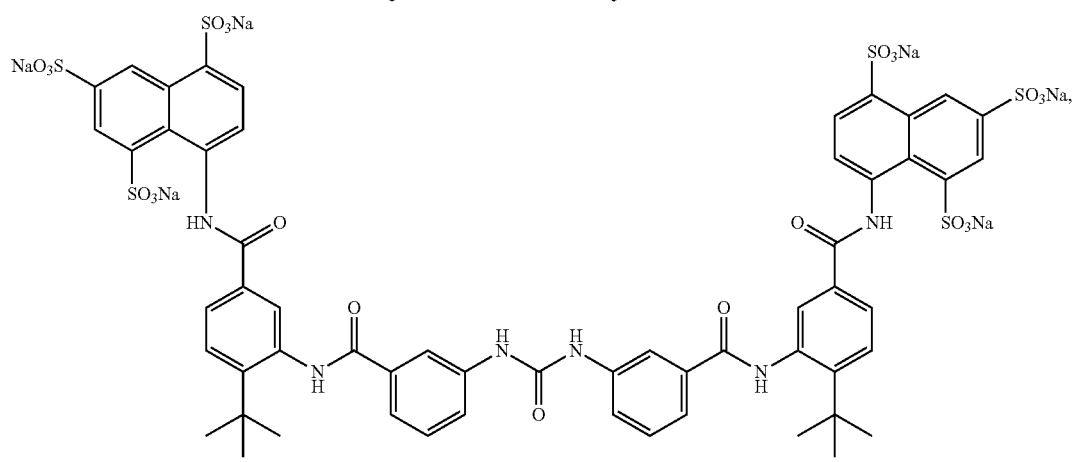

85
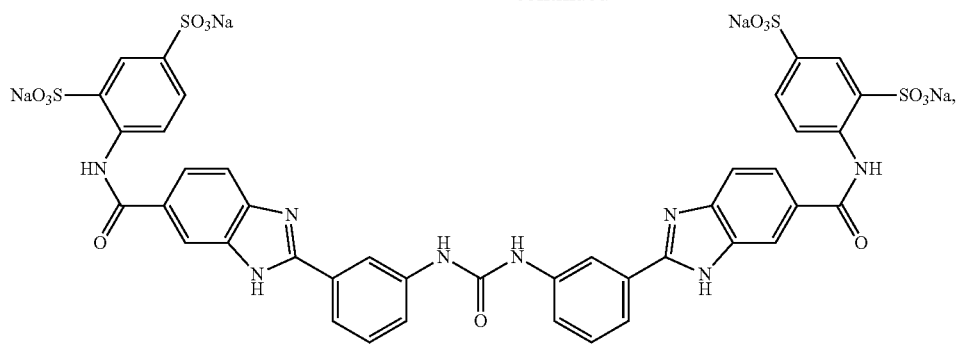
86
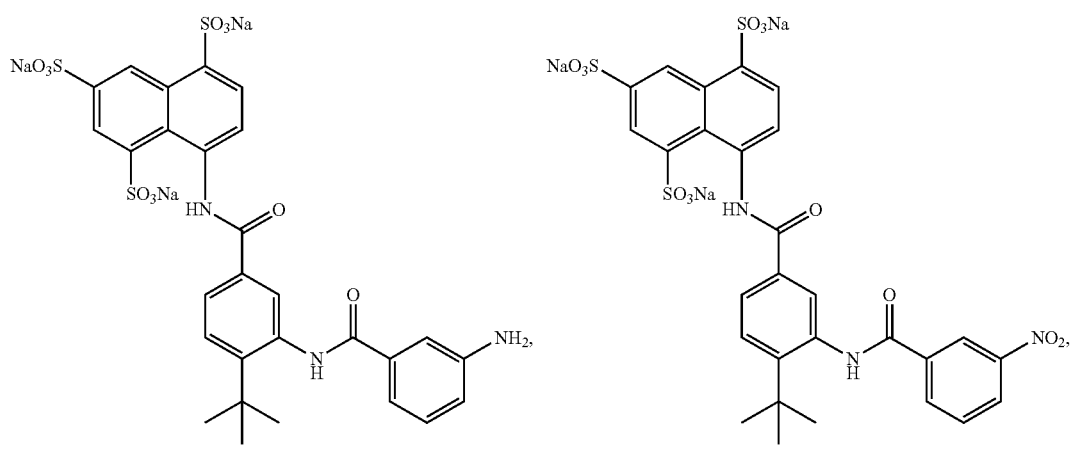
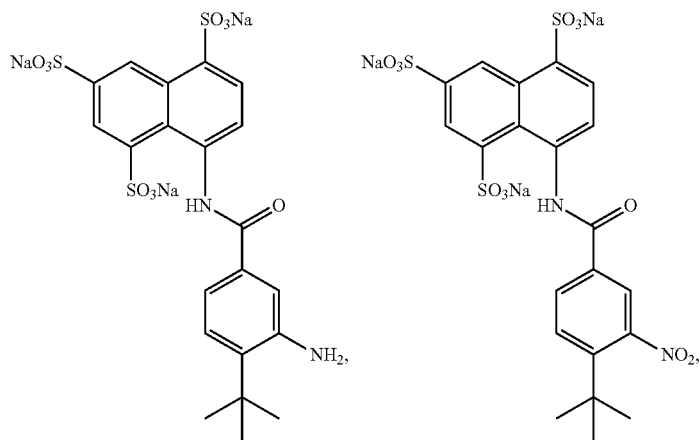
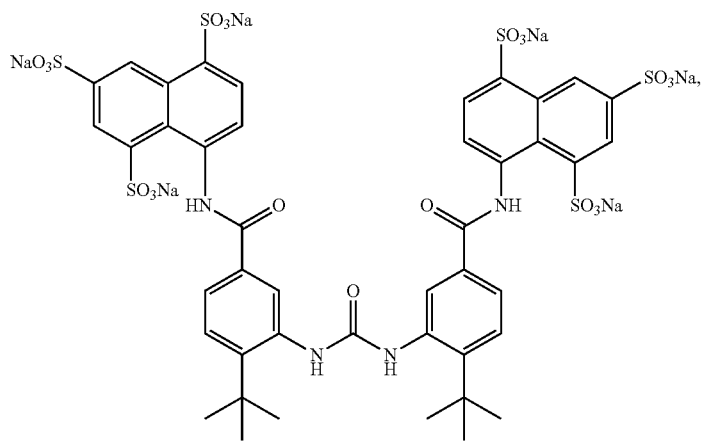

-continued
87 88
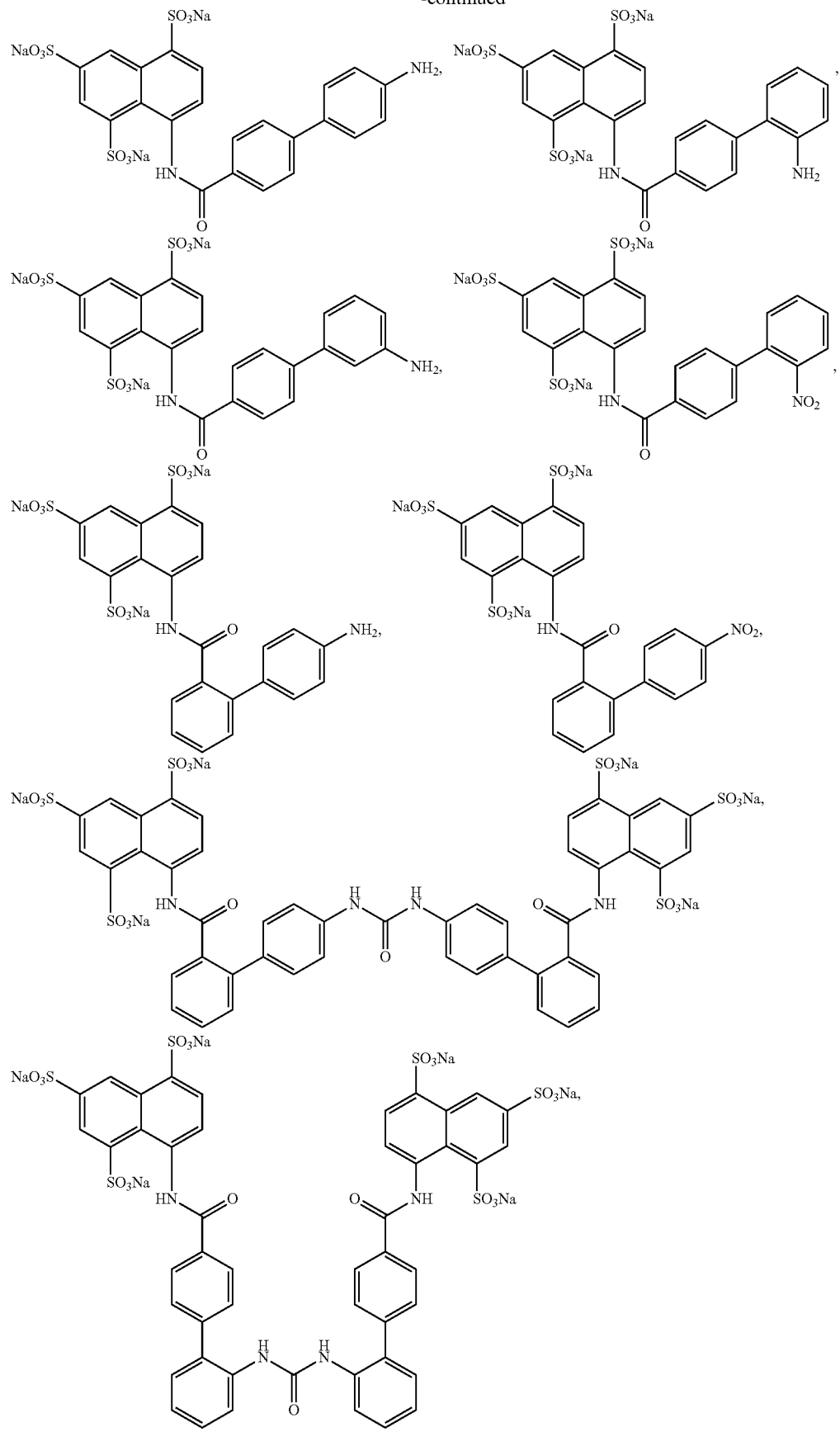

-continued
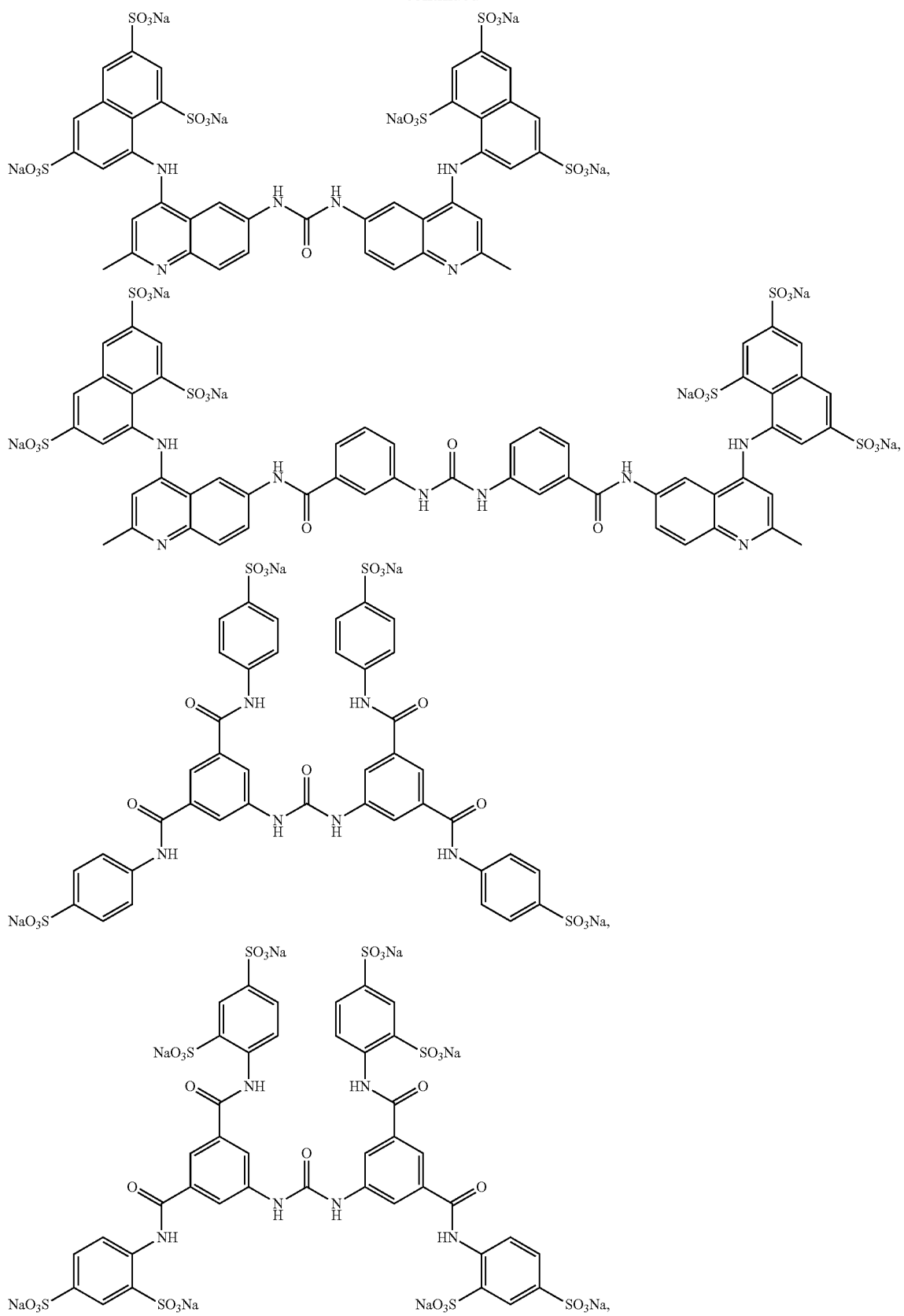

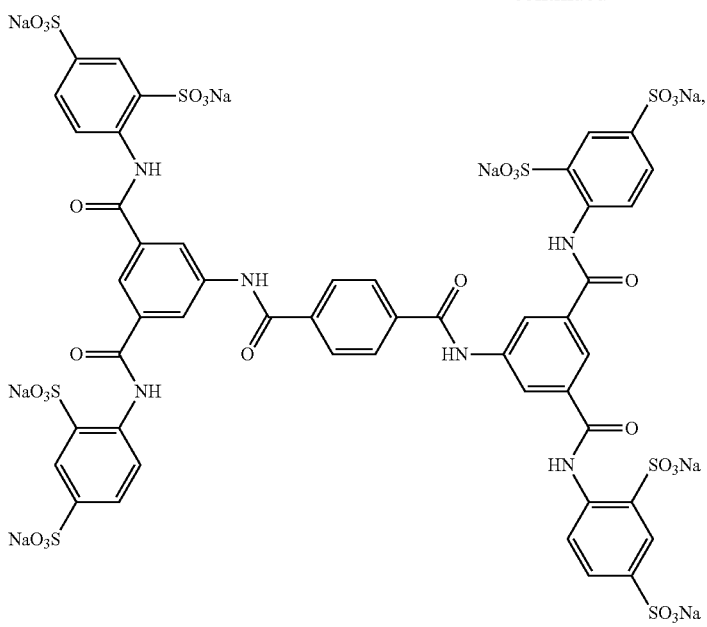
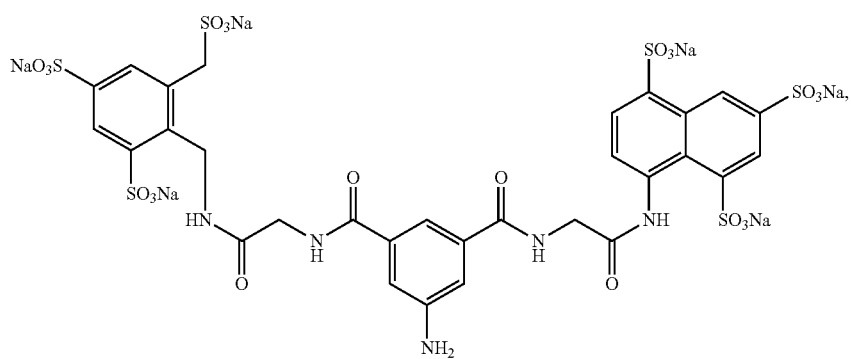
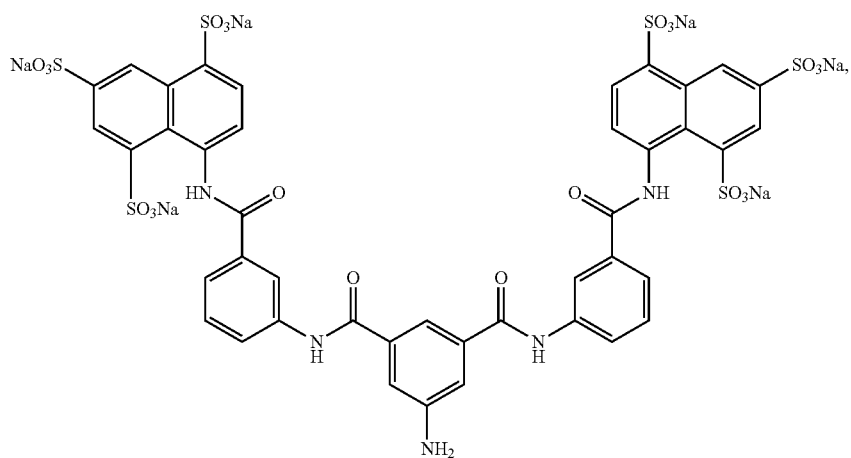

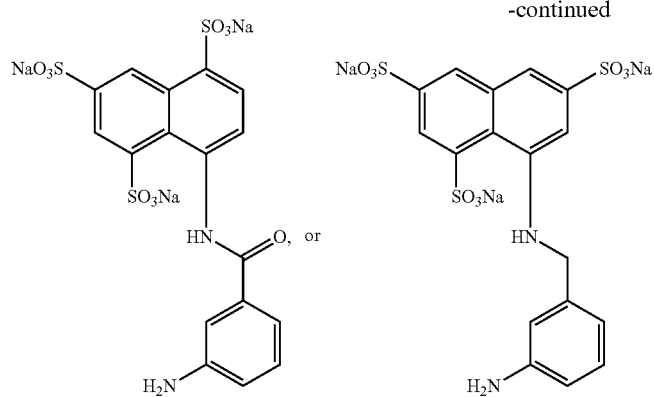
and wherein the carbohydrate or glycomimetic is:
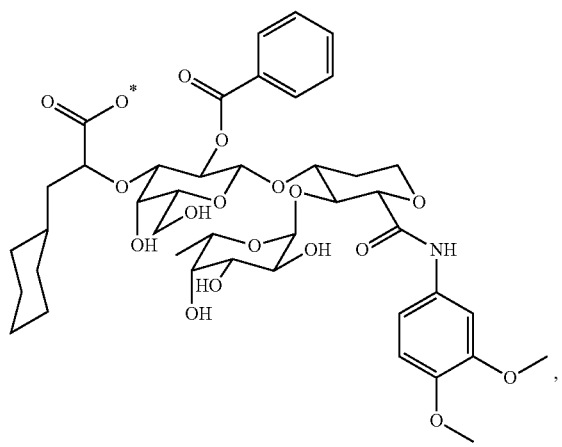
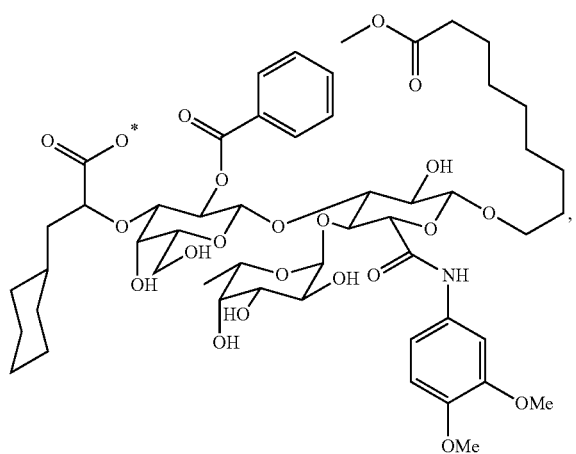

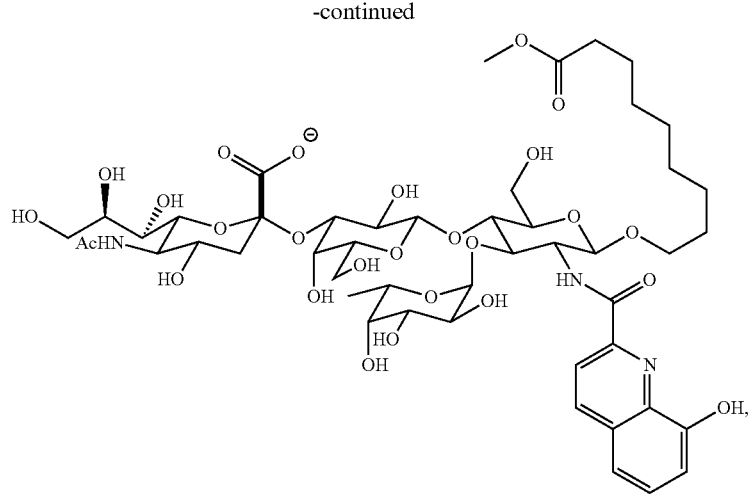
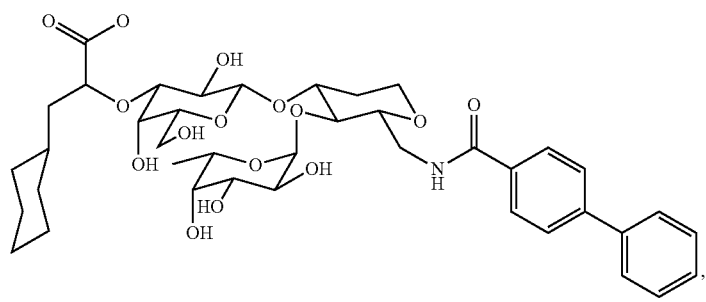
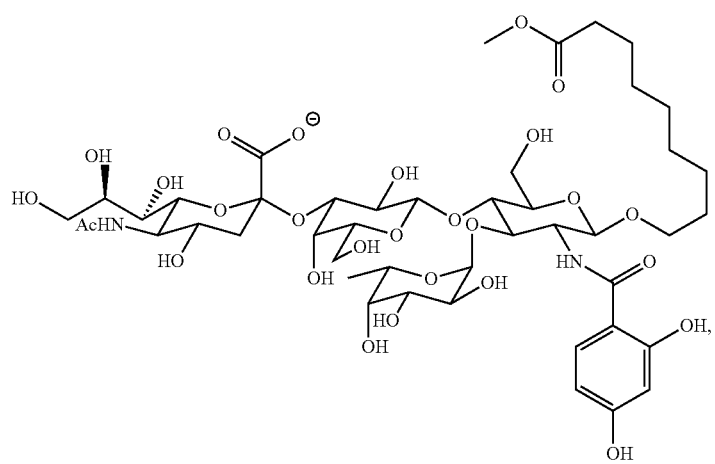
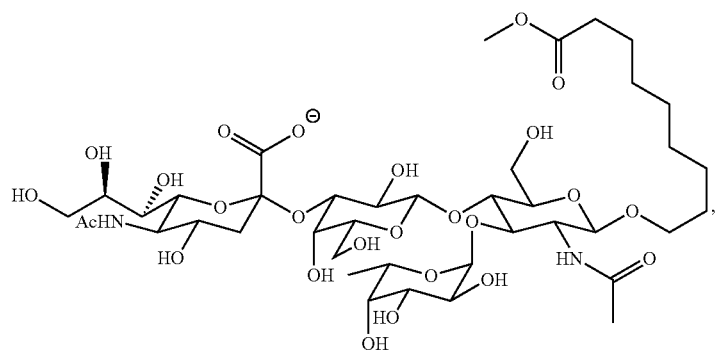

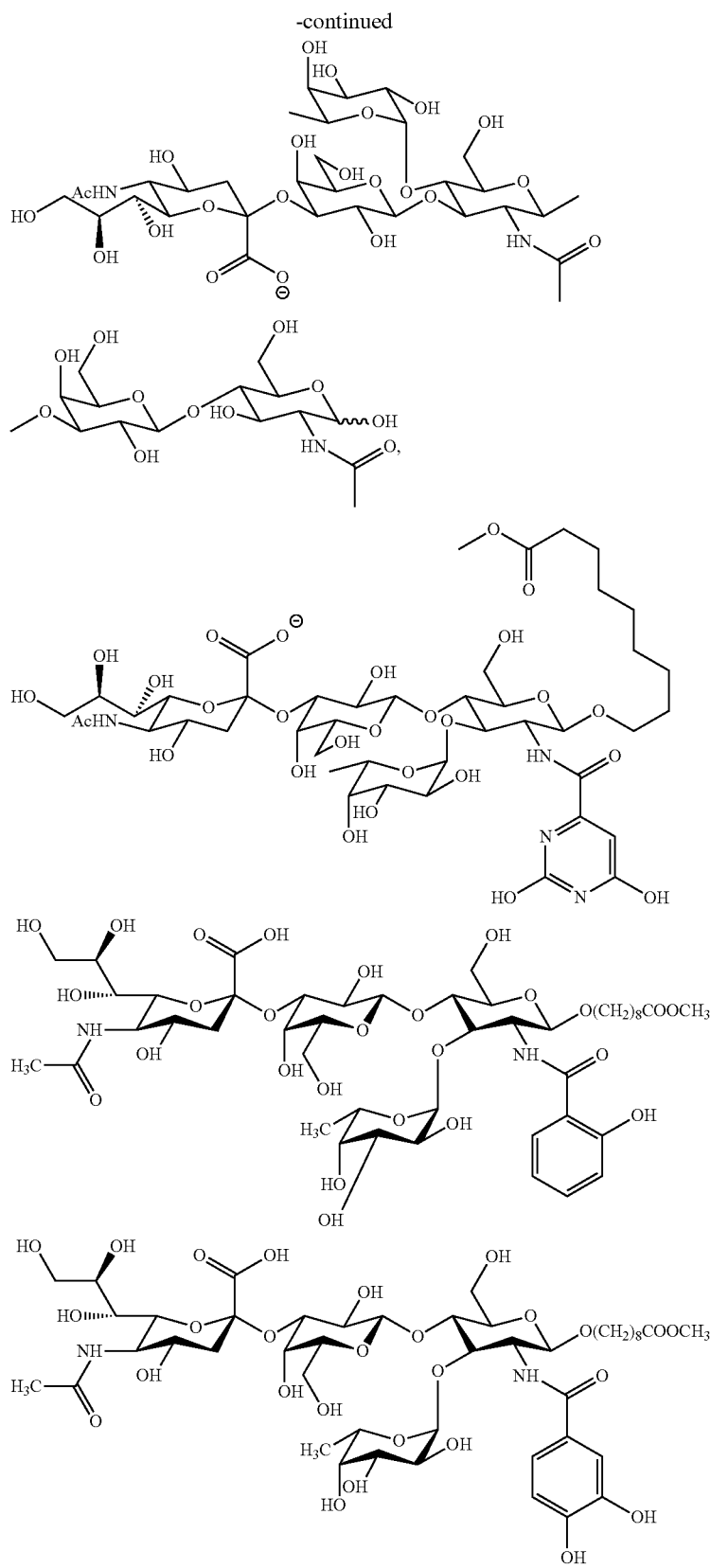

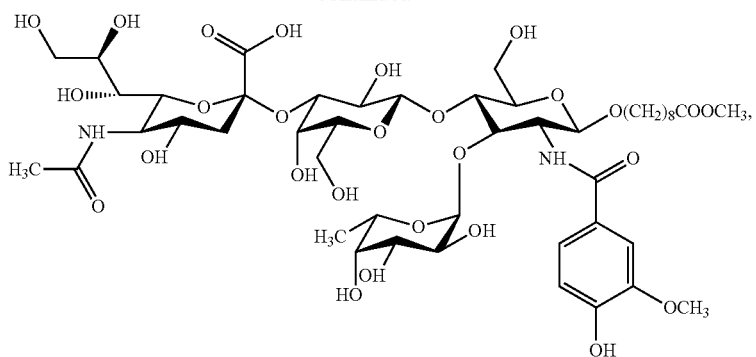
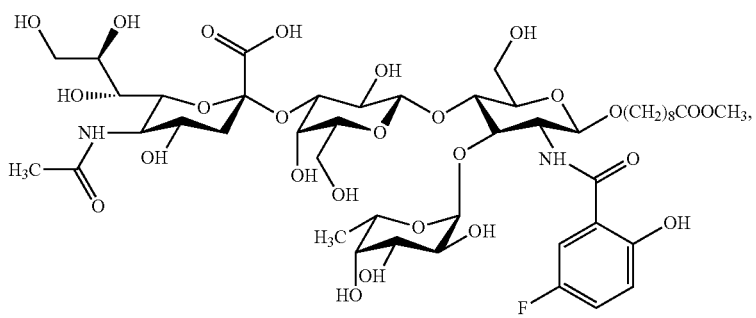
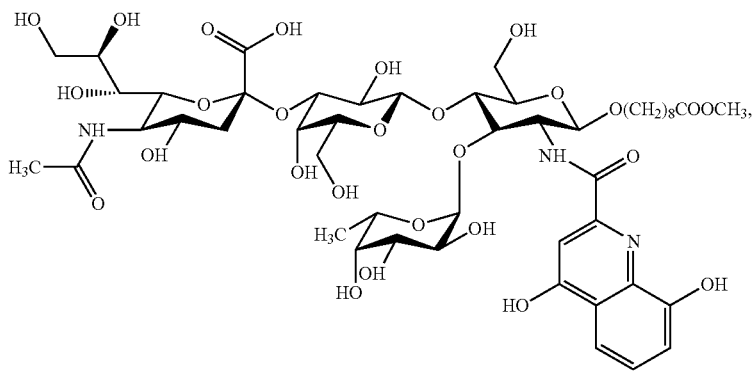
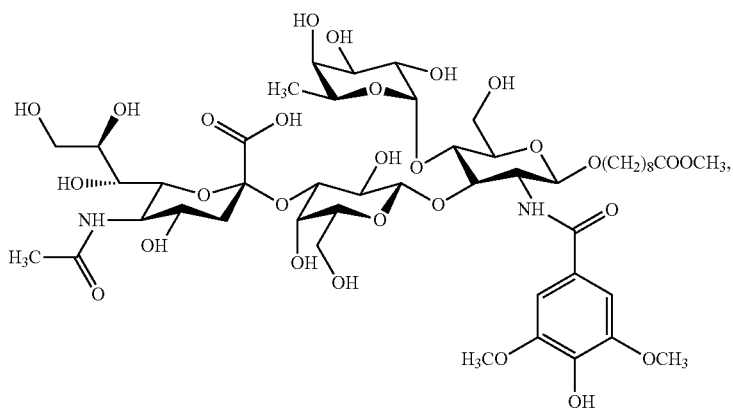

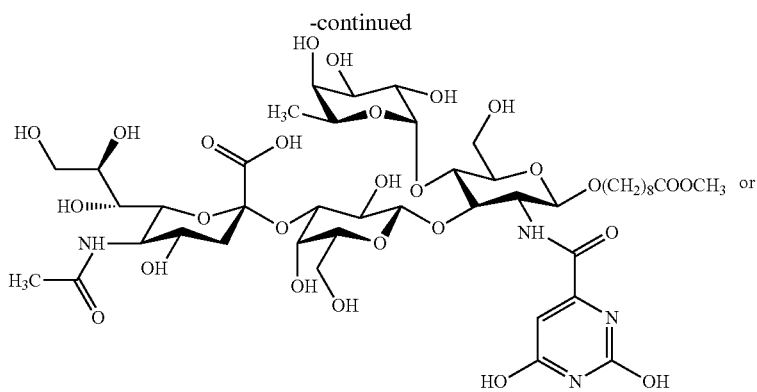
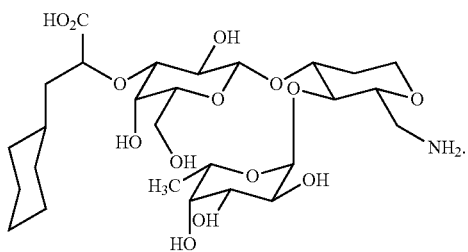
Non-limiting examples of such compounds include:
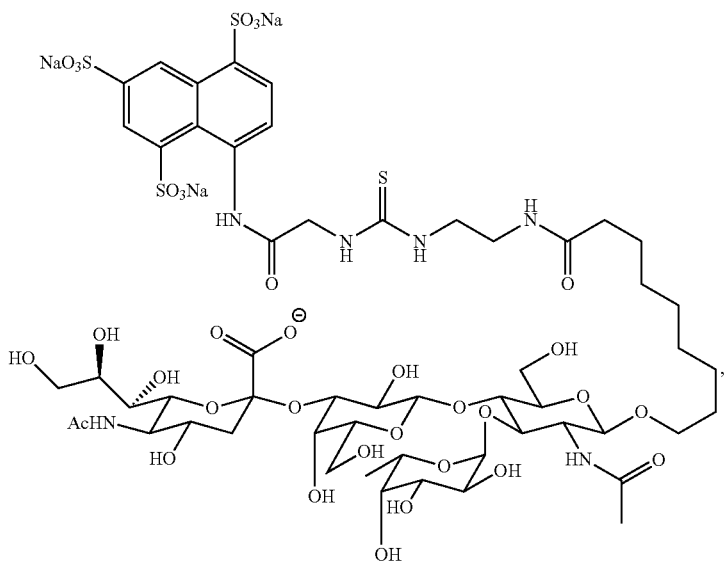

-continued
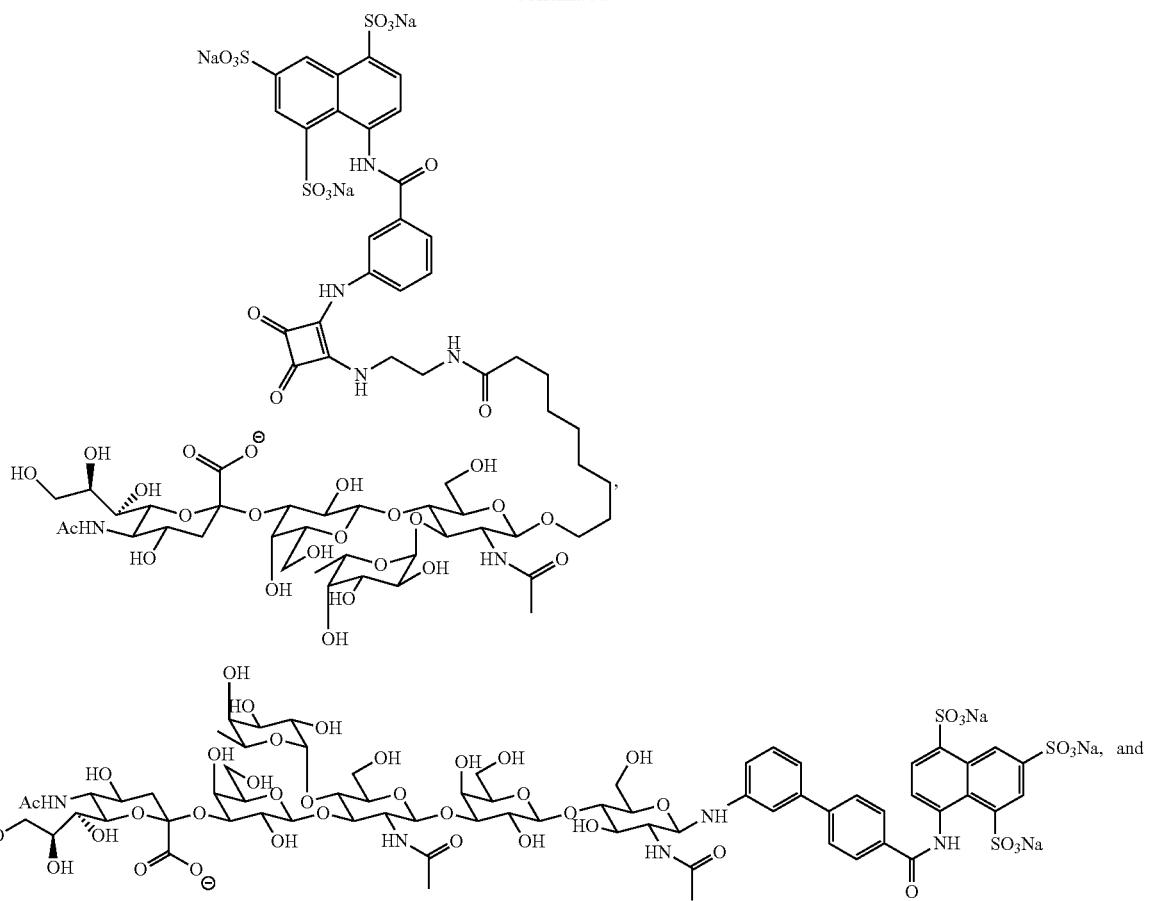
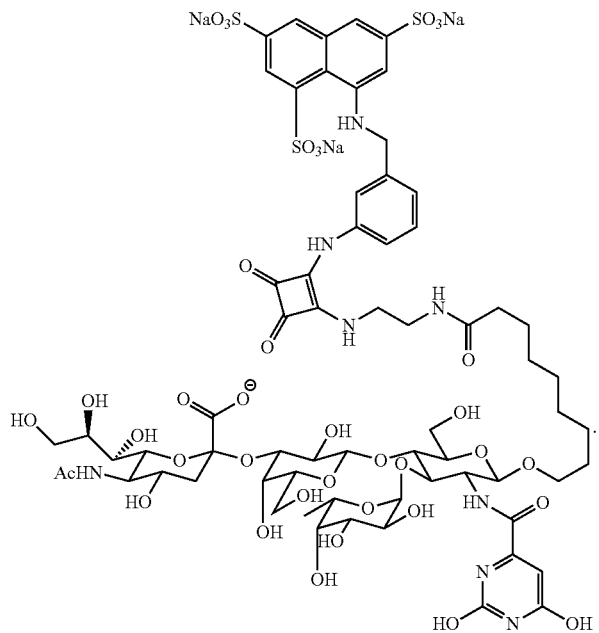

Still other carbohydrate inhibitors by Magnani et al. are disclosed in U.S. Pat. Nos. 6,121,233, 6,387,884 or 6,391,857, which are expressly incorporated herein by reference in their entirety. These compounds are represented by a formula selected from the group consisting of:

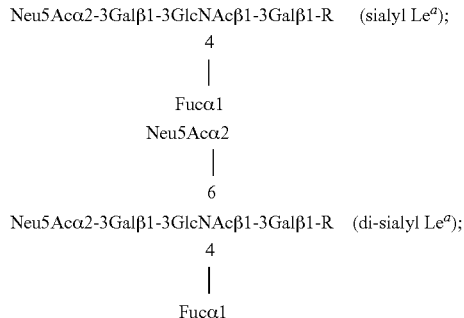

isomers of sialyl Le$^\alpha$ or di-sialyl Le$^\alpha$;

saccharides that include or consist of carbohydrate portions of sialyl Le$^\alpha$ or di-sialyl Le$^\alpha$; and glycoconjugates that include a carbohydrate portion of sialyl Le$^\alpha$ or di-sialyl Le$^\alpha$, wherein:

Neu5Ac represents sialic acid; Gal represents galactose; GlcNAc represents N-acetyl-glucosamine; Fuc represents fucose and R is typically a ceramide (with a glucose residue interposed) or a protein.

Illustrative examples of isomers of the above compounds include sialyl Le$^x$, which is an isomer of sialyl Le$^\alpha$ wherein the Gal-GlcNAc linkage is β1-4 and the Fuc-GlcNAc linkage is α1→3.

Representative saccharides include the carbohydrate portion of sialyl Le$^\alpha$ or di-sialyl Le$^\alpha$ (i.e., the above structures minus R), and derivatives of either, including those which cross-react with both sialyl Le$^\alpha$ and sialyl Le$^x$ Non-limiting examples of glycoconjugates may be represented by the following structures:

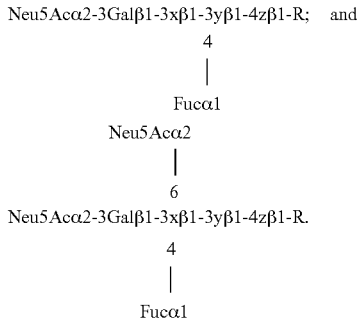

wherein:

R includes H, OH, lipid, ceramide, or one or more amino acids; x, y and z are independently selected from saccharides, or either y or z or both may be absent.

In still other embodiments, the carbohydrate inhibitor is selected from fluorinated glucosamine analogs as disclosed for example by Sackstein et al, in US Pat. Appl. Pub. No. 2006/0281708, which is expressly incorporated herein by reference in its entirety. Representative analogs of this type are fluorinated N-acetylglucosamines, illustrative examples of which include 2-acetamido-2-deoxy-1,3,6-tri-O-acetyl-4-deoxy-4-fluoro-D-glucopyranose and 2-acetamido-2-deoxy-1,4,6-tri-O-acetyl-3-deoxy-3-fluoro-D-glucopyranose.

In other illustrative examples, the carbohydrate inhibitor is selected from the compounds described by Ali et al. (FASEB J. 2004 January; 18(1):152-4.), which is expressly incorporated herein by reference in its entirety. Non-limiting examples of these compounds are polylysine-a sialyl Lewis$^x$ mimetic conjugates selected from:

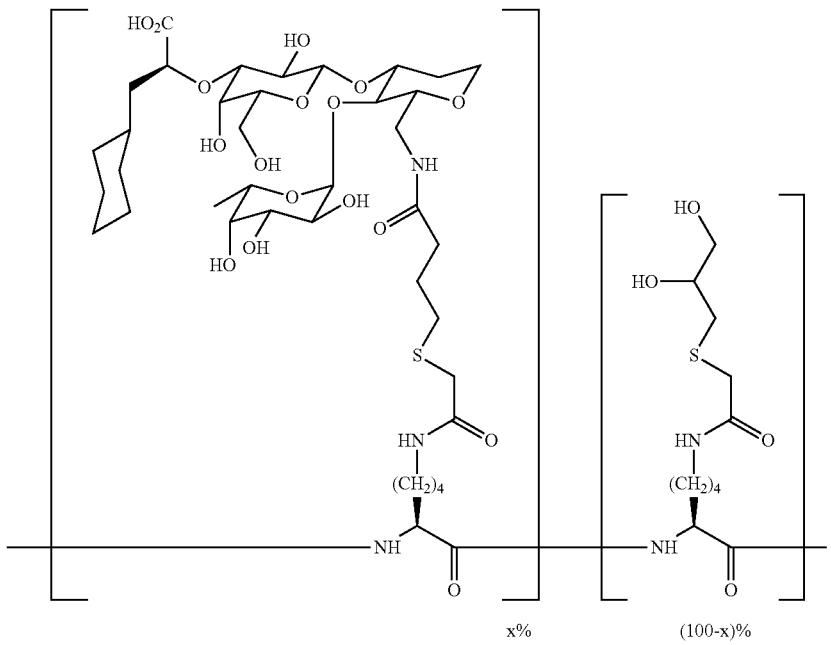

wherein x=1-100.

3. Identification of Target Molecule Modulators

The invention also features methods of screening for modulatory agents that reduce the level or functional activity of E-selectin for use in the therapeutic or prophylactic methods and compositions of the present invention. In some embodiments, the methods comprise: (1) contacting a preparation with a test agent, wherein the preparation contains (i) a polypeptide comprising an amino acid sequence corresponding to at least a biologically active fragment of an E-selectin polypeptide, or to a variant or derivative thereof; or (ii) a polynucleotide comprising at least a portion of a genetic sequence that regulates the level or functional activity of the E-selectin polypeptide, which is operably linked to a reporter gene; and (2) detecting a change in the level and/or functional activity of the E-selectin polypeptide, or an expression product of the reporter gene, relative to a normal or reference level and/or functional activity in the absence of the test agent, which indicates that the agent modulates the level or functional activity of the E-selectin.

Modulators falling within the scope of the present invention include antagonists of the level or functional activity of E-selectin, including antagonistic antigen-binding molecules, and inhibitor peptide fragments, antisense molecules, ribozymes, RNAi molecules and co-suppression molecules as well as carbohydrate inhibitors of E-selectin function, as for example described in Section 2

Candidate agents encompass numerous chemical classes, though typically they are organic molecules, preferably small organic compounds having a molecular weight of more than 50 and less than about 2,500 Dalton. Candidate agents comprise functional groups necessary for structural interaction with proteins, particularly hydrogen bonding, and typically include at least an amine, carbonyl, hydroxyl or carboxyl group, desirably at least two of the functional chemical groups. The candidate agent often comprises cyclical carbon or heterocyclic structures or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogues or combinations thereof.

Small (non-peptide) molecule modulators of a E-selectin polypeptide are particularly advantageous. In this regard, small molecules are desirable because such molecules are more readily absorbed after oral administration, have fewer potential antigenic determinants, or are more likely to cross the cell membrane than larger, protein-based pharmaceuticals. Small organic molecules may also have the ability to gain entry into an appropriate cell and affect the expression of a gene (eg by interacting with the regulatory region or transcription factors involved in gene expression); or affect the activity of a gene by inhibiting or enhancing the binding of accessory molecules.

Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc to produce structural analogues.

Screening may also be directed to known pharmacologically active compounds and chemical analogues thereof.

Screening for modulatory agents according to the invention can be achieved by any suitable method. For example, the method may include contacting a cell expressing a polynucleotide corresponding to an E-selectin gene with an agent suspected of having the modulatory activity and screening for the modulation of the level or functional activity of a protein encoded by the polynucleotide, or the modulation of the level of a transcript encoded by the polynucleotide, or the modulation of the activity or expression of a downstream cellular target of the protein or of the transcript (hereafter referred to as target molecules). Detecting such modulation can be achieved utilising techniques including, but not restricted to, ELISA, cell-based ELISA, inhibition ELISA, Western blots, immunoprecipitation, slot or dot blot assays, immunostaining, RIA, scintillation proximity assays, fluorescent immunoassays using antigen-binding molecule conjugates or antigen conjugates of fluorescent substances such as fluorescein or rhodamine, Ouchterlony double diffusion analysis, immunoassays employing an avidin-biotin or a streptavidin-biotin detection system, and nucleic acid detection assays including reverse transcriptase polymerase chain reaction (RT-PCR).

It will be understood that a polynucleotide from which an E-selectin polypeptide is regulated or expressed may be naturally occurring in the cell which is the subject of testing or it may have been introduced into the host cell for the purpose of testing. In addition, the naturally-occurring or introduced polynucleotide may be constitutively expressed—thereby providing a model useful in screening for agents which down-regulate expression of an encoded product of the sequence wherein the down regulation can be at the nucleic acid or expression product level. Further, to the extent that a polynucleotide is introduced into a cell, that polynucleotide may comprise the entire coding sequence that codes for an E-selectin polypeptide or it may comprise a portion of that coding sequence (e.g., the ligand-binding domain of an E-selectin polypeptide) or a portion that regulates expression of an E-selectin gene (e.g., an E-selectin promoter). For example, the promoter that is naturally associated with the polynucleotide may be introduced into the cell that is the subject of testing. In this instance, where only the promoter is utilized, detecting modulation of the promoter activity can be achieved, for example, by operably linking the promoter to a suitable reporter polynucleotide including, but not restricted to, green fluorescent protein (GFP), luciferase, β-galactosidase and catecholamine acetyl transferase (CAT). Modulation of expression may be determined by measuring the activity associated with the reporter polynucleotide.

These methods provide a mechanism for performing high throughput screening of putative modulatory agents such as proteinaceous or non-proteinaceous agents comprising synthetic, combinatorial, chemical and natural libraries. These methods will also facilitate the detection of agents which bind either the polynucleotide encoding the target molecule or which modulate the expression of an upstream molecule, which subsequently modulates the expression of the polynucleotide encoding the target molecule. Accordingly, these methods provide a mechanism of detecting agents that either directly or indirectly modulate the expression or activity of a target molecule according to the invention.

In some embodiments, the present invention provides assays for identifying small molecules or other compounds (i.e., modulatory agents) which are capable of inhibiting the level or functional activity of E-selectin. The assays may be performed in vitro using non-transformed cells, immortalized cell lines, or recombinant cell lines. In addition, the assays may detect the presence of increased or decreased expression of genes or production of proteins on the basis of increased or decreased mRNA expression (using, for example, nucleic acid probes that hybridise to an E-selectin gene or coding sequence), increased or decreased levels of E-selectin (using, for example, antigen binding molecules that are immuno-interactive with an E-selectin polypeptide), or increased or decreased levels of expression of a reporter gene (e.g., GFP, β-galactosidase or luciferase) operably linked to an E-selectin regulatory region (e.g., a promoter or enhancer) in a recombinant construct.

Thus, for example, one may culture cells which produce an E-selectin polypeptide and add to the culture medium one or more test compounds. After allowing a sufficient period of time (e.g., 6-72 hours) for the compound to inhibit the level or functional activity of the E-selectin polypeptide, any change in the level from an established baseline may be detected using, for example, any of the techniques described herein or known in the art. In specific embodiments, the cells are hemopoietic stem cells. Using suitable nucleic acid probes or antigen-binding molecules, detection of changes in the level and or functional activity of an E-selectin expression product, and thus identification of the compound as agonist or antagonist of the target molecule, requires only routine experimentation.

In some embodiments, recombinant assays are employed in which a reporter gene encoding, for example, GFP, β-galactosidase or luciferase is operably linked to the 5' regulatory regions of an E-selectin gene. Such regulatory regions may be easily isolated and cloned by one of ordinary skill in the art. The reporter gene and regulatory regions are joined in-frame (or in each of the three possible reading frames) so that transcription and translation of the reporter gene may proceed under the control of the regulatory elements of the E-selectin gene. The recombinant construct may then be introduced into any appropriate cell type although mammalian cells are desirable, and human cells are more desirable. The transformed cells may be grown in culture and, after establishing the baseline level of expression of the reporter gene, test compounds may be added to the medium. The ease of detection of the expression of the reporter gene provides for a rapid, high throughput assay for the identification of E-selectin antagonists of the invention.

Compounds identified by this method will have potential utility in modifying the expression of E-selectin in vivo. These compounds may be further tested in the animal models to identify those compounds having the most potent in vivo effects. In addition, as described above with respect to small molecules having target polypeptide binding activity, these molecules may serve as "lead compounds" for the further development of pharmaceuticals by, for example, subjecting the compounds to sequential modifications, molecular modelling, and other routine procedures employed in rational drug design.

In other embodiments, random peptide libraries consisting of a large number of possible combinations of amino acids attached to a solid phase support may be used to identify peptides that are able to bind to an E-selectin polypeptide or to a functional domain thereof. Identification of molecules that are able to bind to an E-selectin polypeptide may be accomplished by screening a peptide library with a recombinant soluble E-selectin polypeptide. The E-selectin polypeptide may be purified, recombinantly expressed or synthesised by any suitable technique. Such polypeptides may be conveniently prepared by a person skilled in the art using standard protocols as for example described in Sambrook, et al., (1989, supra) in particular Sections 16 and 17; Ausubel et al., ("Current Protocols in Molecular Biology", John Wiley & Sons Inc, 1994-1998), in particular Chapters 10 and 16; and Coligan et al., ("Current Protocols in Immunology", (John Wiley & Sons, Inc, 1995-1997), in particular Chapters 1, 5 and 6. Alternatively, an E-selectin polypeptide or a portion thereof may be synthesized using solution synthesis or solid phase synthesis as described, for example, in Chapter 9 of Atherton and Shephard (supra) and in Roberge et al (1995, Science 269: 202).

To identify and isolate the peptide/solid phase support that interacts and forms a complex with the E-selectin polypeptide it may be necessary to label or "tag" the E-selectin polypeptide. In this regard, the E-selectin polypeptide can be conjugated to any suitable reporter molecule, including enzymes such as alkaline phosphatase and horseradish peroxidase and fluorescent reporter molecules such as fluorescein isothiocyanate (FITC), phycoerythrin (PE) and rhodamine. Conjugation of any given reporter molecule, with an E-selectin polypeptide, may be performed using techniques that are routine in the art. Alternatively, E-selectin expression vectors may be engineered to express a chimeric E-selectin polypeptide containing an epitope for which a commercially available antigen-binding molecule exists. The epitope specific antigen-binding molecule may be tagged using methods known in the art including labeling with enzymes, fluorescent dyes or coloured or magnetic beads.

For example, the "tagged" E-selectin polypeptide conjugate is incubated with the random peptide library for 30 minutes to one hour at 22° C. to allow complex formation between E-selectin polypeptide and peptide species within the library. The library is then washed to remove any unbound E-selectin polypeptide. If the E-selectin polypeptide has been conjugated to alkaline phosphatase or horseradish peroxidase the whole library is poured into a petri dish containing a substrate for either alkaline phosphatase or peroxidase, for example, 5-bromo-4-chloro-3-indoyl phosphate (BCIP) or 3,3',4,4"-diamnobenzidine (DAB), respectively. After incubating for several minutes, the peptide/solid phase-E-selectin polypeptide complex changes color, and can be easily identified and isolated physically under a dissecting microscope with a micromanipulator. If a fluorescently tagged E-selectin polypeptide has been used, complexes may be isolated by fluorescent activated sorting. If a chimeric target polypeptide having a heterologous epitope has been used, detection of the peptide/E-selectin polypeptide complex may be accomplished by using a labeled epitope specific antigen-binding molecule. Once isolated, the identity of the peptide attached to the solid phase support may be determined by peptide sequencing.

4. Therapeutic and Prophylactic Uses

In accordance with the present invention, it is proposed that agents that antagonize E-selectin function are useful as actives for reducing or abrogating hematopoetic stem cell turnover and thus find utility in the treatment or prophylaxis of immunocompromised conditions resulting from medical treatment that target hematopoeitic stem cells, such as treatments that target rapidly dividing cells or that disrupt the cell cycle or cell division. The E-selectin antagonist may be used therapeutically after the medical treatment or may be used prophylactically before the treatment is administered or together with the medical treatment. Accordingly, the present invention contemplates combination therapy and prophylaxis which employ both an E-selectin antagonist and a medical treatment that induces an immunocompromised condition.

It is well known that chemotherapy and radiation therapy target rapidly dividing cells and/or disrupt the cell cycle or cell division. These treatments are offered as part of the treating several forms of cancer and autoimmune disease, aiming either at slowing their progression or reversing the symptoms of disease by means of a curative treatment. In some embodiments, therefore, the combination therapy or prophylaxis will employ an E-selectin antagonist and a chemotherapeutic agent, which is suitable selected from cytostatic agents and cytotoxic agents. Non-limiting examples of cytostatic agents are selected from: (1) microtubule-stabilizing agents such as but not limited to taxanes, paclitaxel, docetaxel, epothilones and laulimalides; (2) kinase inhibitors, illustrative examples of which include Iressa®, Gleevec, Tarceva™, (Erlotinib HCl), BAY-43-9006, inhibitors of the split kinase domain receptor tyrosine kinase subgroup (e.g., PTK787/ZK 222584 and SU11248); (3) receptor kinase targeted antibodies, which include, but are not limited to, Trastuzumab (Herceptin®), Cetuximab (Erbitux®), Bevacizumab (Avastin™), Rituximab (Ritusan®), Pertuzumab (Omnitarg™); (4) mTOR pathway inhibitors, illustrative examples of which include rapamycin and CCI-778; (5) Apo2L/Trail, anti-angiogenic agents such as but not limited to endostatin, combrestatin, angiostatin, thrombospondin and vascular endothelial growth inhibitor (VEGI); (6) antineoplastic immunotherapy vaccines, representative examples of which include activated T-cells, non-specific immune boosting agents (i.e., interferons, interleukins); (7) antibiotic cytotoxic agents such as but not limited to doxorubicin, bleomycin, dactinomycin, daunorubicin, epirubicin, mitomycin and mitozantrone; (8) alkylating agents, illustrative examples of which include Melphalan, Carmustine, Lomustine, Cyclophosphamide, Ifosfamide, Chlorambucil, Fotemustine, Busulfan, Temozolomide and Thiotepa; (9) hormonal antineoplastic agents, non-limiting examples of which include Nilutamide, Cyproterone acetate, Anastrozole, Exemestane, Tamoxifen, Raloxifene, Bicalutamide, Amino glutethimide, Leuprorelin acetate, Toremifene citrate, Letrozole, Flutamide, Megestrol acetate and Goserelin acetate; (10) gonadal hormones such as but not limited to Cyproterone acetate and Medoxyprogesterone acetate; (11) antimetabolites, illustrative examples of which include Cytarabine, Fluorouracil, Gemcitabine, Topotecan, Hydroxyurea, Thioguanine, Methotrexate, Colaspase, Raltitrexed and Capicitabine; (12) anabolic agents, such as but not limited to, Nandrolone; (13) adrenal steroid hormones, illustrative examples of which include Methylprednisolone acetate, Dexamethasone, Hydrocortisone, Prednisolone and Prednisone; (14) neoplastic agents such as but not limited to Irinotecan, Carboplatin, Cisplatin, Oxaliplatin, Etoposide and Dacarbazine; and (15) topoisomerase inhibitors, illustrative examples of which include topotecan and irinotecan.

Illustrative cytotoxic agents can be selected from sertenef, cachectin, ifosfamide, tasonermin, lonidamine, carboplatin, altretamine, prednimustine, dibromodulcitol, ranimustine, fotemustine, nedaplatin, oxaliplatin, temozolomide (TEMODAR™ from Schering-Plough Corporation, Kenilworth, N.J.), cyclophosphamide, heptaplatin, estramustine, improsulfan tosilate, trofosfamide, nimustine, dibrospidium chloride, pumitepa, lobaplatin, satraplatin, profiromycin, cisplatin, doxorubicin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[di-amine(chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deansino-3'-morpholino-13-deoxo-10-hydroxycaminomycin, annamycin, galarubicin, elinafide, MEN10755, 4-demethoxy-3-deamino-3-aziridinyl-4-methylsulphonyl-daunombicin (see International Publication WO 00/50032), methoxtrexate, gemcitabine, and mixture thereof.

In some embodiments, the E-selectin antagonist is used in combination with radiotherapies, such as but not limited to, conformal external beam radiotherapy (10-100 Grey given as fractions over 4-8 weeks), either single shot or fractionated, high dose rate brachytherapy, permanent interstitial brachytherapy, systemic radio-isotopes (e.g., Strontium 89). In illustrative examples of this type, the radiotherapy administered in combination with a radiosensitizing agent. Illustrative examples of radiosensitizing agents include but are not limited to efaproxiral, etanidazole, fluosol, misonidazole, nimorazole, temoporfin and tirapazamine.

Immunocompromised conditions generally lead to pathogenic infections and thus the present invention also extends to the treatment and/or prophylaxis of infections in individuals suffering from an immunocompromised condition, or to treatment of individuals who are likely to contract such a condition due to treatment known to be associated with the occurrence of an immunocompromised condition. Accordingly, an immunocompromised condition arising from a medical treatment is likely to expose the individual in question to a higher risk of infection. It is possible according to the invention to prophylactically treat an infection in an individual having the immunocompromised condition before or during treatments known to generate such a condition. By prophylactically treating with an E-selectin antagonist before or during a treatment known to generate an immunocompromised condition it is possible to prevent a subsequent infection or to reduce the risk of the individual contracting an infection manifesting from that condition. In some embodiments, therefore, the present invention extends to combination therapies or preventatives, which employ both an E-selectin antagonist and an anti-infective agent that is effective against an infection that develops or that has an increased risk of developing from an immunocompromised condition resulting from a medical treatment as broadly described above.

The anti-infective drugs is suitably selected from antimicrobials, which include without limitation compounds that kill or inhibit the growth of microorganisms such as viruses, bacteria, yeast, fungi, protozoa, etc. and thus include antibiotics, amebicides, antifungals, antiprotozoals, antimalarials, antituberculotics and antivirals. Anti-infective drugs also include within their scope anthelmintics and nematocides. Illustrative antibiotics include quinolones (e.g., amifloxacin, cinoxacin, ciprofloxacin, enoxacin, fleroxacin, flumequine, lomefloxacin, nalidixic acid, norfloxacin, ofloxacin, levofloxacin, lomefloxacin, oxolinic acid, pefloxacin, rosoxacin, temafloxacin, tosufloxacin, sparfloxacin, clinafloxacin, gatifloxacin, moxifloxacin; gemifloxacin; and garenoxacin), tetracyclines, glycylcyclines and oxazolidinones (e.g., chlortetracycline, demeclocycline, doxycycline, lymecycline, methacycline, minocycline, oxytetracycline, tetracycline, tigecycline; linezolide, eperozolid), glycopeptides, aminoglycosides (e.g., amikacin, arbekacin, butirosin, dibekacin, fortimicins, gentamicin, kanamycin, meomycin, netilmicin, ribostamycin, sisomicin, spectinomycin, streptomycin, tobramycin), β-lactams (e.g., imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefinetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763), rifamycins, macrolides (e.g., azithromycin, clarithromycin, erythromycin, oleandomycin, rokitamycin, rosaramicin, roxithromycin, troleandomycin), ketolides (e.g., telithromycin, cethromycin), coumermycins, lincosamides (e.g., clindamycin, lincomycin) and chloramphenicol.

Illustrative antivirals include abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, and zidovudine.

Non-limiting examples of amebicides or antiprotozoals include atovaquone, chloroquine hydrochloride, chloroquine phosphate, metronidazole, metronidazole hydrochloride, and pentamidine isethionate. Anthelmintics can be at least one selected from mebendazole, pyrantel pamoate, albendazole, ivermectin and thiabendazole. Illustrative antifungals can be selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, and terbinafine hydrochloride. Non-limiting examples of antimalarials include chloroquine hydrochloride, chloroquine phosphate, doxycycline, hydroxychloroquine sulfate, mefloquine hydrochloride, primaquine phosphate, pyrimethamine, and pyrimethamine with sulfadoxine. Antituberculotics include but are not restricted to clofazimine, cycloserine, dapsone, ethambutol hydrochloride, isoniazid, pyrazinamide, rifabutin, rifampin, rifapentine, and streptomycin sulfate.

It is also known that medical treatments that target rapidly dividing cells and/or disrupt the cell cycle or cell division (e.g., chemotherapy and radiation therapy) are immunocompromising since cells of the immune system including hematopoeitic cells are destroyed or substantially reduced in number, thus leading to a state of immunosuppression characterized by neutropenia, agranulocytosis, thrombocytopenia and/or anemia. Accordingly, the present invention finds particular utility in the treatment or prophylaxis of any one or more of these conditions that manifest from a medical treatment as broadly noted above.

Anemia, thrombocytopenia, neutropenia and agranulocytosis are frequently defined in terms of laboratory measurements indicating a reduced hematocrit (volume percent), a reduced platelet count (per $mm^3$), a reduced neutrophil count (per $mm^3$), a reduced total granulocyte (i.e., neutrophils, basophils and eosinophils) or white blood cell count (per $mm^3$), respectively. Methods of determining these values are well known in the art, including automated as well as manual methods. The lower limits of normal for hematocrits and platelet counts in healthy nonpregnant humans is somewhat variable, depending on the age and sex of the subject, method of determination, and the norms for the laboratory performing the measurements. Generally, however, an adult human subject is said to have anemia when the hematocrit is less than about 37-40%. Likewise, generally an adult human subject is said to have thrombocytopenia when the platelet count is below about 100,000 per $mm^3$. Anemia is also frequently reported in terms of a reduced hemoglobin (g/dL) or red blood cell count (per $mm^3$). Typical lower limits of normal values for these in healthy adult humans are 12-13 g/dL and about $4.1 \times 10^6$ per $mm^3$, respectively. Generally an adult human subject is said to have neutropenia when the neutrophil count falls below 1000 per $mm^3$. Additionally, an adult human is generally said to have agranulocytosis when the total granulocyte cell count falls below 500 cells/$mm^3$. Corresponding values for all these parameters are different for other species.

Hematopoeitic disorders such as anemia, thrombocytopenia, neutropenia and agranulocytosis are also frequently associated with clinical signs and symptoms in relation to their degree of severity. Anemia may be manifested as pallor, generalized fatigue or weakness, reduced exercise tolerance, shortness of breath with exertion, rapid heart rate, irregular heart rhythm, chest pain (angina), congestive heart failure, and headache. Thrombocytopenia is typically manifested in terms of spontaneous or uncontrolled bleeding, petechiae, and easy bruising. Neutropenia is associated with infections, including notably infections from endogenous microbial flora, and lack of inflammation.

Accordingly, the present invention contemplates combination therapy and prophylaxis which employ both an E-selectin antagonist and an ancillary treatment that treats a hematopoeitic disorder as broadly described above. In some embodiments, the combination therapy or prophylaxis will employ an E-selectin antagonist and a medicament selected from an anemia medicament, a thrombocytopenia medicament, an agranulocytosis medicament or a neutropenia medicament, illustrative examples of which include steroids, inducers of steroids, and immunomodulators.

The steroids include, but are not limited to, systemically administered corticosteroids including methylprednisolone, prednisolone and prednisone, cortisone, and hydrocortisone. Inducers of steroids include, but are not limited to adrenocorticotropic hormone (ACTH).

Corticosteroids inhibit cytokine production, adhesion protein activation, and inflammatory cell migration and activation. The side effects associated with systemic corticosteroids include, for instance, reversible abnormalities in glucose metabolism, increased appetite, fluid retention, weight gain, mood alteration, hypertension, peptic ulcer, and asceptic necrosis of bone. Some side effects associated with longer term use include adrenal axis suppression, growth suppression, dermal thinning, hypertension, diabetes mellitus, Cushing's syndrome, cataracts, muscle weakness, and in rare instances, impaired immune function. It is recommended that these types of compounds be used at their lowest effective dose.

Commonly used anemia drugs which are currently on the market or in development include recombinant human EPO (EPOGEN; PROCRIT), preparations of iron (ferrous and ferric, CHROMAGEN; FEOSOL; INFED; IROSPAN; NEPHRO-FER; NEPHRO-VITE; NIFEREX; NU-IRON; SLOW FE), vitamin B12, vitamin B6, folic acid (CHROMAGEN; FERRO-FOLIC; NEPHRO-FER; NIFEREX), ascorbic acid, certain metabolites of vitamin D (calcitriol and alphacalcidol; CALCIJEX; ROCALTROL), androgens, anabolic steroids (ANADROL), carnitine, recombinant IL-11 (NEUMEGA), and G-CSF (NEUPOGEN). In a specific embodiment the anemia medicament is recombinant EPO.

Drugs in common usage or development for the treatment of thrombocytopenia include glucocorticoids (prednisolone; prednisone; methylprednisolone; SOLUMEDROL), recombinant TPO, recombinant MGDF, pegylated recombinant MGDF, lisophylline, recombinant IL-1, recombinant IL-3, recombinant IL-6, recombinant IL-11 (NEUMEGA), and recombinant G-CSF (NEUPOGEN). In a specific embodiment the thrombocytopenia medicament is recombinant TPO.

Drugs in common usage or development for the treatment of neutropenia include glucocorticoids (prednisolone; prednisone; methylprednisolone; SOLUMEDROL), recombinant G-CSF (NEUPOGEN), recombinant GM-CSF (LEUKINE), recombinant M-CSF, recombinant IL-1, recombinant IL-3, recombinant IL-6, immunoglobulin G (SANDOGLOBULIN, IVEEGAM, GAMMAR-P, GAMIMNE N, GAMMAGARD S/D), androgens, recombinant IFN-γ (ACTIMMUNE), small molecule G-CSF mimetics, G-CSF receptor antagonists, IL-3 receptor antagonists, and uteroferrin. In a preferred embodiment the neutropenia medicament is recombinant G-CSF. Antibiotics are frequently administered in association with neutropenia medicaments to treat or reduce the risk of infection.

Drugs in common usage or development for the treatment of agranulocytosis agent that stimulates the production of granulocytes (e.g., recombinant G-CSF and recombinant GM-CSF) and hematopoeitic stem cells. Antibiotics are frequently administered in association with agranulocytosis medicaments to treat or reduce the risk of infection.

As noted above, the present invention encompasses co-administration of one or more additional agents in concert with an E-selectin antagonist. It will be understood that, in embodiments comprising administration of combinations of an E-selectin antagonist with other agents, the dosage of the antagonist may on its own comprise an effective amount and additional agent(s) may further augment the therapeutic or prophylactic benefit to the patient. Alternatively, the combination of the E-selectin antagonist and the additional agent(s) may together comprise an effective amount for preventing or treating the immunocompromised condition or infection. It will also be understood that effective amounts may be defined in the context of particular treatment regimens, including, e.g., timing and number of administrations, modes of administrations, formulations, etc.

In other aspects, the present invention also contemplates administering a high dose of the medical treatment that induces the immunocompromised condition, without inducing side effects. Ordinarily, when medical treatments such as chemotherapy and radiotherapy are administered in a high dose, a variety of side effects can occur, including the induction of the immunocompromised condition and infection. As a result of these side effects, the medical treatment is not administered in such high doses. In accordance with the present invention, such high doses of medical treatment (e.g., a higher dose of chemotherapeutic agent or radiation) which ordinarily induce side effects can be administered without inducing the side effects as long as the subject also receives an E-selectin antagonist. The type and extent of the side effects ordinarily induced by the medical treatment will depend on the particular treatment used.

Suitably, the E-selectin antagonist, and optionally the ancillary treatment, are administered on a routine schedule. Alternatively, the ancillary treatment may be administered as symptoms arise. A "routine schedule" as used herein, refers to a predetermined designated period of time. The routine schedule may encompass periods of time which are identical or which differ in length, as long as the schedule is predetermined. For instance, the routine schedule may involve administration of the im E-selectin antagonist on a daily basis, every two days, every three days, every four days, every five days, every six days, a weekly basis, a monthly basis or any set number of days or weeks therebetween, every two months, three months, four months, five months, six months, seven months, eight months, nine months, ten months, eleven months, twelve months, etc. Alternatively, the predetermined routine schedule may involve administration of the E-selectin antagonist on a daily basis for the first week, followed by a monthly basis for several months, and then every three months after that. Any particular combination would be covered by the routine schedule as long as it is determined ahead of time that the appropriate schedule involves administration on a certain day.

Additionally, the present invention provides pharmaceutical compositions for treating or preventing an immunocompromised condition that results from a medical treatment as broadly described above. The pharmaceutical compositions include an E-selectin antagonist optionally formulated in a pharmaceutically acceptable carrier. The pharmaceutical composition may include an ancillary or additional medicament as broadly described above. Typically, the E-selectin antagonist will be present in the pharmaceutical composition in an effective amount for preventing or treating the immunocompromised condition (e.g., anemia, thrombocytopenia, or neutropenia). The effective amount for preventing or treating the immunocompromised condition is that amount which completely or partially prevents the development of, prevents the worsening of, or treats the established existence of, the immunocompromised condition. In some instances, the effective amount for preventing or treating immunocompromised condition completely or partially prevents or treats clinical symptoms of that condition.

In addition to clinical outcomes measured in terms of physiology, in vitro assays measuring erythrocyte, platelet, granulocyte and total white blood cell counts may be used in determining a therapeutically effective amount of a particular E-selectin antagonist. These methods are standard medical laboratory techniques that are well known in the art. In common practice such measurements may be made by automated cell counting devices designed for that purpose, or they may be performed manually. Manual counts may be more accurate than automated counts when cell counts are particularly low.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients. Depending on the specific conditions being treated, the formulations may be administered systemically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. For injection, the active agents or drugs of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

The drugs can be formulated readily using pharmaceutically acceptable carriers well known in the art into dosages suitable for oral administration. Such carriers enable the compounds of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Pharmaceutical compositions suitable for use in the present invention include compositions wherein the active ingredients are contained in an effective amount to achieve its intended purpose. The dose of drug administered to a patient should be sufficient to effect a beneficial response in the patient over time such as a reduction in immunocompromised state, including a reduction in anemia, thrombocytopenia, agranulocytosis and/or neutropenia. The quantity of the drug(s) to be administered may depend on the subject to be treated inclusive of the age, sex, weight and general health condition thereof. In this regard, precise amounts of the drug(s) for administration will depend on the judgement of the practitioner. In determining the effective amount of the drug to be administered in the treatment or prophylaxis of the immunocompromised condition, the physician may evaluate tissue levels of E-selectin expression products, and degree of adiposity. In any event, those of skill in the art may readily determine suitable dosages of the drugs of the invention.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilisers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more drugs as described above with the carrier which constitutes one or more necessary ingredients. In general, the pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Dragee cores are provided with suitable coatings. For this purpose, concentrated sugar solutions may be used, which may optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments may be added to the tablets or dragee coatings for identification or to characterise different combinations of active compound doses.

Pharmaceutical which can be used orally include push-fit capsules made of gelatine, as well as soft, sealed capsules made of gelatine and a plasticizer, such as glycerol or sorbitol. The push-fit capsules can contain the active ingredients in admixture with filler such as lactose, binders such as starches, or lubricants such as talc or magnesium stearate and, optionally, stabilisers. In soft capsules, the active compounds may be dissolved or suspended in suitable liquids, such as fatty oils, liquid paraffin, or liquid polyethylene glycols. In addition, stabilisers may be added.

Dosage forms of the drugs of the invention may also include injecting or implanting controlled releasing devices designed specifically for this purpose or other forms of implants modified to act additionally in this fashion. Controlled release of an agent of the invention may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be effected by using other polymer matrices, liposomes or microspheres.

The drugs of the invention may be provided as salts with pharmaceutically compatible counterions. Pharmaceutically compatible salts may be formed with many acids, including but not limited to hydrochloric, sulphuric, acetic, lactic, tartaric, malic, succinic, etc. Salts tend to be more soluble in aqueous or other protonic solvents that are the corresponding free base forms.

For any compound used in the method of the invention, the therapeutically effective dose can be estimated initially from cell culture assays. For example, a dose can be formulated in animal models to achieve a circulating concentration range that includes the IC50 as determined in cell culture (e.g., the concentration of an active agent, which achieves a half-maximal inhibition in activity of an E-selectin polypeptide). Such information can be used to more accurately determine useful doses in humans.

Toxicity and therapeutic efficacy of such drugs can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilised. The exact formulation, route of administration and dosage can be chosen by the individual physician in view of the patient's condition. (See for example Fingl et al., 1975, in "The Pharmacological Basis of Therapeutics", Ch. 1 p 1).

Dosage amount and interval may be adjusted individually to provide plasma levels of the active agent which are sufficient to maintain E-selectin-inhibitory effects. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day. Stated in terms of patient body surface areas, usual dosages range from 0.5-1200 mg/m$^2$/day, commonly from 0.5-150 mg/m$^2$/day, typically from 5-100 mg/m$^2$/day.

Alternately, one may administer the compound in a local rather than systemic manner, for example, via injection of the compound directly into a tissue, which is preferably subcutaneous or omental tissue, often in a depot or sustained release formulation.

Furthermore, one may administer the drug in a targeted drug delivery system, for example, in a liposome coated with tissue-specific antibody. The liposomes will be targeted to and taken up selectively by the tissue.

In cases of local administration or selective uptake, the effective local concentration of the agent may not be related to plasma concentration.

In order that the invention may be readily understood and put into practical effect, particular preferred embodiments will now be described by way of the following non-limiting examples.

EXAMPLES

Example 1

Hematopoietic Stem Cell Turnover is Delayed 2.7-Fold In Vivo in the Bone Marrow of Mice Lacking the E-Selectin Gene Using C57BL/6 mice knocked-out for either or both the P- or E-selectin genes, it was shown that deletion of E-selectin, but not P-selectin, delays hematopoietic stem cell turn-over in the bone marrow in vivo. Mice were fed with BrdU in their drinking water for up to 14 days and sacrificed on days 3, 5, 7 and 14 to sort LSK34-hematopoietic stem cells. Following antibody staining with an anti-BrdU monoclonal antibody, 50% of LKS34-cells from the bone marrow of wild-type (WT) and P-sel–/– mice incorporated BrdU in 3.6 days whereas 50% of LKS34-cells from E-sel–/– and P/E-selectin double KO mice incorporated BrdU in 9.5 days (see FIG. 1). Thus, the cycling time of hematopoietic stem cell is 2.7 fold slower in the absence of E-selectin.

Figure 5:
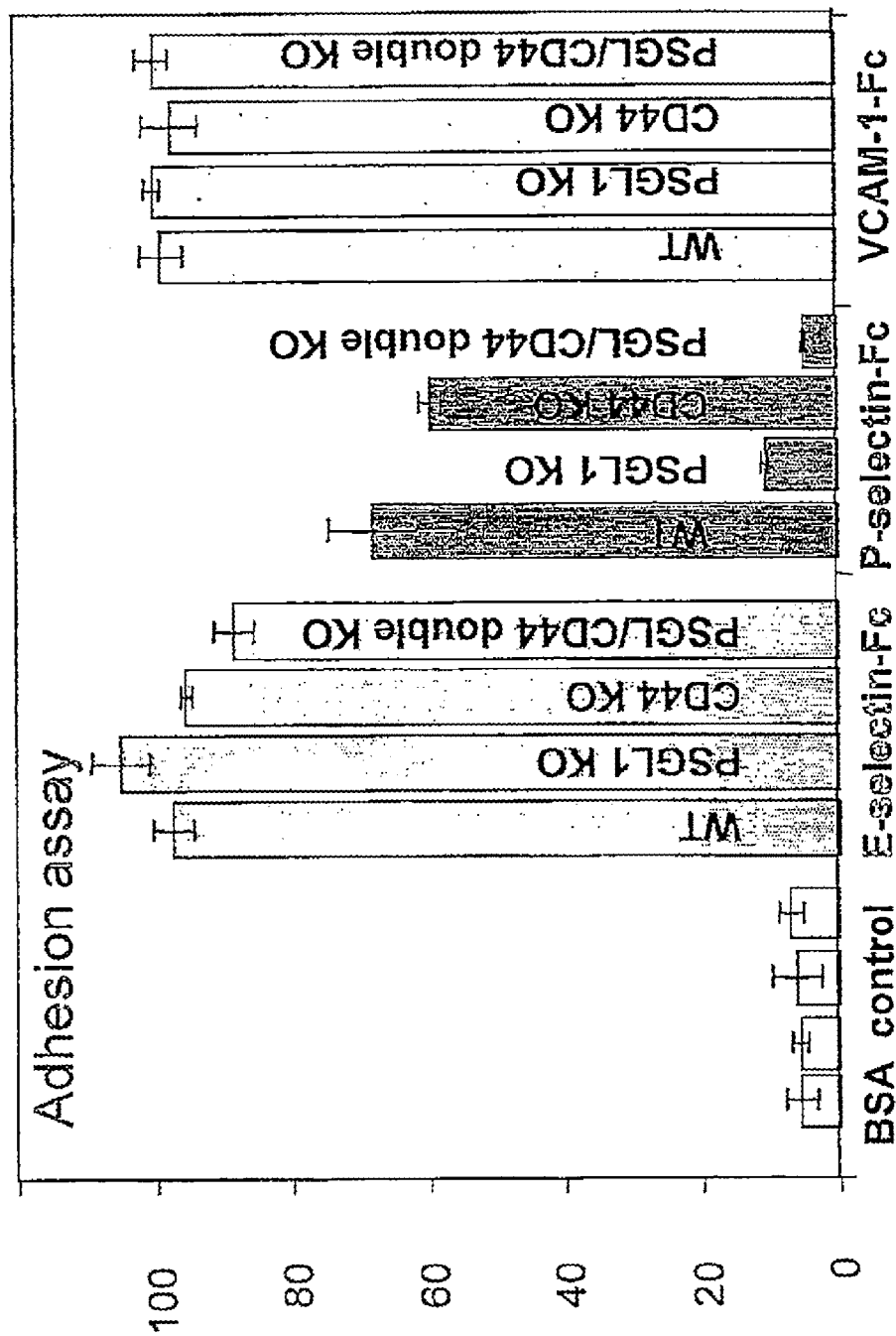
FIG. 5 is a graphical representation showing that deletion of the PSGL1 and CD44 genes has no effect on adhesion of hematopoietic progenitor cells to recombinant mouse E-selectin immobilised to plastic. Recombinant muE-selectin-IgG1Fc, muP-selectin-IgG1Fc and muVCAM1-IgG1Fc were adsorbed to the bottom of 96 well polystyrene tissue culture plates overnight, then the wells thoroughly washed and blocked before the addition of 30,000 calcein-labelled Lineage-negative CD117-positive cells from sorted from the bone marrow of wild-type, PSGL-1-/-, CD44-/-, or CD44-/-/PSGL-/- double KO mice. Data are expressed as a percentage of adherent cells and a means+/-standard deviation of triplicates.

To determine whether this effect was mediated by the two previously identified E-selectin receptors PSGL-1 and CD44, BrdU incorporation experiments were repeated with mice knocked-out for both the PSGL-1 and CD44 genes. LKS34-cell turnover in these mice was identical to that of wild-type suggesting that the effect is mediated by distinct unknown receptor(s). FIGS. 5 and 6 confirm that BM HSPC can adhere to E-selectin independent of PSGL-1 and CD44.

Example 2

In the Absence of E-Selectin, Bone Marrow Hematopoietic Stem Cells are Metabolically Less Active To support findings on hematopoietic stem cell turnover with BrdU, lineage-negative Sca1-positive CD117-positive (LSK) hematopoietic stem cells were isolated from the bone marrow and stained with Rhodamine 123, a viable dye that binds to mitochondrial membranes and is retained by metabolically active respirating cells.

A higher proportion of LKS cells from E-selectin–/– mice were rhodamine dull (43±3%) compared to LKS cells from wild-type mice (30±2%; p=0.002) confirming that a greater proportion of hematopoietic stem cells from E-selectin knock-out (KO) mice are quiescent (FIG. 2).

To confirm that metabolically active Rhodamine 123 dull cells cycle and incorporate BrdU less rapidly, Rhodamine bright and Rhodamine dull LKS cells were sorted from the same bone marrows as shown in FIG. 2. Rhodamine dull LKS cells incorporated BrdU 7 times less than Rhodamine bright LSK cells after 2 days of BrdU feeding to the mice, showing that less metabolically active Rhodamine dull stem cells are 7 times less likely to have cycled (and be BrdU-positive) during the two day period of BrdU feeding.

Rho bright LKS+→35% BrdU+ (2 days)

Rho dull LKS+→5% BrdU+ (2 days)

Taken together, these results confirm that in the absence of the E-selectin gene, hematopoietic stem cells residing in the bone marrow are less metabolically active and divide slower than in wild-type mice.

Example 3

Hematopoietic Stem Cell Turnover is Lower in E-Selectin KO Mice Following Cytotoxic Insult with 5-Fluorouracil To determine the effect of E-selectin gene deletion on hematopoietic stem cell recovery following cytotoxic stress, E-selectin KO and wild-type mice were injected with a single dose of 5-fluorouracil (5FU 150 mg/kg). As CD117 is strongly down-regulated in the bone marrow of 5FU-treated mice, the proportion of lineage-negative Sca1-positive CD41-negative CD48-negative CD150-positive long-term reconstituting hematopoietic stem cells[6] that incorporate BrdU was measured. For this propose, mice were sacrificed prior to and at day 3 or day 7 following 5-FU injection and BrdU was given continuously through drinking water in the last 17 hours before sacrificed. BrdU incorporation remained significantly lower in hematopoietic stem cells from E-selectin knock-out mice on days 3 and 7 post-5FU suggesting that the observed decreased HSC turn-over in the absence of E-selectin may protects them from the cytotoxic effect of 5FU (FIG. 3).

The recovery of long-term reconstituting hematopoietic stem cells was also enhanced in E-selectin$^{-/-}$ mice at day 7 post-5FU with a 5-fold increase in HSC numbers per femur compared to WT mice (FIG. 4).

The fact that the proliferation of hematopoietic stem cells was lower with increased absolute number of stem cells per femur at day 7 following chemotherapy with 5-FU shows that hematopoietic stem cells were more resistant to the cytotoxic effect of 5FU in E-selectin knock-out mice. Thus deletion of the E-selectin results in enhanced resistance of hematopoietic stem cells to the cytotoxic effect of chemotherapy.

Example 4

The Effect of E-Selectin on the Turn-Over of Hematopoietic Stem Cells is not Mediated by the Two Previously Described E-Selectin Ligands P-Selectin Glycoprotein Ligand-1 (PSGL-1 or CD162) and CD44

Figure 1B:
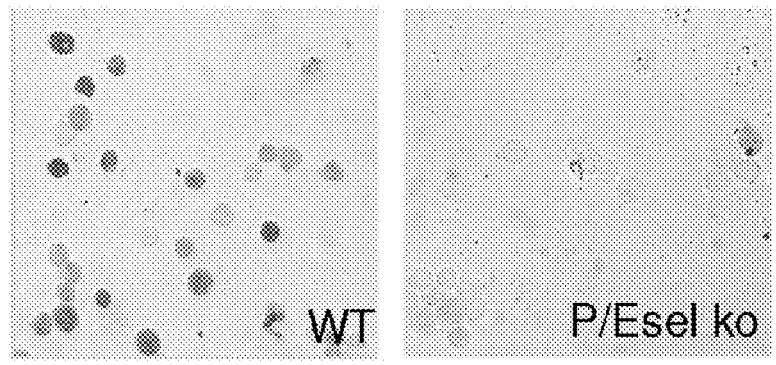

BrdU incorporation data from FIG. 1 show that LSK34- hematopoietic stem cells isolated from the bone marrow of mice lacking both the PSGL-1 and CD44 genes incorporate BrdU and cycle at the same rate as hematopoietic stem cells isolated from wild-type mice. Thus, this suggests that the delayed cell cycling observed in hematopoietic cells from E-selectin KO mice is not mediated by the two previously described E-selectin receptors PSGL-1 and CD44[10].

To confirm this further, the inventors measured interaction of hematopoietic stem cells isolated from mice lacking both PSGL-1 and CD44 with recombinant E-selectin. In adhesion assays in 96-well polystyrene plates coated with recombinant proteins made of the entire extracellular domain of mouse E-selectin, P-selectin or VCAM-1/CD106 fused to the Fc fragment of human IgG1 (muEsel-IgG1Fc, muPsel-IgG1Fc, or muVCAM1-IgG1Fc), deletion of the PSGL1 gene completely abrogated adhesion of bone marrow linage-negative CD117-positive hematopoietic progenitor cells to P-selectin, demonstrating that PSGL1 is the sole P-selectin receptor on bone marrow hematopoietic progenitor cells. In sharp contrast, the deletion of either or both the PSGL1 and CD44 genes, did not alter adhesion of bone marrow hematopoietic progenitor cells to E-selectin or to VCAM-1, an unrelated cell adhesion molecule whose cellular receptors are α4 integrins/CD49d (FIG. 5).

In a second assay, binding of recombinant E-selectin and P-selectin was directly measured in solution by flow cytometry. For this purpose, recombinant human P-selectin or E-selectin extracellular domains fused with the Fc portion of human IgM were used as selectins required prior clustering to bind to their cellular receptors. As IgM are decameric proteins, each fusion recombinant protein is a decamer or either P-selectin or E-selectin. The clustering resulting from decamerization of selectin enables them to directly interact in solution with their cellular receptors. The inventors therefore measured the binding of recombinant selectin-IgM Fc fusion proteins to bone marrow cells isolated from wild-type, PSGL1-/-, CD44-/- or PSGL1-/- CD44-/- double KO mice. Detection by flow cytometry was performed by pre-complexing the selectin-IgMFc fusion proteins with a Cy5-conjubated donkey anti-human IgM antibody. FIG. 6 shows that while deletion of both PSGL1 and CD44 genes markedly reduced binding of recombinant E-selectin-IgMFc to bone marrow granulocytes, the deletion of these two genes did not decrease the binding of recombinant E-selectin-IgMFc to bone marrow LSK hematopoietic stem cells. Thus these experiments confirm that PSGL1 and CD44 are necessary and sufficient for E-selectin binding to mature granulocytes, and that hematopoietic stem cells can bind and adhere to E-selectin via alternative receptors which are not encoded by the PSGL1 and C44 genes.

Materials and Methods

Incorporation of 6-Bromodeoxyurine (BrdU) to Measure Hematopoietic Stem Cell Turnover In Vivo The aim of this method is to measure the proportion of hematopoietic stem cells that incorporate the nucleotide analog BrdU into their genomic DNA during a given period of time in vivo. Since BrdU can only integrate into genomic DNA during the S phase of the cell cycle, the proportion of cells that have incorporated BrdU is equal to the proportion of cells that have divided or are dividing during the period of animal feeding with BrdU[5].

Adult mice (10-14 week-old) with homologous deletion of the E-selectin gene (Sele), the P-selectin gene (Selp), both the E-selectin and P-selectin genes, or both the CD162/PSGL1 (Selplg) and CD44 (Cd44) genes were given 1 mg/mL BrdU solubilised in their drinking water for a continuous period of up to 14 days.

At various time-points, mice were sacrificed and femurs, tibias and iliac crest harvested. One cleaned, bones were crushed with a mortar and pestle in phosphate-buffered saline containing 2% new-born calf serum to extract bone marrow cells. Mononucleated bone marrow cells were isolated by centrifugation at 500×g on a density gradient made with 62.5% Percoll.

Cells expressing c-KIT/CD117 were next enriched by magnetic cell sorting (MACS) using mouse CD117 magnetic microbeads (Miltenyi Biotec). For this purpose, mononucleated cells at the Percoll interface were washed in phosphate-buffered saline containing 0.5% bovine serum albumin and 2 mM ethylene diamine tetraacetate (MACS washing buffer), resuspended at $10^8$ cells/mL and subsequently incubated with 1.5 µL mouse CD117 microbeads per $10^7$ cells. Cells were incubated for 15 minutes on ice with magnetic beads, washed once in MACS washing buffer, pelleted at 440×g, resuspended at $10^8$ cells/mL in MACS washing buffer. Cells expressing CD117 were then enriched by separation on an autoMACS Separator (Miltenyi Biotec) using the cell depletion program.

Hematopoietic stem cells were further isolated from this CD117 MACS-enriched population by fluorescence-activated cell sorting (FACS) using the following panel of antibodies: a) biotinylated antibodies against lineage-specific antigens CD3, CD5, B220/CD45R, CD11b, Gr-1/Ly-6C/G, Ter119 together with streptavidin conjugated to PercP-Cy5.5; b) fluorescein isothiocyanate (FITC) conjugated anti-CD34; c) phycoerythrin (PE) conjugated anti-Sca-1/Ly-6A/E; d) allophycocyanin (APC) conjugated anti-CD117 antibodies. Hematopoietic stem cells with the phenotype Lineage-negative, Sca-1-positive, CD117-positive and CD34-negative (LSK34-), were sorted on a FACS Aria cell sorter (BD Biosciences), collected in phosphate-buffered saline containing 2% newborn calf serum and cytospun on positively charged glass slides. Once cytospun on glass slides, LSK34-cells were air dried and fixed with the fixative provided in the BD Pharmingen BrdU detection kit (catalog#551321). Staining with a monoclonal antibody specific for BrdU was then performed exactly following the kit instructions. Following counterstaining with dilute hematoxylin and mounting with Aquamount, the proportion of cells staining for BrdU was manually counted using a microscope.

In additional experiments, BrdU incorporation was measured in a purer population of hematopoietic stem cells. This population has the phenotype Lineage-negative, Sca1-positive, CD117-positive, CD41-negative, CD48-negative, CD150-positive. This very rare population (0.05% of the bone marrow) has been described to be homogenous with long-term reconstitution activity (>16 weeks in a mouse). Specifically, 50% of lethally irradiated mice transplanted with a single cell exhibiting this phenotype can reconstitute a full hematopoietic/immune system for the full life-time from this single cell[6]. The combination of antibodies to sort these cells is as follows: a) biotinylated antibodies against lineage-specific antigens CD3, CD5, B220/CD45R, CD11b, Gr-1/Ly-6C/G, CD41, Ter119 together with streptavidin conjugated to PercP-Cy5.5; b) fluorescein isothiocyanate (FITC) conjugated anti-CD48; c) phycoerythrin (PE) conjugated anti-CD150; d) PECy7 conjugated anti-Sca-1/Ly-6A/E; f) allophycocyanin (APC) conjugated anti-CD117 antibodies.

Determination of Hematopoietic Stem Cell Metabolic Activity by Flow Cytometry Using Rhodamine123 Fluorescent Dye Rhodamine-123 is a vital fluorescent dye that incorporates preferentially in mitochondria. It has been previously described that most quiescent hematopoietic stem cells with highest reconstituting potential following transplant incorporate low levels of rhodamine-123 whereas metabolically active stem cells incorporate high levels of rhodamine 123[5,7].

For this purpose, bone marrow cells extracted as above were resuspended at $10^6$/mL in PBS with 2% fetal calf serum and incubated with Rhodamine-123 (0.1 μg/mL) at 37° C. for 20 min then washed in PBS with 2% fetal calf serum and incubated at $10^6$/mL in PBS+2% serum for another 15 min at 37° C. to efflux excess dye incorporated in cells. Following Rho123 efflux, cells were kept on ice and subsequently stained with biotinylated lineage antibodies (CD3,CD5,B220,Gr-1,F4/80,Ter119), CD117-APC, Sca-1-PE then washed and incubated with strepatvidin-PerCPCy5.

Lineage-negative, CD117-positive, Sca1-positive cells were analysed by flow cytometry for Rhodamine-123 fluorescence on a BD Biosciences FACS Calibur flow cytometer

Measurement of HSC Cycling and Number In Vivo Following Cytotoxic Insult with the Chemotherapeutic Drug 5-Fluorouracil (5-FU)

Adult mice (10-14 week-old) with homologous deletion of the E-selectin gene were administered intravenously a single dose of 5-FU at 150 mg/kg. At days 2 and 6 following 5-FU, mice were injected intraperitoneally BrdU 100 mg/kg followed by a continuous dose of 1 mg/mL in their drinking water at a concentration of 1 mg/mL. 18 hours following the injection of BrdU. Mice were sacrificed, their bone marrow cells collected as described above and stained with the following combination of antibodies: a) biotinylated antibodies against lineage-specific antigens CD3, CD5, B220/CD45R, CD11b, Gr-1/Ly-6C/G, CD41, Ter119 together with streptavidin conjugated to PercP-Cy5.5; b) fluorescein isothiocyanate (FITC) conjugated anti-CD48; c) phycoerythrin (PE) conjugated anti-CD150; d) PECy7 conjugated anti-Sca-1/Ly-6A/E; f) allophycocyanin (APC) conjugated anti-CD117 antibodies. True hematopoietic stem cells with the phenotype Lineage-negative, Seal-positive, CD117-positive, CD41-negative, CD48-negative, CD150-positive were counted and sorted as described above. Sorted cells were cytospun on glass slides and stained with anti-BrdU antibodies as described above.

Cell Adhesion Assay of Hematopoietic Progenitor Cells on Immobilised Recombinant Mouse E-Selectin and P-Selectin Fusion Proteins 96-well polystyrene cell culture plates were coated overnight at 4*C with 504 per well of phosphate buffered saline containing 3 μg/ml of recombinant proteins made of the entire extracellular domain of mouse E-selectin, P-selectin or VCAM-1/CD106 fused to the Fc fragment of human IgG1 (muEsel-IgG1Fc, muPsel-IgG1Fc, or muVCAM1-IgG1Fc respectively, from R&D Systems)) as previously described 8. Prior to the experiment, plates were flicked to remove excess coating solution and filled with Hepes buffered saline supplemented with 2% bovine serum albumin to block non-specific adhesion to plastic surfaces. Following 1 hour incubation at 37° C., coated wells were washes twice with cell adhesion buffer (Iscove's modified Dulbecco medium supplemented with 0.2% bovine serum albumin and 1 mM $CaCl_2$).

Bone marrow cells from CD44 KO, PSGL1 KO and CD44-PSGL1 double KO mice were stained with FITC-conjugated biotinylated rat monoclonal antibodies specific for CD3, CD5, B220/CD45R, CD11b, Gr1 and Ter119 lineage-specific antigens and PE-conjugated anti-CD117 antibody. Lineage-negative CD117-positive hematopoietic progenitor cells were then sorted by fluorescence activated cell sorting on an Aria cell sorter (BD Biosciences).

Sorted Lineage-negative CD117-positive hematopoietic progenitor cells when then washed and resuspended in cell adhesion buffer and labelled with the intracellular fluorescent dye calcein-AM (Molecular Probes) for 40 minutes at 37° C. 8. Following labelling with calcein-AM, cells were washed in cell adhesion buffer and resuspended at 105 cells/mL. 100 μL (104 cells) were deposited in each well coated with muEsel-IgG1Fc, muPsel-IgG1Fc, muVCAM1-IgG1Fc, or serum albumin alone, centrifuged at 200×g for 5 minutes to sediments cells at the bottom of coated wells and further incubated for 40 minutes on ice. Following this incubations, non-adherent cells were removed by 4 gentle washes with cell adhesion buffer. The fluorescence contained in the remaining adherent cells was measured on a Fluorostar plate fluorometer following exciting at 488 nm using a 530 nm filter.

Measurement of the Binding of Recombinant E-Selectin and P-Selectin on Haematopoietic Stem Cells in Suspension Recombinant human E-selectin and P-selectin extracellular domains fused with the Fc fragment of human IgM (selectin-IgMFc) were produced as supernatants following transfection of COS7 cell line with pCDM8 plasmids containing the corresponding cDNA[9]. Following transfection, COS7 medium was replaced by serum-free X-VIVO10 medium and conditioned for three days post transfection. Saturating doses of selectin-containing supernatants were determined by flow cytometry using the human myeloid cell line KG1a.

Prior to the experiment, recombinant selectin-IgMFc fusion proteins were complexed with Cy5-conjugated donkey IgG F(ab)'2 fragments anti-human IgM. For this purpose, serum-free supernatants were incubated with an equal volume of cell adhesion buffer (Iscove's modified Dulbecco medium supplemented with 0.2% bovine serum albumin and 1 mM $CaCl_2$) containing a 1/50 dilution of Cy5-conjugated donkey IgG F(ab)'2 fragments anti-human IgM (Jackson ImmunoResearch) for 2 hours at 4° C.

Bone marrow cells from CD44 KO, PSGL1 KO and CD44-PSGL1 double KO mice were depleted of lineage-positive cells on an autoMACS Separator using biotinylated rat monoclonal antibodies specific for CD3, CD5, B220/CD45R, CD11b, Gr1 and Ter119 lineage-specific antigens and streptavidin-coated magnetic immunobeads (Miltenyi Biotec). Following depletion, lineage-negative bone marrow cells were stained on ice for 40 minutes with FITC-conjugated anti-Sca1/Ly6A-E and PE-conjugated anti-CD117 rat monoclonal antibodies. Following washing with cell adhesion buffer described above, $10^6$ labelled lineage-depleted bone marrow cells were resuspended in a volume of 25 μL of cell adhesion buffer. 25 μL of selectin-IgMFc pre-complexed with Cy5-conjugated donkey anti-human IgM was then added to the cells and further incubated for 40 minutes at 4*C. Negative controls were performed by adding the calcium chelator ethylene diamine tetraacetic acid (5 mM) in the cell adhesion buffer as selectin-mediated interactions are strictly calcium-dependant. Binding of selectin-IgMFc fusion proteins was measured by flow cytometry on a FACS Calibur flow cytometer (BD Biosciences).

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

BIBLIOGRAPHY

1. Alousi A, de Lima M. Reduced-intensity conditioning allogeneic hematopoietic stem cell transplantation. Clin Adv Hematol Oncol. 2007; 5:560-570.
2. Fruehauf S, Wermann K, Buss E C, et al. Protection of hematopoietic stem cells from chemotherapy-induced toxicity by multidrug-resistance 1 gene transfer. Recent Results Cancer Res. 1998; 144:93-115.
3. Bogden A E, Carde P, de Paillette E D, Moreau J P, Tubiana M, Frindel E. Amelioration of chemotherapy-induced toxicity by cotreatment with AcSDKP, a tetrapeptide inhibitor of hematopoietic stem cell proliferation. Ann N Y Acad. Sci. 1991; 628:126-139.
4. Mauch P, Constine L, Greenberger J, et al. Hematopoietic stem cell compartment: acute and late effects of radiation therapy and chemotherapy. Int J Radiat Oncol Biol Phys. 1995; 31:1319-1339,
5. Bradford G B, Williams B, Rossi R, Bertoncello I. Quiescence, cycling, and turnover in the primitive hematopoietic stem cell compartment. Exp Hematol. 1997; 25:445-453.
6. Kiel M J, Yilmaz O H, Iwashita T, Yilmaz O H, Terhorst C, Morrison S J. SLAM family receptors distinguish hematopoietic stem and progenitor cells and reveal endothelial niches for stem cells. Cell. 2005; 121:1109-1121.
7. McKenzie J L, Takenaka K, Gan C H, Doedens M, Dick J E. Low rhodamine 123 retention identifies long-term human hematopoietic stem cells within the Lin-CD34+ CD38- population 10.1182/blood-2006-06-030270. Blood. 2007; 109:543-545.
8. Winkler I G, Snapp K R, Simmons P J, Levesque J-P. Adhesion to E-selectin promotes growth inhibition and apoptosis of human and murine hematopoietic progenitor cells independent of PSGL-1. Blood, 2004; 103:1685-1692.
9. Maly P, Thall A, Petryniak B, et al. The alpha(1,3) fucosyltransferase Fuc-TVII controls leukocyte trafficking through an essential role in L-, E-, and P-selectin ligand biosynthesis. Cell. 1996; 86:643-653.
10. Katayama Y, Hidalgo A, Chang J, Peired A, Frenette P S. CD44 is a physiological E-selectin ligand on neutrophils. J Exp Med. 2005; 201:1183-1189.

What is claimed is:

1. A method for treating an immunocompromised condition in a subject, which condition results from a medical treatment comprising chemotherapy or radiation therapy, the method comprising administering to the subject an E-selectin antagonist in an effective amount to treat the immunocompromised condition, wherein the subject is not exposed to an ancillary treatment that comprises transplantation of hematopoietic stem cells (HSC), other than autologous HSC, and wherein the E-selectin antagonist binds to E-selectin.

2. The method of claim 1, wherein the immunocompromised condition is selected from neutropenia, agranulocytosis, thrombocytopenia, and anemia.

3. The method of claim 1, wherein the medical treatment is chemotherapy.

4. The method of claim 1, wherein the medical treatment is radiation therapy.

5. The method of claim 1, wherein the E-selectin antagonist is administered to the subject simultaneously, sequentially or separately with the medical treatment.

6. The method of claim 1, wherein the E-selectin antagonist is administered to the subject prior to, during or after the medical treatment.

7. The method of claim 1, wherein the administration of the E-selectin antagonist is a prophylactic treatment.

8. The method of claim 7, wherein the subject is preparing to undergo chemotherapy.

9. The method of claim 7, wherein the subject is preparing to undergo radiation treatment.

10. The method of claim 1, wherein the administration of the E-selectin antagonist is a therapeutic treatment.

11. The method of claim 10, wherein the subject has received at least one dose of chemotherapy.

12. The method of claim 10, wherein the subject has received at least one radiation treatment.

13. The method of claim 1, further comprising exposing the subject to an ancillary treatment that treats or prevents the immunocompromised condition.

14. The method of claim 13, wherein the immunocompromised condition is anemia and the ancillary treatment comprises administering to the subject an anemia medicament selected from recombinant erythropoietin (EPO), recombinant granulocyte-macrophage colony-stimulating factor (GM-CSF), recombinant granulocyte colony-stimulating factor (G-CSF), recombinant interleukin 11 (IL-11), ferrous iron, ferric iron, vitamin B12, vitamin B6, vitamin C, vitamin D, calcitriol, alphacalcidol, folate, androgen, and carnitine.

15. The method of claim 13, wherein the immunocompromised condition is thrombocytopenia and the ancillary treatment comprises administering to the subject a thrombocytopenia medicament selected from a glucocorticoid, recombinant thrombopoietin (TPO), recombinant megakaryocyte growth and development factor (MGDF), pegylated recombinant MGDF, lisophylline, recombinant IL-1, recombinant IL-3, recombinant IL-6, and recombinant IL-11.

16. The method of claim 13, wherein the immunocompromised condition is neutropenia and the ancillary treatment comprises administering to the subject a neutropenia medicament selected from glucocorticoid, recombinant G-CSF, recombinant GM-CSF, recombinant macrophage colony-stimulating factor (M-CSF), recombinant IL-1, recombinant IL-3, recombinant IL-6, immunoglobulin, androgens, recombinant IFN-γ, small molecule G-CSF mimetics, G-CSF receptor antagonists, IL-3 receptor antagonists, and uteroferrin.

17. The method of claim 13, wherein the immunocompromised condition is agranulocytosis and the ancillary treatment comprises administering to the subject an agent that stimulates the production of granulocytes.

18. The method of claim 13, wherein the immunocompromised condition is agranulocytosis and the ancillary treatment comprises transplanting hematopoietic stem cells into the subject.

19. The method of claim 13, wherein the E-selectin antagonist is administered to the subject simultaneously, sequentially or separately with the ancillary treatment.

20. The method of claim 1, further comprising administering at least one anti-infective agent, selected from antimicrobials, antivirals, anthelmintics, antiprotozoals and nematocides.

21. The method of claim 20, wherein the E-selectin antagonist is administered to the subject simultaneously, sequentially or separately with the at least one anti-infective agent.

22. The method of claim 20, wherein the at least one anti-infective agent is an antibiotic or antifungal agent.

23. The method of claim 1, wherein the E-selectin antagonist is administered on a routine schedule selected from the group consisting of every day, at least twice a week, at least three times a week, at least four times a week, at least five times a week, at least six times a week, every week, every other week, every third week, every fourth week, every month, every two months, every three months, every four months, and every six months.

24. The method of claim 1, wherein the medical treatment comprises inhibiting the growth or proliferation of a tumor cell.

25. The method of claim 1, wherein the medical treatment comprises treatment of a cancer.

26. The method of claim 25, wherein the cancer is a primary cancer.

27. The method of claim 25, wherein the cancer is a metastatic cancer.

28. The method of claim 1, wherein the medical treatment comprises treatment of an autoimmune disease.

29. The method of claim 1, wherein the E-selectin antagonist is selected from antigen-binding molecules that bind to E-selectin in an immuno-interactive manner, peptides that bind to E-selectin to block E-selectin mediated cell-cell adhesion, carbohydrate mimetics of E-selectin ligands that bind E-selectin, and peptide mimetics of E-selectin ligands that bind E-selectin.

30. A method for increasing the dose of radiation or chemotherapy administered to a subject undergoing radiation therapy or chemotherapy, the method comprising administering the radiation or chemotherapy to the subject in a dose that ordinarily induces immunocompromising effects, together with an E-selectin antagonist in an effective amount to lessen the immunocompromising effects of the radiation or chemotherapy, wherein the subject is not exposed to an ancillary treatment that comprises transplantation of hematopoietic stem cells (HSC), other than autologous HSC, and wherein the E-selectin antagonist binds to E-selectin.

31. A method for reducing the immunocompromising side-effects of a medical treatment comprising chemotherapy or radiation therapy, the method comprising administering to the subject an E-selectin antagonist in an effective amount to reduce the immunocompromising side-effects of the medical treatment, wherein the subject is not exposed to an ancillary treatment that comprises transplantation of hematopoietic stem cells (HSC), other than autologous HSC, and wherein the E-selectin antagonist binds to E-selectin.

32. The method of claim 31, wherein the medical treatment is chemotherapy.

33. The method of claim 31, wherein the medical treatment is radiation therapy.

34. The method of claim 31, wherein the E-selectin antagonist is administered to the subject simultaneously, sequentially or separately with the medical treatment.

35. The method of claim 31, wherein the E-selectin antagonist is administered to the subject prior to, during or after the medical treatment.

36. The method of claim 31, wherein the administration of the E-selectin antagonist is a prophylactic treatment.

37. The method of claim 36, wherein the subject is preparing to undergo chemotherapy.

38. The method of claim 36, wherein the subject is preparing to undergo radiation treatment.

39. The method of claim 31, wherein the administration of the E-selectin antagonist is a therapeutic treatment.

40. The method of claim 39, wherein the subject has received at least one dose of chemotherapy.

41. The method of claim 39, wherein the subject has received at least one radiation treatment.

42. The method of claim 31, further comprising administering at least one anti-infective agent selected from antimicrobials, antivirals, anthelmintics, antiprotozoals, and nematocides.

43. The method of claim 42, wherein the E-selectin antagonist is administered to the subject simultaneously, sequentially, or separately with the at least one anti-infective agent.

44. The method of claim 42, wherein the at least one anti-infective agent is an antibiotic or antifungal agent.

45. The method of claim 31, wherein the E-selectin antagonist is administered on a routine schedule selected from the group consisting of every day, at least twice a week, at least three times a week, at least four times a week, at least five times a week, at least six times a week, every week, every other week, every third week, every fourth week, every month, every two months, every three months, every four months, and every six months.

46. The method of claim 31, wherein the medical treatment comprises inhibiting the growth or proliferation of a tumor cell.

47. The method of claim 31, wherein the medical treatment comprises treatment of a cancer.

48. The method of claim 47, wherein the cancer is a primary cancer.

49. The method of claim 47, wherein the cancer is a metastatic cancer.

50. The method of claim 31, wherein the medical treatment comprises treatment of an autoimmune disease.

51. The method of claim 31, wherein the E-selectin antagonist is selected from antigen-binding molecules that bind to E-selectin in an immuno-interactive manner, peptides that bind to E-selectin to block E-selectin mediated cell-cell adhesion, carbohydrate mimetics of E-selectin ligands that bind E-selectin, and peptide mimetics of E-selectin ligands that bind E-selectin.

* * * * *